_(12)_ United States Patent
Bennett et al.

US006339066B1

(10) Patent No.: US 6,339,066 B1
(45) Date of Patent: *Jan. 15, 2002

(54) ANTISENSE OLIGONUCLEOTIDES WHICH HAVE PHOSPHOROTHIOATE LINKAGES OF HIGH CHIRAL PURITY AND WHICH MODULATE $\beta_I$, $\beta_{II}$, $\gamma$, $\delta$, E, $\zeta$ AND $\eta$ ISOFORMS OF HUMAN PROTEIN KINASE C

(75) Inventors: C. Frank Bennett, Carlsbad; Nicholas M. Dean, Encinitas; Phillip Dan Cook, Escondido, all of CA (US); Glenn Hoke, Mt. Airy, MD (US)

(73) Assignee: ISIS Pharmaceuticals, Inc., Carlsbad, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/829,637

(22) Filed: Mar. 31, 1997

Related U.S. Application Data

(63) Continuation-in-part of application No. 08/481,066, filed on Jun. 7, 1995, now Pat. No. 5,959,096, which is a continuation-in-part of application No. 08/089,996, filed on Jul. 9, 1993, now Pat. No. 5,703,054, which is a continuation-in-part of application No. 07/852,852, filed on Mar. 16, 1992, now abandoned, said application No. 08/829,637, is a continuation-in-part of application No.08/468,569, filed on Jun. 6, 1995, now Pat. No. 5,620,963, which is a continuation-in-part of application No. 08/297,703, filed on Aug. 29, 1994, now Pat. No. 5,506,212, which is a continuation of application No. 07/777,007, filed on Oct. 16, 1991, now Pat. No. 5,246,432, and a continuation-in-part of application No. 08/058,023, filed on May 5, 1993, now Pat. No. 5,521,302, which is a division of application No. 07/777,760, filed on Oct. 15, 1991, now Pat. No. 5,212,295, and a continuation-in-part of application No. 07/777,007, which is a continuation-in-part of application No. 07/463,358, filed on Jan. 11, 1990, now abandoned, said application No. 08/829,637, is a continuation-in-part of application No.08/469,851, filed on Jun. 6, 1995, now Pat. No. 5,587,361, which is a continuation-in-part of application No. 08/297,703, which is a continuation of application No. 07/777,007, and a continuation-in-part of application No. 08/058,023, which is a division of application No. 07/777,760, and a continuation-in-part of application No. 07/777,007, which is a continuation-in-part of application No. 07/463,358, said application No. 08/829,637, is a continuation-in-part of application No.08/470,129, filed on Jun. 6, 1995, now Pat. No. 5,635,488, which is a continuation-in-part of application No. 08/297,703, which is a continuation of application No. 07/777,007, and a continuation-in-part of application No. 08/058,023, which is a division of application No. 07/777,760, and a continuation-in-part of application No. 07/777,007, which is a continuation-in-part of application No. 07/463,358, said application No. 08/829,637, is a continuation-in-part of application No.07/770,760, which is a continuation-in-part of application No. PCT/US91/00243, filed on Jan. 11, 1991, which is a continuation-in-part of application No. 07/463,358, and a continuation-in-part of application No. 07/566,977, filed on Aug. 13, 1990, now abandoned, said application No. 08/829,637, is a continuation-in-part of application No.08/297,703, which is a continuation of application No. 07/777,007, which is a continuation-in-part of application No. 07/463,358.

(51) Int. Cl.[7] .......................... C07H 21/04; A61K 48/00; C12Q 1/68
(52) U.S. Cl. .............................. 514/44; 435/6; 435/91.1; 435/366; 435/375; 536/23.1; 536/24.31; 536/24.5
(58) Field of Search .................... 435/6, 91.1, 172.3, 435/320.1, 354, 366, 368, 371, 375, 440; 536/23.1, 23.2, 24.31, 24.5; 514/44

(56) References Cited

U.S. PATENT DOCUMENTS

| | | | |
|---|---|---|---|
| 3,336,289 A | 8/1967 | Wechter et al. | 536/26.7 |
| 3,687,808 A | 8/1972 | Merrigan et al. | 536/24.5 |
| 3,792,039 A | 2/1974 | Erickson et al. | 536/25.5 |
| 3,846,402 A | 11/1974 | Eckstein et al. | 536/26.23 |
| 4,310,662 A | 1/1982 | Crea | 536/25.31 |

(List continued on next page.)

FOREIGN PATENT DOCUMENTS

| | | |
|---|---|---|
| EP | 0506242 | 9/1992 |
| JP | 7011506 | 4/1970 |
| JP | 7307354 | 3/1973 |
| WO | WO 89/03683 | 5/1989 |

(List continued on next page.)

OTHER PUBLICATIONS

Rojanasakul, Antisense Oligonucleotide Therapeutics: Drug Delivery and Targeting, Advanced Drug Delivery Review 18, 115–131 (1996).*

(List continued on next page.)

Primary Examiner—Andrew Wang
Assistant Examiner—Mark L. Shibuya
(74) Attorney, Agent, or Firm—Woodcock Washburn LLP

(57) ABSTRACT

Compositions and methods are provided for the treatment and diagnosis of diseases associated with the expression of one or more of the $\beta_I$, $\beta_{II}$, $\gamma$, $\delta$, $\epsilon$, $\zeta$ or $\eta$ isoforms (isozymes) of protein kinase C (PKC). Oligonucleotides are provided which are targeted to nucleic acids encoding PKC-$\beta_I$, PKC-$\beta_{II}$, PKC-$\gamma$, PKC-$\delta$, PKC-$\epsilon$, PKC-$\zeta$ or PKC-$\eta$. Provided herein are oligonucleotides specifically hybridizable with a translation initiation site, 5'-untranslated region, 3'-untranslated region or other targeted region of a $\beta_I$, $\beta_{II}$, $\gamma$, $\delta$, $\epsilon$, $\zeta$ or $\eta$ isoform of PKC, wherein at least about 75% of the nucleoside units of a given oligonucleotide are joined together by a stereospecific (i.e., Sp or Rp) phosphorothioate 3' to 5' linkages. In preferred embodiments, the oligonucleotides of the disclosure additionally contain one or more chemical modifications. Also disclosed are methods of using the oligonucleotides of the invention for modulating the expression of at least one of the $\beta_I$, $\beta_{II}$, $\gamma$, $\delta$, $\epsilon$, $\zeta$ or $\eta$ isoforms of PKC and for treating animals suffering from disease amenable to therapeutic intervention by modulating the expression of one or more of the $\beta_I$, $\beta_{II}$, $\gamma$, $\delta$, $\epsilon$, $\zeta$ or $\eta$ isoforms of PKC.

42 Claims, 15 Drawing Sheets

U.S. PATENT DOCUMENTS

| | | |
|---|---|---|
| 4,381,344 A | 4/1983 | Rideout et al. |
| 4,500,707 A | 2/1985 | Caruthers et al. ......... 536/25.34 |
| 4,511,713 A | 4/1985 | Miller et al. |
| 4,591,614 A | 5/1986 | Miller et al. ............... 536/24.5 |
| 4,663,446 A | 5/1987 | Wright ...................... 536/26.26 |
| 4,689,320 A | 8/1987 | Kaja ............................ 514/44 |
| 4,760,017 A | 7/1988 | McCormick |
| 4,806,463 A | 2/1989 | Goodchild et al. ............. 435/5 |
| 4,835,263 A | 5/1989 | Nguyen et al. ................ 536/27 |
| 4,876,335 A | 10/1989 | Yamane et al. |
| 4,965,350 A | 10/1990 | Inoue et al. |
| 5,004,810 A | 4/1991 | Draper ......................... 536/27 |
| 5,011,909 A | 4/1991 | Borovsky et al. |
| 5,034,506 A | 7/1991 | Summerton et al. ........ 528/391 |
| 5,087,617 A | 2/1992 | Smith .......................... 514/44 |
| 5,098,890 A | 3/1992 | Gewirtz et al. ............... 514/44 |
| 5,130,253 A | 7/1992 | Borovsky et al. |
| 5,135,917 A | 8/1992 | Burch .......................... 514/44 |
| 5,138,045 A | 8/1992 | Cook et al. .................... 536/27 |
| 5,166,195 A | 11/1992 | Ecker ........................... 514/44 |
| 5,194,428 A | 3/1993 | Agrawal et al. ............... 514/44 |
| 5,212,295 A | 5/1993 | Cook ......................... 536/26.7 |
| 5,218,105 A | 6/1993 | Cook et al. .............. 536/25.31 |
| 5,242,906 A | 9/1993 | Pagano et al. ................ 514/44 |
| 5,248,670 A | 9/1993 | Draper et al. .................. 514/44 |
| 5,264,423 A | 11/1993 | Cohen et al. .................. 514/44 |
| 5,276,019 A | 1/1994 | Cohen et al. .................. 514/44 |
| 5,286,717 A | 2/1994 | Cohen et al. .................. 514/44 |
| 5,378,825 A | 1/1995 | Cook et al. .............. 536/25.34 |
| 5,386,023 A | 1/1995 | Sanghvi et al. ............ 536/25.3 |
| 5,457,191 A | 10/1995 | Cook et al. .............. 536/27.13 |
| 5,459,255 A | 10/1995 | Cook et al. .............. 536/27.13 |
| 5,506,212 A | 4/1996 | Hoke et al. .................... 514/44 |
| 5,512,438 A | 4/1996 | Ecker ............................ 435/6 |
| 5,521,302 A | 5/1996 | Cook et al. .............. 536/25.31 |
| 5,539,082 A | 7/1996 | Nielsen et al. ............... 530/300 |
| 5,541,307 A | 7/1996 | Cook et al. ................. 536/23.1 |
| 5,554,746 A | 9/1996 | Ravikumar et al. ......... 540/200 |
| 5,571,902 A | 11/1996 | Ravikumar et al. ........ 536/22.1 |
| 5,578,718 A | 11/1996 | Cook et al. .............. 536/27.21 |
| 5,587,361 A | 12/1996 | Cook et al. .................... 514/44 |
| 5,620,963 A * | 4/1997 | Cook et al. .................... 514/44 |

FOREIGN PATENT DOCUMENTS

| | | |
|---|---|---|
| WO | WO 91/08313 | 6/1991 |
| WO | WO 92/20823 | 11/1992 |
| WO | WO 93/20101 | 10/1993 |
| WO | WO 94/29455 | 12/1994 |
| WO | WO 96/32496 | 10/1996 |
| WO | WO 96/34008 | 10/1996 |

OTHER PUBLICATIONS

Roberts and Caserio, Basic Principles of Organic Chemistry, W.A. Benjamin, Inc., New York (1965), at pp. 578–579.*

Dooley et al., Phosphorothioate Antisense Oligonucleotide to Protein Kinase C (PKC) Inhibit Proliferation In Rat C6 Glioma, Proceedings of the American Association For Cancer Research 35, 566 (Mar. 1994) (abstract No. 3375).*

Ahmad, et al., "Antisense Expression of Protein Kinase Cα Inhibits the Growth and Tumorigenicity of Human Glioblastoma Cells", *Neurosurg.*, 1994, 35, 904–909.

Alberts, et al., "Molecular Biology of the Cell", pp. 411–415, Garland Publishing, Inc., New York, 1983.

Bacher, et al., "Isolation and Characterization of PKC–L, A New member of the Protein Kinase C–Related Gene Family Specifically Expressed in Lung, Skin, and Heart", *Mol. Cell. Biol.*, 1991, 11, 126–133.

Ballester, et al., "Fate of Immunoprecipitable Protein Kinase C in $GH_3$ Cells Treated with Phorbol 12–Myristate 13–Acetate", *Biol. Chem.*, 1985, 260, 15194–15199.

Borek, et al., "Long–chain (sphingoid) bases inhibit multistage carcinogenesis in mouse C3H/10T1/2 cells treated with radiation and phorbol 12–myristate 13–acetate", *Proc. Natl. Acad. Sci. USA*, 1991, 88, 1953–1957.

Brigstock, et al., "Species–Specific High Molecular Weight Forms of Basic Fibroblast Growth Factor", 1990, 4, 45–52.

Brody and Frey, "Unambiguous determination of the sterochemistry of nucleotidyl transfer catalyzed by DNA polymerase I from escherichia coli", *Biochemistry*, 1981, 20, 1245–1252.

Brody and Frey, "Stereochemical course of nucleotidyl catalyzed by bacteriophage T7 induced DNA polymerase", *Biochemistry*, 1982, 21, 2570–2572.

Burgers and Esckstein, "A Study of the mechanism of DNA polymerase I from escherichia coli with diastereomeric phosphorothioate analogs of deoxyadenosine triphosphate", *J. Biol. Chem.*, 1979, 254, 6889–6893.

Burgers and Eckstein, "Absolute configuration of the diastereomers of adenosine 5'–O–(1–thiotriphosphate): Consequences for the stereochemistry of polymerization by DNA–dependent RNA polymerase from Escherichia coli", *Proc. Natl. Acad. Sci. USA*, 1978, 75, 4798–4800.

Cohen, J.S., Ed., Oligonucleotides: Antisense Inhibitors of Gene Expression, CRC Press, Inc., Boca Raton, FL, 1989.

Coussens, et al., "Multiple, Distinct Forms of Bovine and Human Protein Kinase C Suggest Diversity in Cellular Signaling Pathways", *Science*, 1986, 233, 859–866.

Crooke, et al., "Pharmacokinetic Properties of Several Novel Oligonucleotide Analogs in mice", *J. Pharmacol. Exp. Ther.*, 1996, 277, 923–937.

Cruse, et al., "Chiral Phosphorothioate Analogues of B–DNA", *J. Mol. Biol.*, 1986, 192, 891–905.

Dagle, et al., "Targeted degradation of mRNA in Xenopus oocytes and embryos directed by modified oligonucleotides: studies of An2 and cyclin in embryogenesis", *Nucleic Acids Research*, 1990, 18, 4751–4757.

Dagle, et al., "Pathways of Degradation and Mechanism of Action of Antisense Oligonucleotides in Xenopus laevis Embryos", *Antisense Research and Development*, 1991, 1, 11–20.

Dagle, et al., "Physical properties of oligonucleotides containing phosphoramidate–modified internucleoside linkages", *Nucleic Acids Research*, 1991, 19, 1805–1810.

DeVirgilio, et al., "Cloning and Disruption of a Gene Required for Growth on Acetate but not on Ethanol: the Acetyl–Coenzyme A Synthetase Gene of Saccharomyces cerevisiae", *Yeast*, 1992, 8, 1043–1051.

Eckstein and Jovin, "Assignment of Resonances in the Phosphorus–31 Nuclear Magnetic Resonance Spectrum of Poly[d(A–T)] from Phosphorothioate Substitution", *Biochemistry*, 1983, 2, 4546–4550.

Eder, P.S. and Walder, J.A., "Ribonuclease H from K562 Human Erythroleukemia Cells", *J. Biol. Chem.*, 1991, 266, 6472–6479.

Endo, et al., "Cell Membrane Signaling as Target in Cancer Therapy: Inhibitory Effect of N,N–Dimethyl and N,N,N–Trimethyl Sphingosine Derivatives on In Vitro and In Vitro Growth of Human Tumor Cells in Nude Mice", *Cancer Research*, 1991, 51, 1613–1618.

Ettinger, L., et al., "Intrathecal Methotrexate Overdose Without Neurotoxicity", *Cancer*, 1978, 41, 1270–1273.

French, et al., "Expression of Two Related Nonstructural Proteins of bluetongue Virus (BTV) Type 10 in Insect Cells by a Recombinantbaculovirus: Production of Polyclonal Ascitic Fluid and Characterization of the Gene Product in BTV–Infected BHK Cells", *J. Virol.*, 1989, 63, 3270–3278.

Gao, et al., "Cloning and Characterization of Mouse Gene with Homology to the Human von Hippel–Lindau Disease Tumor Suppressor Gene: Implications for the Potential Organization of the Human von Hippel–Lindau Disease Gene", *Cancer Res.*, 1995, 55, 743–747.

Gebeyehu, G., et al., "Novel biotinylated nucleotide–analogs for labeling and colorimetric detection of DNA", *Nucleic Acid Res.*, 1987, 15, 4513–4534.

Gelbert, et al., "Analysis of GPT Activity in Mammalian Cells with a Chromosomally Integrated Shuttle Vector Containing Altered gpt Genes", *Somat. Cell. Mol. Genet.*, 1990, 16, 173–184.

Gescher, et al., "Protein Kinase C—A Novel Target for Rational Anti–Cancer Drug Design", *Anti–Cancer Drug Design*, 1989, 4, 93–105.

Godson, et al., "Inhibition of Expression of Protein Kinase C α by Antisense cDNA Inhibits Phorbol Ester–Mediated Archidonate Release", *J. Biol. Chem.*, 1993, 268, 11946–11950.

Gold and Stormo in: "Translational Initiation", Department of Molecular, Cellular and Developmental Biol., 1987, vol. 2, Chapter 78, pp. 1302–1307.

Greenberg, M.E. in Current Protocols in Molecular Biology, F.M., Ausubel, et al., Eds., John Wiley & Sons, NY 1987.

Gupta, et al., "Template–Primer–dependent Turnover of (Sp)–dATPαS by T4 DNA Polymerase", *J. Biol. Chem.*, 1982, 257, 7689–7692.

Hegemann, L. and G. Mahrle, "Pharmacology of the Skin", H. Mukhtar, ed., pp. 357–368, CRC Press, Boca Raton, FL, 1992.

Henthorn, P., et al., "Expression of a human placental alkaline phosphatase gene in transfected cells: use as a reporter for studies of gene expression", *Proc. Natl. Acad. Sci. USA*, 1988, 85, 6342–6346.

Hidaka and Hagiwara, "Pharmacology of the isoquinoline sulfonamide protein kinase C inhibitors", *Trends in Pharm. Sci.*, 1987, 8, 162–164.

Kabanov, et al., "A new class of antivirals: antisense oligonucleotides combined with a hydrophobic substituent effectively inhibit influenza virus reproduction and synthesis of virus–specific proteins in MDCK cells", *FEBS Lett.*, 1990, 259, 327–330.

Kanagasundaram, V. And Scopes, R., "Isolation and characterization of a gene encoding gluconolactonase from Zymomonas mobilis", *Biochim. et Biophys. Acta*, 1992, 1171, 198–200.

Kornberg, A., DNA Replication, pp. 75–77, W.H. Freeman & Co., San Francisco, 1980.

Krug, et al., "Evidence for increased synthesis as well as increased degradation of protein kinase C after treatment of huma ostersarcoma cells with phorbol ester", *J. Biol. Chem.*, 1987, 262, 11852–11856.

Kubo, et al., "Primary structures of human protein kinase CBI and BII differ only in their C–terminal sequences", *FEBS Lett.*, 1987, 223(1), 138–142.

Letsinger, et al., "Cholesterol–conjugated oligonucleotides: Synthesis, properties and activity as inhibitors of replication of human immunodeficiency virus in cell culture", *Proc. Natl. Acad. Sci. USA*, 1989, 86, 6553–6556.

Ludwig and Eckstein, "Rapid and efficient synthesis of nucleoside 5'–O–(1–thiotriphosphates), 5'–triphosphates and 2',3'–cyclophosphorothioates using 2–chloro–4H–1,3, 2–benzodioxaphosphorin–4–one", *J. Org. Chem.*, 1989, 54, 631–635.

Luer and Hatton, "Vancomycin Administration into the Cerebrospinal Fluid: A Review", *The Annals of Pharmacotherapy*, 1993, 27, 912–921.

Manoharan, et al., "Introduction of a Lipophilic Thioether Tether in the Minor Groove of Nucleic Acids for Antisense Applications", *Bioorg. Med. Chem. Lett.*, 1993, 3, 2765–2770.

Manoharan, et al., "Chemical Modfications to Improve Uptake and Bioavailability of Antisense Oligonucleotides", *Ann. N.Y. Acad. Sci.*, 1992, 660, 306–309.

Manoharan, et al., "Cholic Acid–Oligonucleotide Conjugates for Antisense Applications", *Bioorg. Med. Chem. Lett.*, 1994, 4, 1053–1060.

Manoharan, et al., "Lipidic Nucleic Acids", *Tetrahedron Lett.*, 1995, 36, 3651–3654.

Manoharan, et al., "Oligonucleotide Conjugates: Alteration of the Pharmacokinetic Properties of Antisense Agents", *Nucleosides & Nucleotides*, 1995, 14, 969–973.

Markussen, et al., "Translational control of oskar generates Short OSK, the isoform that induces poly plasm assembly", *Development*, 1995, 121, 3723–3732.

Martin, et al., "Ein neuer Zagang zu 2'–O–Alkylribonucleosiden und Eigenschaften deren Oligonucleotide", *Helv. Chim. Acta*, 1995, 78, 486–504.

The Merck Manual of Diagnosis and Therapy, 15th Ed., pp. 1206–1228, Berkow, et al., eds., 1987, Rahay, N.J., 1987.

McDermott, et al., "Structure and lens expression of the gene encoding chicken βA3/A1–crystallin", *Gene*, 1992, 117, 193–200.

Minshull and Hunt, "The use of single–stranded DNA and RNase H to promote quantitative 'hybrid arrest of translations' of mRNA/DNA hybrids in reticulocyte lysate cell-free translation", *Nucl. Acid Res.*, 1986, 14, 6433–6451.

Mishra, et al., "Improved leishmanicidal effect of phosphorothioate antisense oligonucleotides by LDL–mediated delivery", *Biochim. Biophys. Acta*, 1995, 1264, 229–237.

Monaco, et al., "Structure of Two Rat Genes Coding for Closely Related Rolipram–sensitive cAMP Phosphodiesterases", *J. Biol. Chem.*, 1995, 269, 347–357.

Nielsen, et al., "Sequence–Selective Recognition of DNA by Strand Displacement with a Thymine–Substituted Polyamide", *Science*, 1991, 254, 1497–1500.

Nishizuka, et al., "The Molecular Heterogeneity of Protein Kinase C and its Implications for Cellular Regulation", *Nature*, 1988, 334, 661–665.

Oberhauser, et al., "Effective incorporation of 2'–O–methyl–oligoribonucleotides into liposomes and enhanced cell association through modification with thiocholesterol", *Nucl. Acids Res.*, 1992, 20, 533–538.

Olsen, et al., "Inhibition of Protein Kinase–A by Overexpression of the Cloned Human Protein Kinase Inhibitor", *Mol. Endocrinol.*, 1991, 5, 1246–1256.

Osada, et al., "A phorbol ester receptor–protein kinase, nPKCη, a new member of the protein kinase C family predominantly expressed in lung and skin", *J. Biol. Chem.*, 1990, 265, 22434–22440.

Parker, et al., "The complete primary structure of protein kinase c—the major phorbol ester receptor", *Science*, 1986, 233, 853–866.

Perri, et al., "Interactions of Plasmid–encoded Replication Initiation Proteins with the Origin of DNA Replication in the Broad Host Range Plasmid RK2", *J. Biol. Chem.*, 1991, 266, 12536–12543.

Pushpa–Rekha, et al., "Rat Phospholipid–hydroperoxide Glutathione Peroxidase", *J. Biol. Chem.*, 1995, 270, 26993–26999.

Rogers, et al., "Alternative splicing dictates translational start in Epstein–Barr virus transcripts", *EMBO J.*, 1990, 9, 2273–2277.

Romaniuk and Eckstein, "A study of the mechanism of t4 DNA polymerase with diasteromeric phosphorothioate analogues of deoxyadenosine triphosphate", 1982, J. Biol. Chem., 257(13), 7684–7688.

Saison–Behmoaras, et al., "Short modified antisense oligonucleotides directed against Ha–ras point mutation induce selective cleavage of the mRNA and inhibit T24 cells proliferation", *EMBO J.*, 1991, 10, 1111–1118.

Sambrook, et al., Molecular Cloning. A Laboratory Manual., vol. 2, Cold Spring Harbor Laboratory Press, Cold Spring Harbor, N.Y., p. 10.59, 1989.

Saul, et al., "celB, a Gene Coding for a Bifunctional Cellulase from the Extreme Thermophile *Caldocellum saccharolyticum*", *Appl. Environ. Microbiol.*, 1990, 56, 3117–3124.

Shea, et al., "Synthesis, hybridization properties and antiviral activity of lipid–oligodeoxynucleotide conjugates", *Nucl. Acids Res.*, 1990, 18, 3777–3783.

Stec, J.W., Oligonucleotides as Antisense Inhibitors of Gene Expression: Therapeutic Implications, Meeting Abstracts, Jun. 18–21, 1989.

Stec, et al., "Novel Route to Oligo(Deoxyribonucleoside Phosphorothioates). Stereocontrolled Synthesis of P–chiral Oligo(Deoxyribonucleoside Phosphorothioates)", Nucleic Acids Res., 1991, 19, 5883–5888.

Stec and Lesnikowski, "Stereospecific Synthesis of P–Chiral Analogs of Oligonucleotides", in "Methods in Molecular Biology", S. Agrawal, Ed., 1993, 20, 285–313.

Stec, et al., "Reversed–phase High–performance Liquid Chromatographic Separation of Diastereomeric Phosphorothioate Analogues of Oligodeoxyribonucleotides and Other Backbone–Modified Congerers of DNA" *Chromatography*, 1985, 326, 263–280.

Svinarchuk, et al., "Inhibition of HIV proliferation in MT–4 cells by antisense oligonucleotide conjugated to lipophilic groups", *Biochimie*, 1993, 75, 49–54.

Ueda, et al., "Phosphorothioate–containing RNAs show mRNA activity in the prokaryotic translation systems in vitro", *Nucl. Acids Research*, 1991, 19, 547–552.

Weinstein, I.B., "Cancer Prevention: Recent Progress and Future Opportunities", Cancer Res. Suppl., 1991, 51, 5080s–5085s.

Yaoita, et al., "*Xenopus laevis* α and β thyroid hormone receptors", *Proc. Natl. Acad. Sci. USA*, 1990, 87, 7090–7094.

Young, S., et al., "Down–regulation of protein kinase C is due to an increased rate of degradation", *Biochem. J.*, 1987, 244, 776–779.

Zimm, S., et al., "Cerebrospinal Fluid Pharmacokinetics of Intraventricular and Intravenous Aziridinylbenzoquinone", *Cancer Research*, 1984, 44, 1698–1701.

Bryant, F. and Benkovic, S., "Stereochemical course of the reaction catalyzed by 5'–nucleotide phosphodiesterase from snake venom", *Biochemistry*, 1979, 2825–2628.

Eckstein, F. And Jovin, T.M., "Nucleoside Phosphorothioates", *J. Am. Chem. Soc.*, 1966, 88, 4292.

Eckstein, F., "Nucleoside Phosphorothioates", *J. Am. Chem. Soc.*, 1970, 92, 4718–4723.

Doerr and Fox, "Nucleosides. XL. The Introduction of a 2,3'–Imino Bridge into Pyrimidine Nucleosides", *J. Am. Chem.*, 1967, 89, 1760–1761.

Haga, K., et al., "The preparation of halo–nucleosides", *Bull. Of the Chem. Soc. Jpn.*, 1970, 43, 3922–3924.

Fuji, et al., "Acylphosphonates. 7.[1] A New Method for Stereospecific and Stereoselective Generation of Dideoxyribonucleoside Phosphorothioates via the Acylphosphone Intermediates", *Tetrahedron*, 1987, 43, 3395–3407.

Gupta, et al., "Template–Primer–Dependent Turnover of (Sp)–dATP S by T4 DNA Polymerase", *J. Bio. Chem.*, 1982, 247, 7689–7692.

Goodchild, "Conjugates of Oligonucleotides and Modified Oligonucleotides: A Review of Their Synthesis and Properties", *Bioconjugate Chem.*, 1990, 1, 166–187.

Koole, L.H., et al., "Enhanced stability of a Watson & Crick DNA duplex structure by methylation of the phosphate groups in one strand", *Proc. K. Ned. Acad. Wet.*, 1987, 90(1), 41–46.

Jager, A., et al., "Oligonucleotide N–alkylphosphoramidates: Synthesis and binding to polynucleotides", *Biochemistry*, 1988, 27, 7237–7246.

Holy, A. And Storm, F., "Oligonucleotidic compounds. XXXII. Phosphorylation of 1–lyxofuranosyl, 1–xylofuranosyl and 1–arabinofuranosyl derivatives of uracil and thymine with thriethyl hosphite and hexachloroacetone", *Collection Czechoslov., Chem. Commun.*, 1969, 34, 1929–1953.

Holy A., "Nucleic acid components and their analogues. IC. synthesis of 6–azauridine 5'–methanephosphonate and 6–azauridine 2'(3')–methanephosphonate", *Collection Czechoslov. Chem. Commun.*, 1967, 32, 3713–3718.

Lee, W.W., et al., "Xylo–and Arabinofuranosylthioguanine and Related Nucleosides Derived form 2–Acetamido–6–chloropurine", *J. Of Medicinal Chem.*, 1971, 14, 820–823.

Ikehara, et al., "Purine Cyclonucleosides–8 Selective Sulfonylation of 8–Bromoadenosine Derivatives and an Alternate Synthesis of 8,2'–and 8,3'–S–Cyclonucleosides", *Tetrahedron*, 1970, 26, 4251–4259.

Kondo, K., et al., "Studies on biologically active nucleosides and nucleotides.3. synthesis of 9–(3–bromo–3–deoxy–2, 5–di–O–acetyl–B–D–xylofuranosyl) adenine", *J. Org. Chem.*, 1977, 42(24), 3967–3968.

Goodman, L. And Hubert–Habart, M., "The Direct Formation of a 3',5'–Cyclic Mononucleotide from an Adenine Nucleoside", *Chem. Commun.*, 1969, 740–741.

Letters, R., et al., "$O^2$,3'–Cyclouridine", *J. Chem. Soc.*, 1961, 1410–1413.

Lichtenthaler, F.W., et al., Chem. Ber., 1969, 102, 964.

Niewiarowski, W., et al., "Diastereomers of Thymidine 3'O–(Methanephosphono–thioate): Synthesis, Absolute Configuration and Reaction with 3'–methoxyacetylthymidine Under Conditions of Triester Approach to Oligonucleotide Synthesis", *Acta Bioichimica Polonica*, 1987, 34, 217–231.

Scheit, Karl Heinz, "Nucleotides with Modified Phosphate Groups", in Nucleotide Analogs John Wiley & Sons, 1980, Chapter Four and Chapter Six.

Suzaki, et al., "Synthesis of 9–β–D–Xylofuranosyl–6–mercaptopurine and 9–β–D–Xylofuranosylfuanine 5'–Phosphate", Chem. Pharm. Bull., 1970, 18, 172–176.

Marmuto, R., et al., "One–Step Halogenation at the 2'–Position of Uridine, and Related Reactions of Cytidine and N'–Acetylcytidine", Pharm. Bull., 1974, 22, 128–134.

Mizuno, Y., et al., "Syntheses of Potential Antimetabolites. XV. Syntheses of a Sulfonate Analog of Adensine 5'–Phosphate and an Alternative Synthesis of 5',8–S–Anhydroadenine Nucleosides and 5'–Deoxyspongoadenosine and Its Isomers", J. Org. Chem., 1974, 39, 1440–1444.

Reese, "The Chemical Synthesis of Oligo– and Polynucleotides by the Phosphotriester Approach", Tetrahedron, 1978, 34, 3143–3179.

Robins, et al., "Nucleic acid related compounds. 11. adenosine 2',3'–ribo–epoxide. synthesis, intromolecular degradation, and transformation into 3'–substituted xylofuranosyl nucleosides and the lyxo–epoxide$^{1,2}$", J. Org. Chem., 1974, 39(11), 1564–1570.

Miller, P.S., et al., "Biochemical and Biological Effects of Nonionic Nucleic Acid Methylphosphonates", Biochemistry, 1981, 20, 1874–1880.

Uhlmann, E. And Peyman, A., "Antisense oligonucleotides: A new therapeutic principle", Chemical Reviews, 1990, 90(4), 578–584.

Murray, A.W., et al., "Adenosine 5'–Phosphorothioate. A Nucleotide Analog That is a Sustrate, Competitive Inhibitor, or Regulator of Some Enzymes That Interact with Adensoine 5'–Phosphate", Biochemistry, 1968, 4023–4029.

Mizuno, Y., et al., "A Novel Synthesis of Purine β–D–Nucleosides via Purine 8,5'–S–Anhydronucleosides", J. Am. Chem. Soc., 1972, 94, 4737–4739.

Miller, N., et al., "Nucleosides. XXI. Synthesis of Some 3'–Substituted 2',3'–Dideoxyribonucleosides of Thymine and 5–Methylcytosine", J. Org. Chem., 1964, 29, 1772–1776.

Szarek, et al., "Synthesis of 5–Deoxy–D–xylo–Hexose and 5–Deoxy–L–arabino–Hexose, and Their Conversion into Adenine Nucleosides", Carbohydrate Res., 1978, 62, 89–103.

Schuman, D., et al., J. Am. Chem. Soc., 1970, 92, 3434.

Reist, et al., "Synthesis of 9–(5–Deoxy–B–D–arabinofuranosyl) adenine", J. Org. Chem., 1965, 30, 3401–3403.

Wiberg, "Physical Organic Chemistry", John Wiley & Sons, New York, 1964, p. 424.

Letsinger, et al., "Effects of pendant groups at phosphorus on binding properties of d–ApA analogues", Nucleic Acids Res., 1986, 14, 3487–3499.

Wempen, I. And Fox, "Nucleosides. LV. Synthesis of a sulfur–bridged thymine anhydro nucleoside and derivatives", J. Org. Chem., 1969, 34, 1020–1025.

Wijnen, M.H., "Disproportionation and Recombination Reactions of Methyl and n–Pentyl Radicals", J. Am. Chem. Soc., 1961, 83, 3752–3754.

Cohen, J. "Oligonucleotides Inhibitors of Gene Expression", CRC Press, Boca Raton, FL, 1989, pp. 7–116, 137–210.

Guga, P. And Okruszek, A., "Stereospecific conversion of p–chiral nucleoside phosphorothioates", Tetrahedron Letters, 1984, 25, 2897–2900.

Jarvest, R.L. and Lowe, G., "Synthesis of methyl (R) and (S)–[$^{18}$O]phosporothioates and determination of the absolute configuration at phosphorus of the diastereoisomers of adenosine 5'–(1–thiotriphosphate)", J.C.S. Chem. Comm., 1979, 364–366.

Lee, Choongeun and Suhadolnik, Robert J., "2',5'–Oligoadenylates Chiral at Phosphorus: Enzymatic Synthesis, Properties, and Biological Activities of 2',5'–Phosphorothioate Trimer and Tetramer Analogues Synthesized from (Sp)–ATPαS", Biochemistry, 1985, 24(3), 551–555.

Lesnikowski, et al., "Octa(thymidine methanephosphonates) of partially defined stereochemistry: synthesis and effect of chirality at phosphorous on binding to pentadecadeoxyriboadenylic acid", Nucleic Acids Res., 1990, 18(8), 2109–2115.

Richard, J.P. and Frey, P.A., "Stereochemical course of phosphoanhydride synthesis", J. Am. Chem. Soc., 1983, 105, 6605–6609.

Sammons, R. Douglas and Frey, Perry A., "Synthesis of $R_p$ and $S_p$[α–$^{18}$O]ADP from $S_p$ and $R_p$ β–Cyanoethyl–Adenosine 5'–[1–Thiodiphosphate]", J. Biol. Chem., 1982, 257(3), 1138–1141.

Sopchik, et al., "$^{17}$O NMR of diastereomeric 3',5'–Cyclic Thymidine Methyl hosphates, Methylphosphonates, and N,N–Dimethyl phosphoramidates. Phosphorus Configuration of P–Chiral [$^{17}$O, $^{18}$O]–Nucleoside Phosphate Diesters", Tetrahedron Letters, 1989, 30(10), 1221–1224.

Stec, et al., "Synthesis and Absolute Configuration of P–Chiral O–Isopropyl Oligonucleotide Triesters", Tetrahedron Letters, 1985, 26(18), 2191–2194.

Stec, et al., "Solid–Phase Synthesis, Separtion, and Stereochemical Aspects of P–Chiral Methane–and 4,4'–Dimethoxytriphenylmethanephosphonate Analogs of Oligodeoxyribonucleotides", J. Org. Chem., 1985, 50(20), 3908–3913.

Van Pelt, Jean E., et al., "Gentamicin Nucleotidyltransferase; Stereochemical Inversion at Phosphorus in Enzymatic 2'–Deoxyadenyl Transfer to Tobramycin", J. Biol. Chem., 1986, 261(34), 15994–15999.

Tsai, M.D., "Stereochemistry of the hydrolysis of adenosine 5'–thiophosphate catalyzed by venom 5'–nucleotidase", Biochemistry, 1980, 19, 5130–5316.

Ludwig, J. And Eckstein, F., "Rapid and efficient synthesis of nucleoside 5'–O–(1–thiotriphosphates), 5'–triphosphates and 2',3'–cyclophosphorohioates using 2–chloro–4H–1,3, 2–benzodioxzphosphorin–4–one", J. Org. Chem., 1989, 54, 631–635.

Rothenberg, et al., "Oligodeoxynucleotides as anti–sense inhibitors of gene expression: therapeutic implication", National Cancer Institute, 1989, 81(20), 1539–1565.

Agrawal, S., et al., "Oligodeoxynucleoside Phosphoramidates and Phosphorothioates as Inhibitors of Human Immunodeficiency Virus", PNAS USA, 1988, 85, 7079–7083.

Marcus–Sekura, C.J., et al., "Comparative inhibition of chloramphenicol acetyltrasferase gene expression by anti-sense oligonucleotide analogues having alkyl phosphotriester, methylphosphonate and phosphorothioate linkages", Nucleic Acids Research, 1987, 15, 5749–5763.

Follman, H. And Hogenkamp, "Interaction of Ribonucleotide Reductase with Ribonucleotide Analogs", Biochemistry, 1971, 10, 186–187.

Seela, F., et al., "Phosphoramidites of (oxygen–18) Chiral (Rp)–and (Sp)–configurated Dimer–blocks and their use in Automated Oligonucleotide Synthesis", *Nucleosides and Nucleotides*, 1987, 6(1–2), 451–456.

Borovsky, D., "Isolation and Characterization of Highly Purified Mosquito Oostatic Hormone", *Archives of Insect Biochem. And Physiol.*, 1985, 2, 333–349.

Borovsky, D., "Oostatic Hormone Inhibits Biosynthesis of Midgut Proteplytic Enzymes and Egg Development in Mosquitoes", *Archives of Insect Biochemistry and Physiol.*, 1988, 7, 187–210.

Borovsky, D., "Mosquito oostatic factor: a novel decapeptide modulating trypsin–like enzyme biosynthesis in the midgut", *FASEB*, 1990, 4, 3015–3020.

Borovsky, D., et al., "Development of Specific RIA and ELISA to Study Trypsin Modulating Oostatic Factor in Mosquitoes", *Archives of Insect Biochem. and Physiol.*, 1992, 21, 13–21.

Rayne, R.C., and O'Shea, M., "Inactivation of Neuropeptide Hormones (AKH 1 and AAKH II) Studies In Vivo and In Vitro", *Insect Biochem. Molec. Biol.*, 1992, 22(1), 25–34.

Charbonneau, Harry, "Strategies for Obtaining Partial Amino Acid Sequence Data from Small Quantities (>5nmol) of Pure of Partially Purified Protein", A Practical Guide to Protein and peptide purification for Microsequencing, pp. 15–30.

Sober, H.A., (1968), "Handbook of Biochemistry", The Chemical Rubber Co., Cleveland, Ohio, p. C70.

Baxter, et al., "PKC–episilon is involved in granulocyte–macrophage colong–stimulating facto signal transduction: Evidence from microphysiometry and antisense oligonucleotide experiments", *Biochemistry*, 1992, 31, 10950–10954.

Brandt, et al., "Districk Patterns of Expression of Different Protein Kinase CmRNA's in Rat Tissues", *Cell.*, 1987, 49, 57–63.

Farese, et al., "Antisense DNA downregulates protein kinase C isozymes (beta and alpha) and insulin–stimulated 2–deoxyglucose uptake in rat adipocytes", *Antisense Res. Dev.*, 1(1), 1991, 35–42.

Finkenzeller, G., "Sequence of Human Protein Kinase C α", *Nucleic Acids Research*, 1990, 18, 2183.

Hackh's Chemical Dictionary, Grant, et al. (Ed.), McGraw–Hill Book Company, New York, p. 312.

Maister, Bioworld Today, Apr. 29, 1994, p. 3.

Standaert, et al., 1991, Cellular Biochem. (Keystone Symposia on Molecular and Cellular Biology, Jan. 18–25), Suppl. 15B, p. 26, abstract CA 211.

Maier, et al., "An oligomer targeted against protein kinase C alpha prevents interleukin–1 alpha indiction of cycloxygenase expression in human endothelial cells", *Exp. Cell. Res.*, 1993, 205(1), 52–58.

Marcus–Sekura, "Techniques for Using Antisense Oligodeoxyribonucleotides to Study Gene Expression", *Analytical Biochemistry*, 1988, 172, 289–295.

Sakanou, Youichirou, et al., "Protein Kinase C Activity as Marker for Colorectal Cancer", *Int. J. Cancer*, 1991, 48, 803–806.

Simons, et al., "Antisense c–myb oligonucleotides inhibit intimal arterial smooth muscle cell accumulation in vivo", 1992, 359, 67–70.

1993 Catalog of Products for DNA Research, Glen Research, Sterling, VA, p. 21.

Watson, et al, 1987, in Molecular Biology of the Gene, fourth edition, Benjamin/Cummings Publishing Company, Menlo Park, CA, p. 241.

Webster's II New Riverside University Dictionary Soukkhanov, et al., (eds.) 1984, Houghton Mifflin Company, Boston, MA, p. 68.

Zon, "Oligonucleotide analogues as Potential Chemotherapeutic Agents", *Pharmaceuticals Res.*, 1988, 5, 539–549.

Ono, et al., "The structure, expression and properties of additional members of the protein kinase C family", *J. Biol. Chem.*, 1988, 263(14), 6927–6932.

Kawasaki, et al., "Synthesis and Biophysical Studies of 2'–dRIBO–2'–F Modified Oligonucleotides", Conference on Nucleic Acid Therapeutics, Clearwater, FL, Jan., 1991.

Daluge and Vince, "Synthesis and Antimicrobial Activity of a Carbocyclic Puromycin Analog.6–Dimethyamino–9–{R–[2Rhydroxy–3R–(p–methoxyphenyl–L–alanylamino)]–cyclopentyl}purine", *Journal of Medicinal Chem.*, 1971, 15, 171–177.

Ikehara, et al., "Recognition by Restriction Endonuclease EcoRI of Deoxyoctanucleotides Containing Modified Sugar Moieties", *European Journal of Biochemistry*, 1984, 139, 447–450.

Ikehara, et al., "A Linear Relationship Between Electronegativity of 2'–Substituents and Conformation of Adenine Nucleosides", *Tetrahedron Letters*, 1979, 42, 4073–4076.

Ikehara, et al., "Polynucleotides. LII.synthesis and properties of poly(2'–deox–2'–fluoroadenylic acid)" *Nucleic Acids Research*, 1978, 5, 1877–1887.

Ikehara, et al., "Polynucleotides. LVI. Synthesis and Properties of Poly(2'–deoxy–2'–fluoroinosinic Acid)" *Nucleic Acids Research*, 1978, 5, 3315–3324.

Ikehara, et al., "Polynucleotides. L. Synthesis and properties of poly(2'–chloro–2'–deoxyadenylic acid) and poly (2'–bromo–2'–deoxyadenylic acid)", *Nucleic Acids Research*, 1977, 4, 4249–4260.

Eckstein, et al., "Polynucleotides Containing 2'–Chloro–2'–Deoxyribose", *Biochemistry*, 1972, 11, 4336–4344.

Inoue, et al., "Synthesis and hybridization studies on two complementary nona(2'–O–methyl) ribonucleotides", *Nucleic Acids Research*, 1987, 15, 6131–6148.

Shibahara, et al., "Inhibition of Human Immunodeficiency Virus (HIV–1) Replication by Synthetic Oligo–RNA Derivatives", *Nucleic Acids Research*, 1987, 17, 239–252.

Guschlbauer, et al., "Nucleoside conformation is Determined by the Electronegativity of the Sugar Substituent", *Nucleic Acids Research*, 1980, 8, 1421 (abstract).

Stein, C.A. and Cohen, J.S., "Oligonucleotides as Inhibitors of Gene Expression", *Cancer Research*, 1988, 48, 2659–2668.

Walder, J., "Antisense DNA and RNA: progress and prospects", *Genes & Develop.*, 1988, 2, 502–504.

Zon, G., "Synthesis of backbone–modified DNA analogues for biological applications", *J. Protein Chem.*, 1987, 6, 131–145.

Van der Krol, A.R., et al., "Modulation of Eukaryotic Gene Expression by Complementary RNA or DNA Sequences", *BioTechniques*, 1988, 6, 958–973.

Loose–Mitchell, D.S., "Antisense Nucleic Acids as a Potential Class of Pharmaceutical Agents", *TIPS*, 1988, 9, 45–47.

Miller, P.S., et al., "A New Approach to Chemotherapy Based on Molecular Biology and Nucleic Acid Chemistry: Mtagen (Masking Tape for Gene Expression)" *Anti–Cancer Drug Design*, 1987, 2, 117–128.

Walder, R.Y. and Walder, J.A., "Role of RNase H in hybrid–arrested translation by antisense oligonucleotides", *Proc. Natl. Acad. Sci. USA*, 1988, 85, 5011–5015.

Stein, C.A., et al., "Physiochemical Properties of Phosphorothioate Oligodeoxynucleotides", *Nucleic Acids Research*, 1988, 16, 3209–3221.

Agarwal, et al., "Synthesis and Enzymatic Properties of Deoxyribooligonucleotides Containing Methyl and Phenylphosphonate Linkages", *Nucleic Acids Research*, 1979, 6, 3009–3024.

Miller, P.S., et al., "Nonionic Nucleic Acid Analogues. Synthesis and Characterization of Dideoxyribonucleoside Methylphosphonates", *Biochemistry*, 1979, 18, 5134–5143.

Jayaraman, K.., "Selective inhibition of escherichia coli protein synthesis and growth by nonionic oligonucleotides complementary to the 3'end of 16S rRNA", *Proc. of the Nat. Acad. Sci. USA*, 1981, 78, 1537–1541.

Miller, P.S., et al., "Synthesis and properties of adenine and thymine nucleoside alkyl phospotriesters, the neutral anlogs of dinucleoside monophosphates", *J. Am. Chem. Soc.*, 1971, 93, 6657–6665.

Agris, C.H., et al., "Inhibition of Vesicular Stomatitis Virus Protein Synthesis and Infection by Sequence–Specific Oligodeoxyribonucleoside Methylphosphonates", *Biochemistry*, 1986, 25, 6268–6275.

Smith, C.C., et al., "Antiviral effect of an oligo(nucleoside methylphosphonate)complementary to the splice junction of herpes simplex virus type 1 immediate early pre–mRNAs 4 and 5", *Proc. Natl. Acad. Sci. USA*, 1986, 83, 2787–2791.

Ruby, S.W., et al., "An early hierarchic role of U1 small nuclear ribonucleoprotein in splicesome assembly", *Science*, 1988, 242, 1028–1035.

Tidd, D.M., et al., "Evaluation of N–ras oncogene anti-–sense, sense and nonsense sequence methylphosphonate oligonucleotide analogues", *Anti–Cancer Drug Design*, 1988, 3, 117–127.

HCPF Roelen, et al., "Synthesis of nucleic acid methylphos–phonothilates", *Nucleic Acid Research*, 1988, 16, 7633–7645.

Agarwal, et al., "Oligodeoxynucleoside Phosphormaidtes and Phosphorothioates as Inhibitors of Human Immunodeficiency Virus", *Proc. Natl. Acad. Sci. USA*, 1988, 85, 7079–7083.

Matsukura, M., et al., "Phosphorothioate analogs of oligodeoxynucleotides: Inhibitors of replication and cytopathic effects of human immundeficiency virus", *Proc. Acad. Sci. USA*, 1987, 84, 7706–7710.

Brill, W.K.D., et al., "Synthesis of oligodeoxynucleoside phosphorodithioates via thioamidites", *J. Am. Chem. Soc.*, 1989, 111, 2321–2322.

Jager, A., et al., "Oligonucleotide N–alkylphosphoramidates: Synthesis and binding to polynucleotides", *Biochemistry*, 1988, 27, 7237–7246.

Cazenave, et al., "Enzymatic amplification of translation inhibition of rabbit α–globin mRNA mediated by anti–messenger oligodeoxynucleotides covalently linked to intercalating agents", *Nucleic Acid Research*, 1987, 15, 4717–4736.

Constant, J.F., et al., "Heterodimeric Molecules Including Nucleic Acid Bases and 9–Aminoacridine Spectroscopic Studies", *Biochemistry*, 1988, 27, 3997–4003.

Yeung, A.T., et al., "Photoreactives and thermal properties of psoralen cross–links", *Biochemistry*, 1988, 27, 3204–3210.

Meyer, R.B., "Efficient, Specific Cross–Linking and Cleavage of DNA by Stable, Synthetic Complementary Oligodeoxynucleotides", *J. Am. Chem. Soc.*, 1989, 111, 8517–8519.

Knorre, D.G. and Vlassov, V.V., "Complementary–addressed (sequence–specific) modification of nucleic acids", *Progress in Nucleic Acid Res. & Mol. Biol.*, 1985, 32, 291–320.

Doan, P.L., et al., Nucleic Acids Res., 1987, 15, 8643–8659.

Sigman, D.S., "Nuclease Activity of 1,10–Phenanthroline–Copper Ion", *Accts. Chem. Res.*, 1986, 19, 180–186.

Dreyer, G.B. and Dervan, P.B., "Sequence–specific cleavage of single stranded DNA: Oligodeoxynucleotide–EDTA–Fe(II)", *Proc. Natl Acad. Sci. USA*, 1985, 82, 968–972.

The Chemistry of Heterocyclic Compounds, A. Weissberger, Ed., Imidazole and Derivatives, Part 1, Interscience, N.Y., 1953.

Biggadike, et al., "Short convergent route to homochiral carbocyclic 2'–deoxynucleosides and carbocyclic robonucleosides", *J. Chem. Soc., Chem. Commun.*, 1987, 1083–1084.

Outten, R.O., and Daves, D., Jr., "Synthetic 1–methoxy–benzo[d]naphtho[1,2–b]pyran–6–one c–glycosides", *J. Org. Chem.*, 1987, 52, 5064–5066.

Kazimierczuk, Z., et al., "Synthesis of 2–deoxytubercidin, 2'–deoxyadenosine, and related 2'–deoxynucleosides via novel direct stereospecific sodium salt glycosylation procedure", *J. Am. Chem. Soc.*, 1984, 106, 6379–6382.

Revankar, et al., "Synthesis and Antiviral/Antitumor of Certain 3–Seazaguanine Nucleosides and Nucleotides", *J. Med. Chem.*, 1984, 27, 1389–1396.

Stufkens, D.J., "Dynamic Jahn–Teller Effect in the Excited States of $SeCl_6^{2-}$, $SeBr_6^{2-}$, $TeCl_6^{2-}$ and $TeBr_6^{2-}$", *Rec. Trav. Chim.*, 1970, 89, 1185–1201.

Castle, et al., "Imidazol[4,5–D]pyridazines. I. Synthesis of 4,7–disubstituted derivatives", *J. Org. Chem.*, 1958, 23, 1534–1538.

Nucleic Acid Chemistry, Improved and New Synthetic Procedures, Methods and Techniques, Part 3, p. 229, 1986.

Suciu, et al., "Synthesis of 9–(2, 5–dideoxy–β–D–glycero–pent–4–enofuranosyl)adenine", *Carbohydr. Res.*, 1975, 44, 112–115.

Jones, R. A., in Oligonucleotide Synthesis—A Practical Approach, M.J. Gait, Ed., IRL Press, Washington, D.C. 1985.

Robins, M.J., et al., "Nucleic acid related compounds. 46. A general procedure for the efficient deoxygenation of secondary alcohols. regiospecific and stereoselective conversion of ribonucleosides to 2'–deoxynucleosides", *J. Am. Chem. Soc.*, 1983, 105, 4059–4065.

Jones, G., "4'–substituted nucleosides. 5. Hydroxymethylation of nucleoside 5'–aldehydes", *J. Org. Chem.*, 1979, 44, 1309–1317.

Arnott, S. And Hukins, D.W.L., "Optimised Parameters for A–DNA and B–DNA" *Biochem. and Biophys. Res. Commun.*, 1970, 47, 1504–1510.

Beaucage, S., et al., "Deoxynucleoside phosphoramidites—A new class of key intermediates for deoxypolynucleotide synthesis", *Tetrahedron Letters*, 1981, 22, 1859–1862.

Beaucage, S., et al., "3H–1,2–Benzodithiole–3–one 1,1–Dioxide as an Improved Sulfurizing Reagent in the Solid-–Phase Synthesis of Oliodeoxyribonucleoside Phosphorothioates", *J. Am. Chem. Soc.*, 1990, 112, 1253–1254.

Butke, G., Nucleic Acid Chemistry, Part 3: 149–152, Townsend, L.B. and Tipson, R.S., eds., J. Wiley and Sons, New York, 1986.

Caruthers, M., Oligonucleotides: "Antisense Inhibitors of Gene Expression", pp. 7–24, J.S. Cohen, ed., CRC Press, Inc., Boca Raton, FL, 1989.

Chen, Q.Y. and Wu, S.W., J. Chem. Soc. Perkin Trans., 1989, 2385–2387.

Cladek, S., et al., J. Carbohyd., Nucleosides & Nucleotides, 1980, 7, 63–75.

Ikehara, M. And Imura, J., "Studies of Nucleosides and Nucleotides–LXXXII.[1)] cyclonucleosides. (39).[2)] synthesis and properties of 2'halogen–2'–deoxyadenosines", *Chem. Pharm. Bull.* 1978, 26, 2449–2453.

Ikehara, M., "Studies of Nucleosides and Nucleotides–LXXIX.[1)], Purine cyclonucleosides. (37). The total synthesis of an antibiotic 2'–amino–2'–deoxyguanosine [2)]", *Chem. Pharm. Bull.*, 1978, 26, 240–244.

De las Heras, F., et al., "3–C–Cyano–3'–Deoxythymidine", *Tetrahedron Letters*, 1988, 29, 941–944.

Fox, J.J., et al., J. Org. Chem., 1964, 29, 558–564.

Freskos, J.N., "Synthesis of 2'Deoxypyrimidine Nucleosides Via Copper", *Nucleosides & Nucleotides*, 1989, 8, 1075–1076.

Gait, M.J., ed., Oligonucleotide Synthesis: A Practical Approach, IRL Press, Washington, D.C., 1984.

Hertel, L.W., et al., "Synthesis of 2–deoxy–2,2–difluoro- -D–ribose and 2–deoxy–2,2–difluoro–D–ribofuranosyl nucleosides", *J. Org. Chem.*, 1988, 53, 2406–2409.

Ikehara, M., et al., "Studies of Nucleosides and Nucleotides–LXXIV[1] Purine Cyclonucleosides—34 A New Method for the Synthesis of 2'–substituted 2'–deoxyadenosines", *Tetrahedron*, 1978, 34,1133–1138.

Ikehara, M., et al., "Purine 8–cyclonucleosides", *Accounts of Chemical Research*, 1969, 2, 47–53.

Ikehara, M., et al., "Improved Synthesis of 2'–fluoro–2'–deoxyadenosine and Synthesis and Carbon–13 NMR Spectrum of Its 3',5'–cyclic Phosphate Derivative", *Nucleosides & Nucleotides*, 1983, 2, 373–385.

Ikehara, M. And Imura, J., et al., "Studies of Nucleosides and Nucleotides–LXXXIV. Purine cyclonucleosides. (43). Synthesis and properties of 2'halogen–2'–deoxyguanosine", *Chem. & Pharm. Bull.*, 1981, 29, 3281–3285.

Ikehara, M. And Imura, J., et al., "Studies of Nucleosides and Nucleotides–LXXXVII[1)], Purine cyclonucleosides. XLII. Synthesis of 3'deoxy–2'fluorofunaosine", *Chem. & Pharm. Bull.*, 1981, 29, 1034–1038.

Inoue, et al., "Synthesis and hybridization studies on two complementary nona(2'–O–methyl)ribonucleotides" *Nucleic Acids Research*, 1987, 15, 6131–6148.

Jarvi, E.T., et al., "Synthesis and biological evaluation of dideoxunucleosides containing a difluoromethylene unit", *Nucleosides & Nucleotides*, 1989, 8, 1111–1114.

Jones, R.A., "Transient protection: Efficient one–flask synthesis of protected deoxynucleosides", *J. Am. Chem. Soc.*, 1982, 104, 1316–1319.

Koole, L.H., et al., "Synthesis of phosphate–methylated DNA fragments using 9–fluorenylmethoxycarbonyl as transient base protecting group", *J. Org. Chem.*, 1989, 54, 1657–1664.

Markiewicz, W.T. and Wiewiorowski, Nucleic Acid Chemistry, Part 3, pp. 222–231, Townsend, L.B. and Tipson, R.S., eds., J. Wiley & Sons, New York, 1986.

Ogilvie, K.K., Can. J. Chem., 1989, 67, 831–839.

Parkes, K.E.B. and Taylor, B., "A short synthesis of 3'–cyano–3'–Deoxythymidine", *Tetrahedron Letters*, 1988, 29, 2995–2996.

Ranganathan, "Modification of the 2'–Position of Purine Nucleosides: Synthesis of 2'–a–Substituted–2'–Deoxyadenosine Analogs", *Tetrahedron Letters*, 1977, 15, 1291–1294.

Robins, R.K., et al., J. Am. Chem. Soc., 1984, 106, 6379.

Sproat, B.S., et al., "New synthetic routes to protected purine 2'–O–methylriboside–3'–O–phosphormadites using a novel alkylation procedure", *Nucleic Acids Research*, 1990, 18, 41–49.

Sproat, B.S., et al., "Highly Efficient Chemical Synthesis of 2'–O–methylioligoribunocleotides and Tetrabiotinylated Derivatives; Novel Probes That are Resistant to Degradation by RNA or DNA Specific Nucleases", *Nucleic Acids Research*, 1989, 17, 3373–3386.

Sakanoue, et al., "Protein Kinase C Activity as Marker for Colorectal Cancer", *Int. J. Cancer*, 1991, 48, 803–806.

Berkowitz, et al., "Synthesis of 1,2–Dihydro–1–(2deoxy–β–D–Erythro–pentafuranosyl)–2–Oxopyrazine 4–oxide, a potent analog of deoxyuridine", *J. Med. Chem.*, 1973, 16(2), 183–184.

* cited by examiner

ANTISENSE OLIGONUCLEOTIDES WHICH HAVE PHOSPHOROTHIOATE LINKAGES OF HIGH CHIRAL PURITY AND WHICH MODULATE $\beta_I$, $\beta_{II}$, $\gamma$, $\delta$, $\epsilon$, $\zeta$ AND $\eta$ ISOFORMS OF HUMAN PROTEIN KINASE C

CROSS REFERENCE TO RELATED APPLICATIONS

This application is a continuation-in-part of the following U.S. patents and patent applications, each of which is commonly assigned with this application. The entire disclosure of each is herein incorporated by reference:

(1) U.S. Ser. No. 08/481,066, now U.S. Pat. No. 5,959,096, entitled "Oligonucleotide Modulation of Protein Kinase C," filed Jun. 7, 1995, which is a continuation-in-part of U.S. Ser. No. 08/089,996, entitled "Oligonucleotide Modulation of Protein Kinase C," filed Jul. 9, 1993, now U.S. Pat. No. 5,703,054 which is a continuation-in-part of U.S. Ser. No. 07/852,852, filed Mar. 16, 1992, now abandoned;

(2) U.S. Ser. No. 08/468,569, now U.S. Pat. No. 5,620,963, entitled "Oligonucleotides for Modulating Protein Kinase C Having Phosphorothioate Linkages of High Chiral Purity," filed Jun. 6, 1995, which is a continuation-in-part of (a) U.S. Ser. No. 08/297,703, filed Aug. 29, 1994, now U.S. Pat. No. 5,212,295, which is a continuation of U.S. Ser. No. 07/777,007, filed Oct. 16, 1991, now abandoned, and (b) U.S. Ser. No. 08/058,023, filed May 5, 1993, now U.S. Pat. No. 5,521,302 which is (i) a divisional of U.S. Ser. No. 07/777,760, filed Oct. 15, 1991, now U.S. Pat. No. 5,506,212; and (ii) a continuation-in-part of U.S. Ser. No. 07/777,007, filed Oct. 16, 1991, now abandoned, which is a continuation-in-part of Ser. No. 07/463,358, filed Jan. 11, 1990, now abandoned.

(3) U.S. Ser. No. 08/469,851, U.S. Pat. No. 5,587,361, entitled "Compounds Having Phosphorothioate Linkages of High Chiral Purity," which issued Dec. 24, 1996, which is a continuation-in-part of (a) U.S. Ser. No. 08/297,703, filed Aug. 29, 1994, now U.S. Pat. No. 5,506,212, which is a continuation of U.S. Ser. No. 07/777,007, filed Oct. 16, 1991, now abandoned, and (b) U.S. Ser. No. 08/058,023, filed May 5, 1993, now U.S. Pat. No. 5,521,302, which is (i) a divisional of U.S. Ser. No. 07/777,760, filed Oct. 15, 1991, now U.S. Pat. No. 5,212,295 and (ii) a continuation-in-part of U.S. Ser. No. 07/777,007, filed Oct. 16, 1991, now abandoned, which is a continuation-in-part of Ser. No. 07/463,358, filed Jan. 11, 1990, now abandoned.

(4) U.S. Ser. No. 08/470,129, now U.S. Pat. No. 5,635,488, entitled "Compounds Having Phosphorodithioate Linkages of High Chiral Purity," filed Jun. 6, 1995, which is a continuation-in-part of (a) U.S. Ser. No. 08/297,703, filed Aug. 29, 1994, now U.S. Pat. No. 5,506,212, which is a continuation of U.S. Ser. No. 07/777,007, filed Oct. 16, 1991, now abandoned, and (b) U.S. Ser. No. 08/058,023, filed May 5, 1993, now U.S. Pat. No. 5,521,302, which is (i) a divisional of U.S. Ser. No. 07/777,760, filed Oct. 15, 1991, now U.S. Pat. No. 5,212,295 and (ii) a continuation-in-part of U.S. Ser. No. 07/777,007, filed Oct. 16, 1991, now abandoned, which is a continuation-in-part of Ser. No. 07/463,358, filed Jan. 11, 1990, now abandoned.

(5) U.S. Ser. No. 07/770,760, now U.S. Pat. No. 5,212,295, entitled "Monomers for Preparation of Oligonucleotides Having Chiral Phosphorus Linkages," U.S. Ser. No. 07/777,760 filed Oct. 15, 1991, which is a continuation-in-part of U.S. Ser. No. PCT/US91/00243, filed Jan. 11, 1991, now U.S. Pat. No. 5,212,295, which is a continuation-in-part of (a) U.S. Ser. No. 07/463,358, filed Jan. 11, 1990, now abandoned, and (b) U.S. Ser. No. 07/566,977, filed Aug. 13, 1990, now abandoned; and (6) U.S. Ser. No. 08/297,703, entitled "Oligonucleotides with Substantially Chirally Pure Phosphorothioate Linkages," filed Aug. 29, 1994, now U.S. Pat. No. 5,506,212, which is a continuation of U.S. Ser. No. 07/777,007, filed Oct. 16, 1991, now abandoned, which is a continuation-in-part of Ser. No. 07/463,358, filed Jan. 11, 1990, now abandoned.

FIELD OF THE INVENTION

This invention relates to therapies, diagnostics, and research reagents for disease states which respond to modulation of the expression of the $\beta_I$, $\beta_{II}$, $\gamma$, $\delta$, $\epsilon$, $\zeta$ or $\eta$ isoform of protein kinase C. In particular, preferred embodiments, this invention relates to sequence-specific antisense phosphorothioate oligonucleotides comprising nucleosides joined by intersugar linkages, wherein the intersugar linkages are substantially pure (i.e. substantially all Sp or Rp) chiral phosphorothioate linkages which are specifically hybridizable with nucleic acids relating to the $\beta_I$, $\beta_{II}$, $\gamma$, $\delta$, $\epsilon$, $\zeta$ and $\eta$ isoforms of protein kinase C. These oligonucleotides modulate the expression of the $\beta_I$, $\beta_{II}$, $\gamma$, $\delta$, $\epsilon$, $\zeta$ and $\eta$ isoforms of protein kinase C, and are especially well suited as diagnostics, therapeutics and research reagents.

1. Protein Kinase C Isoforms

The phosphorylation of proteins plays a key role in the transduction of extracellular signals into cells. Kinases, the enzymes which effect such phosphorylations, are targets for the action of growth factors, hormones, and other agents involved in cellular metabolism, proliferation and differentiation. One of the major signal transduction pathways involves the enzyme protein kinase C (PKC), which is known to have many critical influences on cell proliferation and differentiation. PKC is activated by diacylglycerols (DAGs), which are metabolites released in signal transduction.

PKC is not a single enzyme, but a family of enzymes. At the present time at least seven isoforms (isozymes) of PKC have been identified. Isoforms $\alpha$, $\beta$, and $\gamma$ have been purified to homogeneity and isoforms $\delta$, $\epsilon$, $\zeta$ and $\eta$ have been identified by molecular cloning. These isozymes have distinct patterns of tissue and organ localization (see Nishizuka, *Nature,* 334:661, 1988, for a review) and may serve different physiological functions. For example, PKC-$\gamma$ seems to be expressed only in the central nervous system. As another example, PKC-$\eta$ has been found predominantly in the skin and lungs, with levels of expression much higher in these tissues than, for example, in the brain. This is in contrast to other members of the PKC family which tend to be most abundantly expressed in the brain (Osada et al., *J. Biol. Chem.* 265:22434, 1990). As a third example, PKC-$\alpha$ and -$\beta$ are expressed in most tissues, but have different patterns of expression in different cell types. Both PKC-$\alpha$ and PKC-$\beta$ are expressed in, and have been purified from, human epidermis; however, while PKC-$\alpha$ has been detected mainly in keratinocytes of the basal layers of the epidermis, PKC-$\beta$ is found mainly in the middle layers of the epidermis and Langerhans cells. It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin (Hegemann, L. and G. Mahrle, *Pharmacology of the Skin,* H. Mukhtar, ed., pp. 357–368, CRC Press, Boca Raton, Fla., 1992).

Interest in PKC was stimulated by the finding that PKC is a major cellular receptor through which a class of tumor-promoting agents called phorbol esters exert their pleiotropic effects on cells (Gescher et al., *Anti-Cancer Drug Design* 4:93, 1989). Phorbols capable of tumor production can mimic the effect of DAG in activating PKC, suggesting that these tumor promoters act through PKC and that activation of PKC is at least partially responsible for the resulting tumorigenesis (Parker et al., *Science* 233:853, 1986).

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer (Weinstein, *Cancer Res.* (Suppl.) 51:5080s, 1991). It has also been demonstrated that a greater proportion of the PKC in the colonic mucosa of patients with colorectal cancer is in an activated state compared to that of patients without cancer (Sakanoue et al., *Int. J. Cancer* 48:803, 1991).

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo (Endo et al., *Cancer Research* 51:1613, 1991; Borek et al., *Proc. Natl. Acad. Sci. (USA)* 88:1953, 1991). A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs (Gescher, A. and Dale, I. L., *Anti-Cancer Drug Design,* 4:93, 1989).

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis (Hegemann, L. and G. Mahrle, *Pharmacology of the Skin*, H. Mukhtar, ed., pp. 357–368, CRC Press, Boca Raton, Fla., 1992).

The oligonucleotides of the invention are useful in the therapeutic treatment of diseases associated with PKC isoforms. Such diseases include, but are not limited to, hyperproliferative and inflammatory conditions including psoriasis, tumors and cancers, for example glioblastoma, bladder cancer, breast cancer, lung cancer and colon cancer.

Although numerous compounds have been identified as PKC inhibitors (see Hidaka and Hagiwara, *Trends in Pharm. Sci.* 8:162, 1987, for a review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are potent in vitro inhibitors of PKC. However, these drugs exhibit only limited selectivity among different protein kinases (Gescher, *Anti-Cancer Drug Design* 4:93, 1989). Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes. Godson et al. (*J. Biol. Chem.* 268:11946, 1993) disclose the stable transfection of antisense PKC-α cDNA in cytomegalovirus promotor-based expression vectors to specifically decrease expression of PKC-α protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful. Ahmad et al. (*Neurosurg.* 35:904, 1994) disclose that transfection of the human glioblastoma cell line, U-87, with vectors expressing antisense RNA to PKC-α inhibits growth of the glioblastoma cells in vitro and in vivo. Diaz-Meco Conde et al. (WO Application 93/20101, published Oct. 14, 1993) disclose a peptide corresponding to the pseudo-substrate region of PKC-ζ and oligonucleotides antisense to this isozyme. Alvaro et al. (WO Application 94/29455, published Dec. 22, 1994) have identified a novel mutant form of PKC associated with tumors and disclose oligonucleotide sequences complementary to the mutant form.

The oligonucleotides of the invention are designed to be targeted to and modulate, as defined herein, the $β_I$, $β_{II}$, γ, δ, ε, ζ or η isoforms of PKC. Accordingly, the oligonucleotides of the invention are useful for the inhibition of specific non-α PKC isozymes, either in the course of research or in the diagnosis and treatment of diseases associated with particular non-α PKC isozymes.

2. Oligonucleotides Having Phosphorothioate Linkages of High Chiral Purity

Oligonucleotides are known to hybridize to single-stranded RNA or single-stranded DNA. Hybridization is the sequence-specific base pair hydrogen bonding of bases of the oligonucleotides to bases of target RNA or DNA. Such base pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (° C.) at which 50% helical (hybridized) versus coil (unhybridized) forms are present. $T_m$ is measured by using the UV spectrum to determine the formation and breakdown (melting) of the hybridization complex. Base stacking which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides can be used to effect enzymatic cleavage of a target RNA by using the intracellular enzyme RNase H. The mechanism of such RNase H cleavage requires that a 2'-deoxyribofuranosyl oligonucleotide hybridize to a target RNA. The resulting DNA-RNA duplex activates the RNase H enzyme and the activated enzyme cleaves the RNA strand.

Cleavage of the RNA strand destroys the normal function of the target RNA. Phosphorothioate oligonucleotides operate via this type of mechanism. However, for a DNA oligonucleotide to be useful for cellular activation of RNase H, the oligonucleotide must be reasonably stable to nucleases in order to survive in a cell for a time period sufficient for RNase H activation. For non-cellular uses, such as use of oligonucleotides as research reagents, such nuclease stability may not be necessary.

Several publications of Walder et al. describe the interaction of RNase H and oligonucleotides. Of particular interest are: (1) Dagle et al., *Nucleic Acids Research* 18:4751, 1990; (2) Dagle et al., *Antisense Research And Development* 1:11, 1991; (3) Eder et al., *J. Biol. Chem.* 266:6472, 1991; and (4) Dagle et al., *Nucleic Acids Research* 19:1805, 1991. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, the authors further note that in Xenopus embryos, both phosphodiester linkages and phosphorothioate linkages are also subject to exonuclease degradation. Such nuclease degradation is detrimental since it rapidly depletes the oligonucleotide available for RNase H activation.

As described in the above references (1), (2) and (4), to stabilize oligonucleotides against nuclease degradation while still providing for RNase H activation, 2'-deoxy oligonucleotides having a short section of phosphodiester linked nucleotides positioned between sections of phosphoramidate, alkyl phosphonate or phosphotriester linkages were constructed. While the phosphoamidate-containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such a decrease in the $T_m$ value is indicative of a decrease in hybridization between the oligonucleotide and its target nucleic acid strand.

Applications of oligonucleotides as diagnostics, research reagents, and therapeutic agents require that the oligonucleotides be transported across cell membranes or taken up by cells, appropriately hybridize to target RNA or DNA, and subsequently terminate or disrupt target nucleic acid function. These critical functions depend partly on the initial stability of oligonucleotides towards nuclease degradation. Further, these functions depend on specificity of the oligonucleotide for a target DNA or RNA molecule.

A serious deficiency of oligonucleotides for these purposes is their susceptibility to enzymatic degradation by a variety of ubiquitous nucleases which may be intracellularly and extracellularly located. Unmodified, "wild type", oligonucleotides are not useful as therapeutic agents because they are rapidly degraded by nucleases. Therefore, modification of oligonucleotides for conferring nuclease resistance on them has been the primary focus of research directed towards the development of oligonucleotide therapeutics and diagnostics.

Modifications of oligonucleotides to enhance nuclease resistance has generally taken place on the sugar-phosphate backbone, particularly on the phosphorous atom. Phosphorothioates have been reported to exhibit resistance to nucleases. In addition, phosphorothioate oligonucleotides are generally more chemically stable than natural phosphodiester oligonucleotides. Phosphorothioate oligonucleotides also exhibit solubility in aqueous media. Further, phosphorothioate oligonucleotide-RNA heteroduplexes can serve as substrates for endogenous RNase H. Additionally, phosphorothioate oligonucleotides exhibit high thermodynamic stability. However, while the ability of an oligonucleotide to bind to a target DNA or RNA with fidelity is critical for its hybridization to the target DNA or RNA, modifications at the phosphorous atom of the oligonucleotides, while exhibiting various degrees of nuclease resistance, have generally suffered from inferior hybridization properties (Cohen, J. S., Ed., Oligonucleotides: *Antisense Inhibitors of Gene Expression*, CRC Press, Inc., Boca Raton, Fla., 1989).

One reason for this inferior hybridization may be the prochiral nature of the phosphorous atom. Modifications on the internal phosphorous atom of modified phosphorous oligonucleotides results in Rp and Sp stereoisomers. Modified phosphorus oligonucleotides obtained thus far, wherein the resulting molecule has nonsymmetrical substituents, have been racemic mixtures having $2^n$ isomers, with n equal to the number of phosphorothioate intersugar linkages in the oligonucleotide. Thus, a 15-mer phosphorothioate oligonucleotide, containing 14 asymmetric centers has $2^{14}$ or 16,384 diastereomers. In view of this, in a racemic mixture, only a small percentage of the oligonucleotides are likely to specifically hybridize to a target mRNA or DNA with optimal affinity.

Chemically synthesized phosphorothioate oligonucleotides having chirally pure intersugar linkages had thus far been limited to molecules having only one or two diastereomeric intersugar linkages. Until recently, the effects of induced chirality in chemically synthesized racemic mixtures of sequence-specific phosphorothioate oligonucleotides had not been assessed, since synthesis of oligonucleotides having chirally pure intersugar linkages had yet to be accomplished by automated synthesis. This was due to the non-stereospecific incorporation of sulfur during automated synthesis. For example, Stec et al. (*J. Chromatography* 326:263, 1985), synthesized certain oligonucleotide phosphorothioates having racemic intersugar linkages, however, they were able to resolve only the diastereomers of certain small oligomers having one or, at most, two diastereomeric phosphorous intersugar linkages. Stec et al. subsequently reported (*Nucl. Acids Res.* 19:5883, 1991)the automated stereocontrolled synthesis of oligonucleotides. The procedure described in the above-mentioned reference utilizes base-catalyzed nucleophilic substitution at a pentavalent phosphorothioyl center.

The synthesis of phosphorothioates having all Rp intersugar linkages using enzymatic methods has been investigated by several authors (Burgers and Eckstein, *J. Biol. Chem.* 254:6889, 1979); Gupta et al., *J. Biol. Chem.* 256:7689, 1982); Brody and Frey, *Biochemistry* 20:1245, 1981); and Eckstein and Jovin, *Biochemistry* 2:4546, 1983). Brody et al. (*Biochemistry* 21:2570, 1982) and Romaniuk and Eckstein, (*J. Biol. Chem.* 257:7684, 1982) enzymatically synthesized poly TpA and poly ApT phosphorothioates, while Burgers and Eckstein (*Proc. Natl. Acad. Sci.* (*USA*) 75:4798, 1978) enzymatically synthesized poly UpA phosphorothioates. Cruse et al. (*J. Mol. Biol.* 192:891, 1986) linked three diastereomeric Rp GpC phosphorothioate dimers via natural phosphodiester bonds into a hexamer.

The relative ability of an oligonucleotide to bind to complementary nucleic acids may be compared by determining the melting temperature of a particular hybridization complex. The melting temperature ($T_m$), a characteristic physical property of double helixes, denotes the temperature (° C.) at which 50% helical versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$.

In a preliminary report (Stec, J. W., *Oligonucleotides as Antisense Inhibitors of Gene Expression: Therapeutic Implications*, Meeting Abstracts, Jun. 18–21, 1989), thymidine homopolymer octamers having all but one linkage being modified phosphate linkages ("all except one") Rp stereoconfiguration or "all except one" Sp stereoconfiguration in the intersugar linkages were formed from two thymidine methylphosphonate tetrameric diastereomers linked by a natural phosphodiester bond. It was noted that a Rp "all except one" methylphosphonate non-sequence-specific thymidine homooctamer, i.e., $(dT)_8$ having all but one Rp intersugar linkage, formed a thermodynamically more stable hybrid (Tm 38° C.) with a 15-mer deoxyadenosine homopolymer (i.e., $(dA)_{15}$) than a hybrid formed by a similar thymidine homopolymer having "all except one" Sp configuration methylphosphonate linkages and of $d(A)_{15}$ (Tm<0° C.), i.e., a $d(T)_{15}$ having all but one Sp intersugar linkage. A hybrid between $(dT)_8$ having natural phosphodiester linkages (i.e., octathymidylic acid) and $d(A)_{15}$ was reported to have a Tm of 14° C.

More recently, Ueda et al. (*Nucl. Acids Research* 19:547, 1991) enzymatically synthesized mRNAs intermittently incorporating Rp diastereomeric phosphorothioate linkages for use in translation systems. Ueda et al. employed T7 coliphane DNA having seventeen promoters and one termination site for T7 RNA polymerase. In vitro synthesis by T7 RNA polymerase produced mRNAs having from several hundred to tens of thousands of nucleotides.

Backbone chirality may also affect the susceptibility of a phosphorothioate oligonucleotide-RNA heteroduplex to RNAse H activity. The ability to serve as a template for RNAse H has significant therapeutic implications since it has been suggested that RNAse H causes cleavage of the RNA component in an RNA-DNA oligonucleotide heteroduplex. With oligonucleotides containing racemic mixtures of Rp and Sp intersugar linkages, it is not known if all phosphorothioate oligonucleotides can function equally as substrates for RNase H. For a variety of catalytic reactions, hydrolysis of the phosphodiester backbone of nucleic acids proceeds by a stereospecific mechanism (an in-line mechanism) and inversion of configuration. Therefore, there may be only a small percentage of oligonucleotides in a racemic mixture that contain the correct chirality for maximum hybridization efficiency and termination of translation. Thus, increasing the percentage of phosphorothioate oligonucleotides that can serve as substrates for RNAse H in a heteroduplex will likely lead to a more efficacious compound for antisense and other oligonucleotide therapies.

To enhance hybridization fidelity, phosphorothioate oligonucleotides having substantially chirally pure intersugar linkages are greatly desired. Further, such phosphorothioate oligonucleotides having substantially chirally pure intersugar linkages would lead to more efficacious therapeutic compounds. However, until now little success has been achieved in synthesizing such molecules. Therefore, simple methods of synthesizing phosphorothioate oligonucleotides having substantially chirally pure intersugar linkages are greatly desired.

OBJECTS OF THE INVENTION

Current agents which modulate the activity or metabolism of protein kinase C (PKC) either exhibit many unacceptable side effects due to their lack of specificity for a particular isozyme, or exhibit only limited effectiveness in inhibiting PKC. The instant invention circumvents problems encountered by prior workers by modulating the production of a specific PKC isozyme, rather than inhibiting PKC isozymes generally and directly, to achieve the therapeutic effect. In the instant invention, the oligonucleotide is designed to bind directly to mRNA or to a gene encoding a PKC isozyme, ultimately modulating the amount of the PKC isozyme made from the corresponding gene. It is an object of this invention to provide sequence-specific phosphorothioate oligonucleotides having substantially chirally pure (either all Rp or all Sp) intersugar linkages, wherein such oligonucleotides modulate the expression of the $\beta_I$, $\beta_{II}$, $\gamma$, $\delta$, $\epsilon$, $\zeta$ or $\eta$ isoform of protein kinase C.

It is another object of this invention to provide methods for synthesis of sequence-specific phosphorothioate oligonucleotides having substantially chirally pure intersugar linkages, wherein such olgonucleotides modulate the expression of a $\beta_I$, $\beta_{II}$, $\gamma$, $\delta$, $\epsilon$, $\zeta$ or $\eta$ isoform of protein kinase C.

These and other objects of the present invention shall become apparent to persons skilled in the art to which this invention pertains given this specification and the claims appended hereto.

BRIEF DESCRIPTION OF THE DRAWINGS

FIG. 9 is a set of bar graphs showing the effect of additional oligonucleotides on PKC-α mRNA levels.

Figure 10:
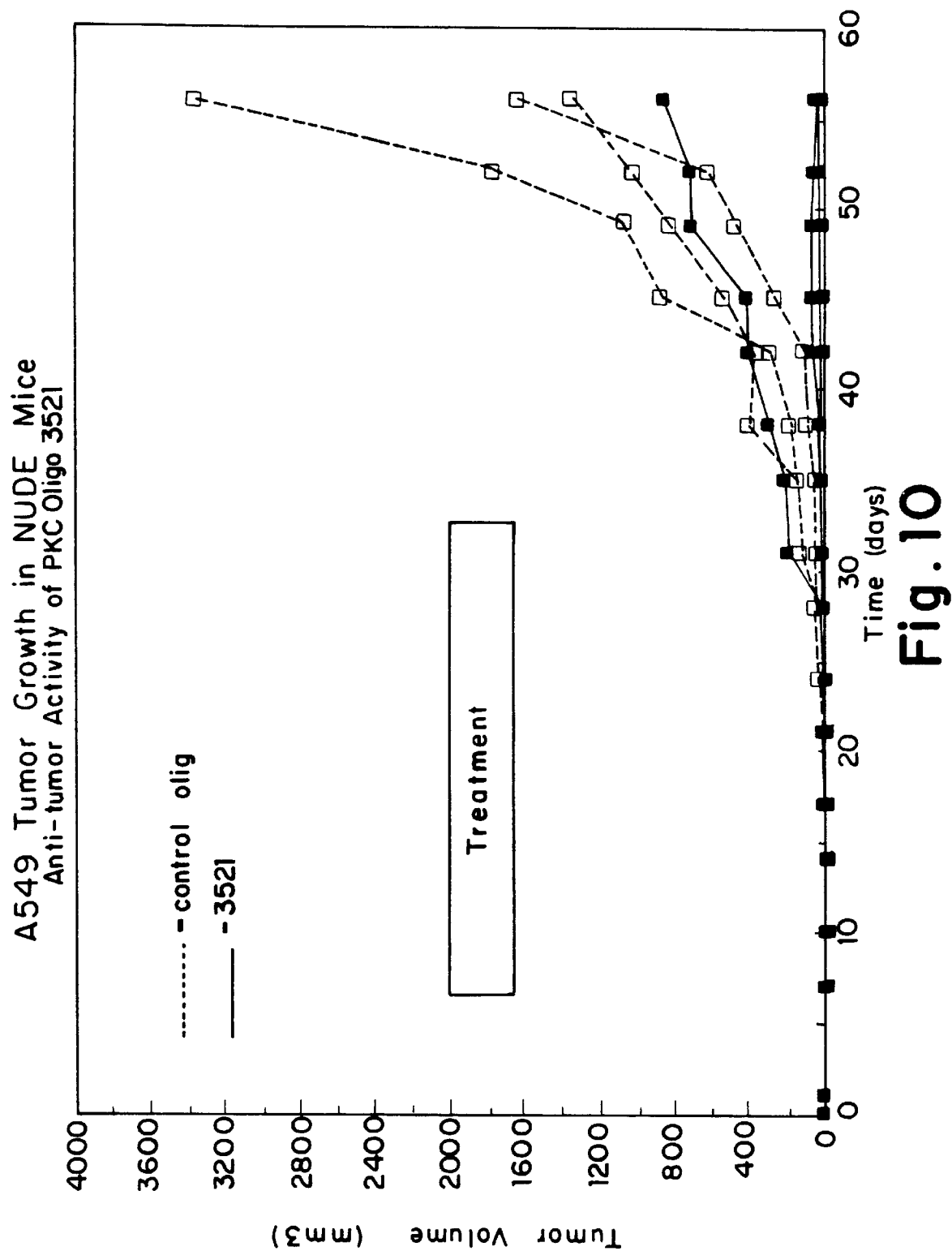

FIG. 10 is a line graph showing anti-tumor activity of ISIS 3521. Each dashed line represents tumor volume in one animal treated with control oligonucleotide; each solid line represents tumor volume in one animal treated with ISIS 3521.

Figure 11A:
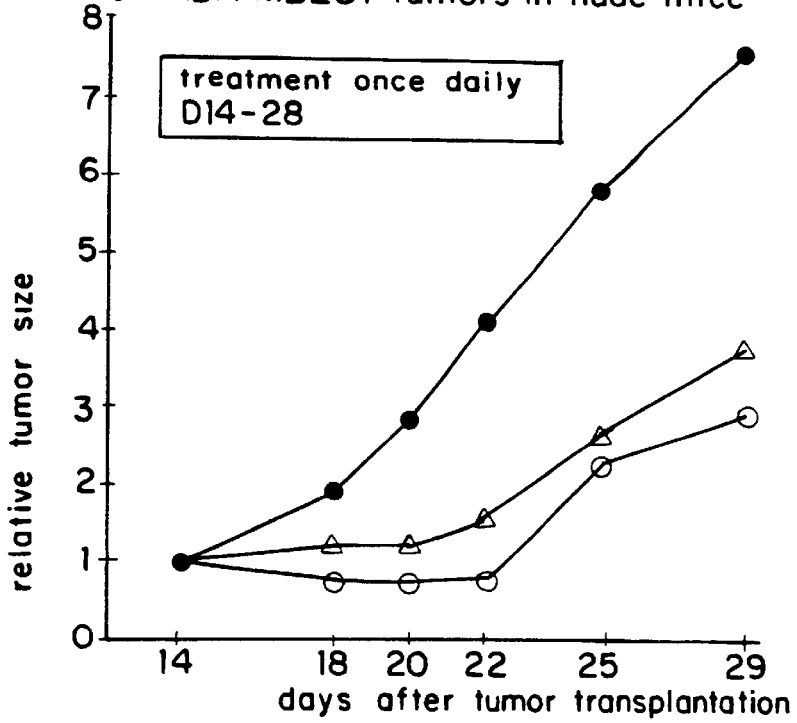
Figure 11B:
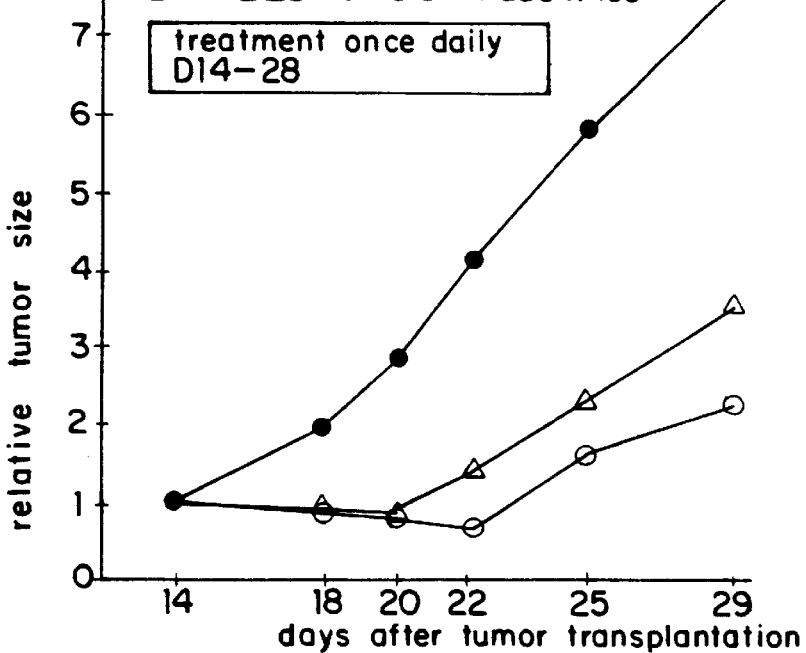

FIG. 11 is a set of line graphs showing effect of oligonucleotides on growth of human MDA-MB231 tumors in nude mice. FIG. 11A shows results obtained with ISIS 3521; FIG. 11B shows results obtained with ISIS 3527. Each line represents tumor volume in one animal. Symbols: ●=control; ○=oligonucleotide at 60 mg/kg; Δ=oligonucleotide at 6 mg/kg.

Figure 12:
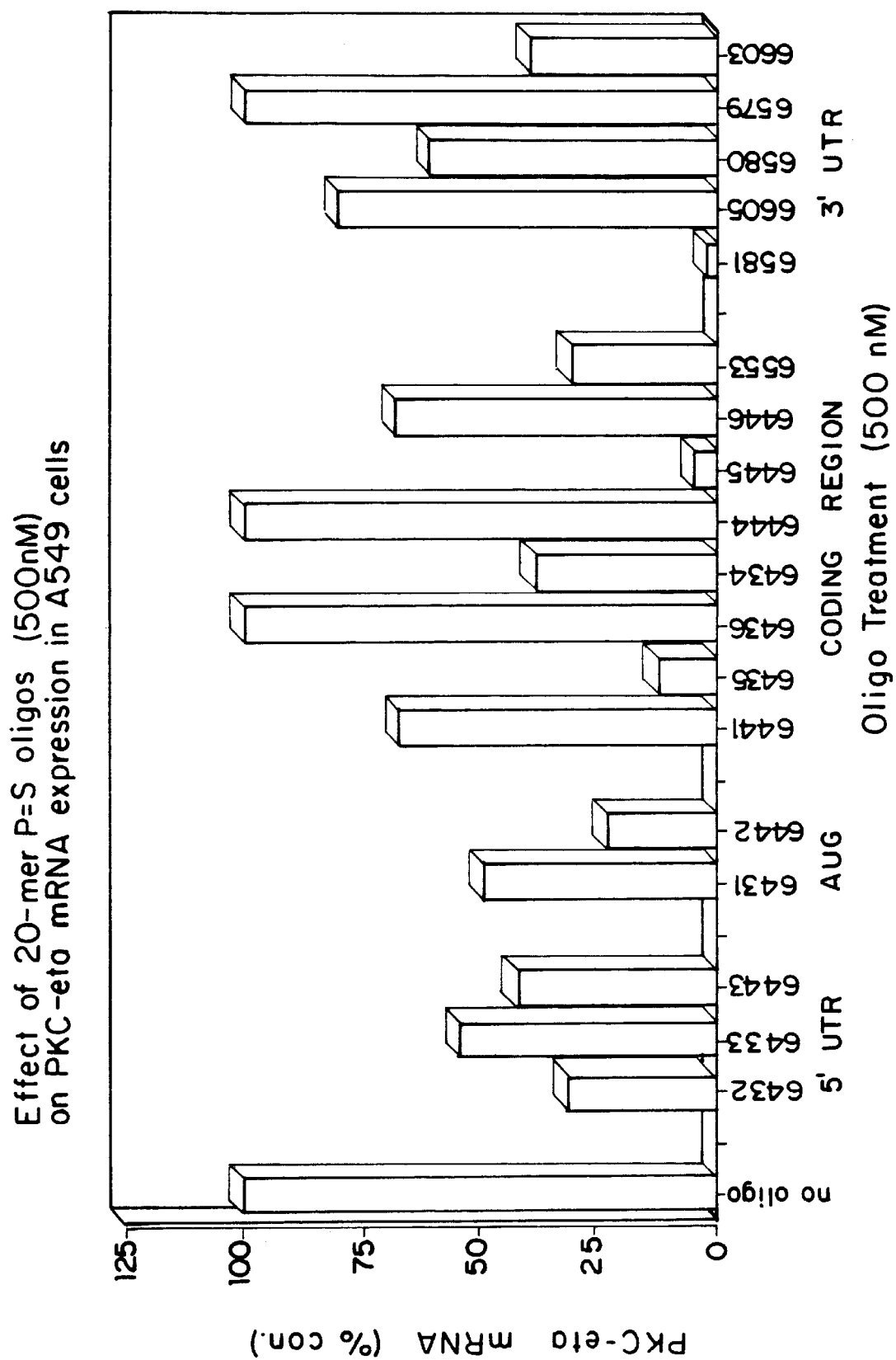

FIG. 12 is a line graph showing the effect of ISIS 8459 (2' fluoro gapped version of ISIS 3521) on the growth of A549 xenografts in nude mice. All doses (0.006, 0.06, 0.6, 6.0 mg/kg) of ISIS 8459 inhibit tumor growth.

Figure 13:
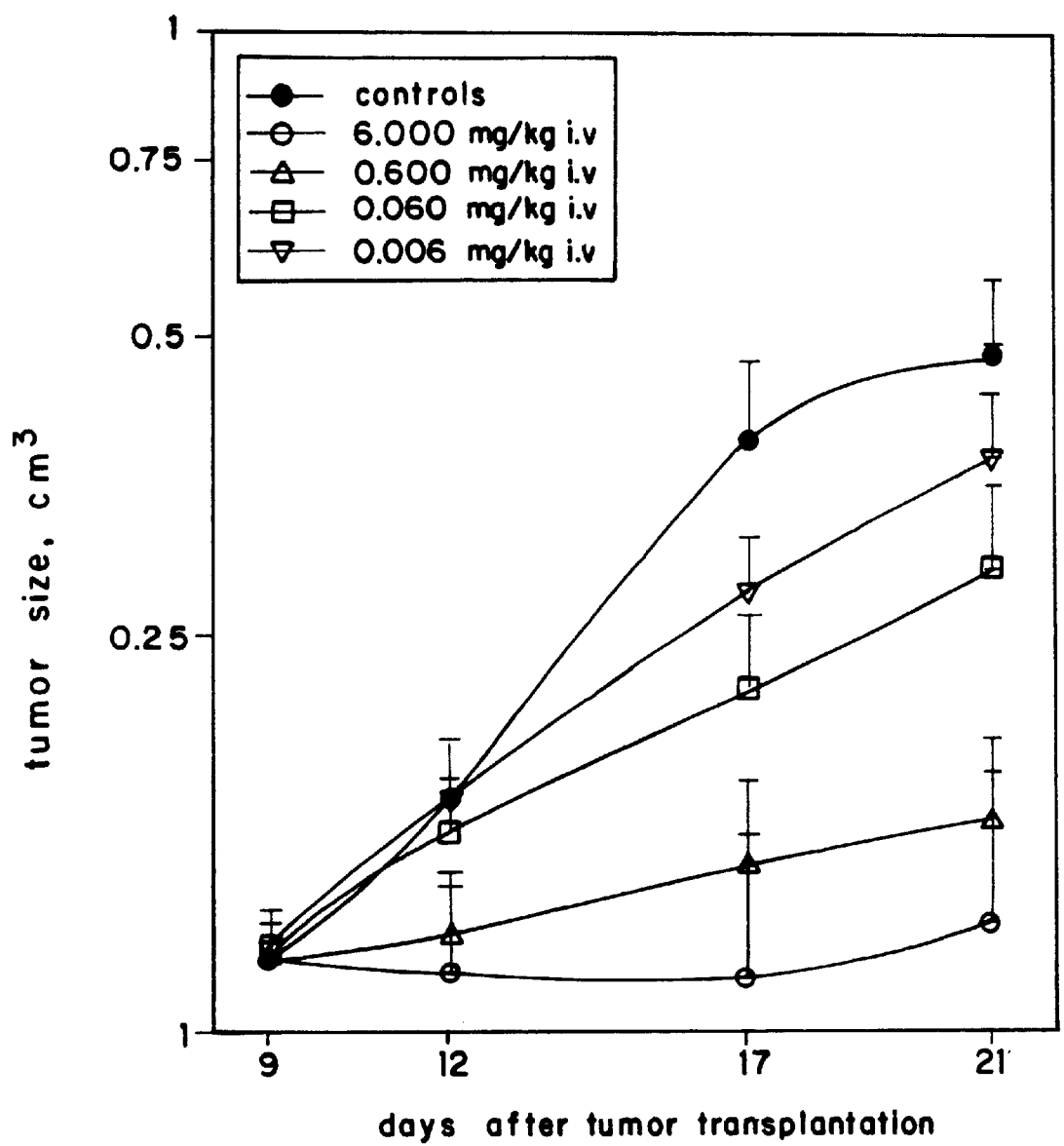

FIG. 13 is a line graph showing a "crossover" experiment to evaluate the effect of ISIS 3521 on U-87 glioblastoma cells in nude mice. The experiment was carried out with oligonucleotide doses of 2 mg/kg and 20 mg/kg and then treatment was switched (arrow). The group which had originally received ISIS 3521 at 20 mg/kg ("high dose-to-control" group, closed triangles) then received saline and the group which had originally received ISIS 3521 at 2 mg/kg ("low dose-to-high dose", open triangles) then received ISIS 3521 at 20 mg/kg. Other symbols: S=sense oligonucleotide (control); AS=antisense oligonucleotide (ISIS 3521) targeted to PKC-α.

Figure 14:
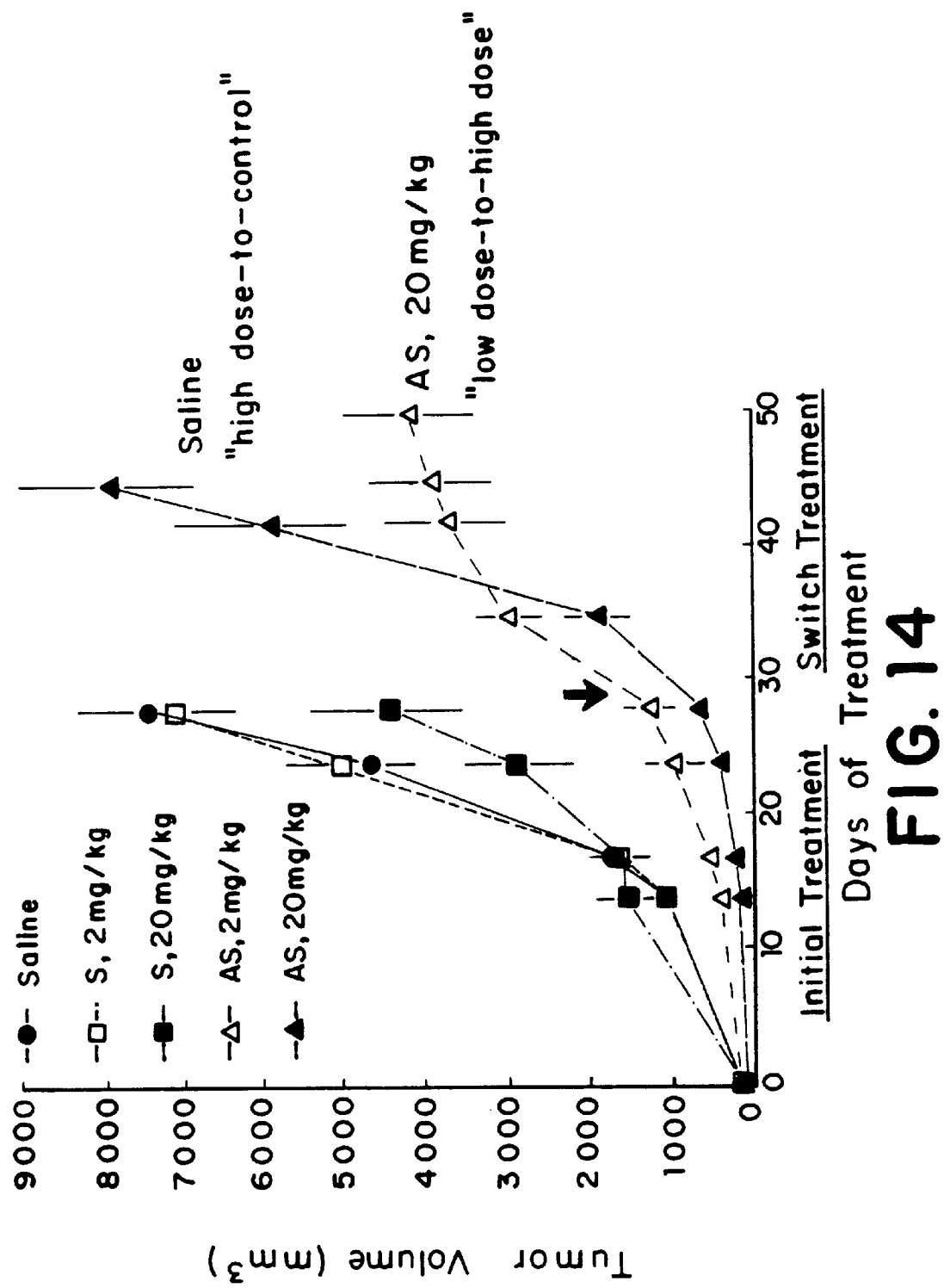

FIG. 14 is a bar graph showing effect of 20-mer phosphorothioate oligonucleotides on PKC-η expression in A549 cells.

SUMMARY OF THE INVENTION

In accordance with the present invention, oligonucleotides are provided that are complementary to, and specifically hybridizable with, a nucleic acid that encodes a $\beta_I$, $\beta_{II}$, $\gamma$, $\delta$, $\epsilon$, $\zeta$ or $\eta$ isoform of protein kinase C (PKC). Because a protein-encoding strand of a nucleic acid is referred to as the "sense" strand, oligonucleotides that are complementary thereto are commonly denominated as being "antisense." Such antisense oligonucleotides modulate the expression of the targeted gene and thus affect the level of the resultant gene product (i.e., the protein encoded by the gene). Accordingly, such oligonucleotides may be conveniently and desirably presented in a pharmaceutically acceptable carrier to an animal in need of modulation of a $\beta_I$, $\beta_{II}$, $\gamma$, $\delta$, $\epsilon$, $\zeta$ or $\eta$ PKC isoform.

A unique aspect of the chemical structures of the oligonucleotides of the invention is that they comprise substantially chirally pure phosphorothioate intersugar linkages in place of the phosphodiester intersugar linkages that are present in naturally occurring nucleic acids. The term "substantially chirally pure" is intended to indicate that the intersugar linkages of the oligonucleotides of the invention are either substantially all Sp, or substantially all Rp, phosphorothioate intersugar linkages. Alternative methods of synthesizing the substantially chirally pure oligonucleotides of the invention are also herein provided. Phosphorothioate oligonucleotides having substantially chirally pure intersugar linkages are useful for modulating the activity of their target RNA in a variety of ways. For example, such oligonucleotides have an increased thermodynamic stability, compared to phosphodiester oligonucleotides of identical sequence, in heteroduplexes formed with the target RNA.

Also provided are methods for modulating the expression of PKC or of a particular PKC isozyme or set of isozymes in cells or tissues. Additional aspects of the invention are directed to methods of detection in cells or tissues of nucleic acids that encode PKC and specific detection in cells or tissues of nucleic acids that encode particular PKC isozymes. Other aspects of the invention are directed to methods for diagnostics and therapeutics of animals suspected of having a disease or disorder associated with the $\beta_I$, $\beta_{II}$, $\gamma$ or $\eta$ isoform of PKC. Such methods comprise contacting cells or tissues suspected of containing said gene with oligonucleotides in accordance with the invention. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Also provided are pharmaceutical compositions comprising one or more of the oligonucleotides of the invention.

In accordance with preferred embodiments, the present invention employs oligonucleotides for use in antisense inhibition of the function of RNA and DNA encoding protein kinase C (PKC) isoforms, i.e., PKC-$\beta_I$, PKC-$\beta_{II}$, PKC-$\gamma$, PKC-$\delta$, PKC-$\epsilon$, PKC-$\zeta$ or PKC-$\eta$. The present invention also employs oligonucleotides which are designed to be specifically hybridizable to DNA or messenger RNA (mRNA) encoding such proteins and ultimately to modulate the amount of such proteins transcribed from their respective genes. Such hybridization with mRNA interferes with the normal role of mRNA and causes a modulation of its function in cells. The functions of mRNA to be interfered with can include any vital function such as translocation of the RNA to the site for protein translation, actual translation of protein from the RNA, splicing of the RNA to yield one or more mRNA species, and independent catalytic activity which may be engaged in by the RNA. The overall effect of such interference with mRNA function is modulation of the expression of a PKC protein, wherein "modulation" means either an increase (stimulation) or a decrease (inhibition) in the expression of a PKC protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of a repeating unit generically known as a nucleotide. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, A., *DNA Replication*, pp. 4–7, W. H. Freeman & Co., San Francisco, 1980). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with a protein kinase C isoform for which modulation is desired in certain instances. The targeting process also includes determination of a region (or regions) within this gene for the oligonucleotide interaction to occur such that the desired effect, either detection or modulation of expression of the protein, will result. Once the target region have been identified, oligonucleotides are chosen which are sufficiently complementary to the target, i.e., hybridize sufficiently well and with sufficient specificity to give the desired effect.

The oligonucleotides of this invention are designed to be hybridizable with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. Regions of a gene that may be targeted for antisense modulation include the 5' untranslated region or "5' cap" (hereinafter, the "5'-UTR"), the translation initiation codon region (hereinafter, the "tIR"), the open reading frame (hereinafter, the "ORF"), the translation termination codon region (hereinafter, the "tTR"), the 3' untranslated region (hereinafter, the "3'-UTR") and an intron/exon junction. As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell*, pp. 411–415, Garland Publishing Inc., New York, 1983). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors* 4:45, 1990; Gelbert et al., *Somat. Cell. Mol. Genet.* 16:173, 1990; Gold and Stormo, in: *Escherichia coli* and *Salmonella*

*typhimurium: Cellular* and *Molecular Biology*, Vol. 2, p. 1303, Neidhardt et al., eds., American Society for Microbiology, Washington, D.C., 1987). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development* 121:3723, 1995; Gao et al., *Cancer Res.* 55:743, 1995; McDermott et al., *Gene* 117:193, 1992; Perri et al., *J. Biol. Chem.* 266:12536, 1991; French et al., *J. Virol.* 63:3270, 1989; Pushpa-Rekha et al., *J. Biol. Chem.* 270:26993, 1995; Monaco et al., *J. Biol. Chem.* 269:347, 1994; DeVirgilio et al., *Yeast* 8:1043, 1992; Kanagasundaram et al., *Biochim. Biophys. Acta* 1171:198, 1992; Olsen et al., *Mol. Endocrinol.* 5:1246, 1991; Saul et al., *Appl. Environ. Microbiol.* 56:3117, 1990; Yaoita et al., *Proc. Natl. Acad. Sci.* (*USA*) 87:7090, 1990; Rogers et al., *EMBO J.* 9:2273, 1990). In the context of the invention, "start codon" and "translation initiation codon" refer to the codon or codons that are used in vivo to initiate translation of an mRNA molecule transcribed from a gene encoding a PKC protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

In the context of this invention, the term "oligonucleotide" includes oligonucleotides composed of naturally-occurring nucleobases, sugars and covalent intersugar (backbone) linkages as well as oligonucleotides having non-naturally-occurring portions which function similarly. Such modified or substituted oligonucleotides may be preferred over native forms because of desirable properties such as, for example, enhanced cellular uptake, enhanced binding to target and increased stability in the presence of nucleases. Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N ($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science* 254:1497, 1991).

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids (e.g., hypoxanthine; xanthine; 6-methyladenine; 5-methylcytosine; 5-hydroxymethylcytosine (HMC); glycosyl HMC and gentiobiosyl HMC) as well synthetic nucleobases (e.g., 2-aminoadenine; 2-thiouracil; 2-thiothymine; 5-bromouracil; 5-hydroxymethyluracil; 8-azaguanine; 7-deazaguanine, $N^6$(6-aminohexyl)adenine; 6-methyl, 2-propyl and other alkyl adenines; 2,6-diaminopurine; 5-halo uracil; 5-halo cytosine; 6-aza uracil; 6-aza cytosine; 6-aza thymine; pseudo uracil; 4-thiouracil; 8-halo adenine; 8-aminoadenine, 8-thiol adenine, 8-thiolalkyl adenines, 8-hydroxyl adenine and other 8-substituted adenines; 8-halo guanines, 8-amino guanine, 8-thiol guanine, 8-thiolalkyl guanines, 8-hydroxyl guanine and other 8-substituted guanines; other aza and deaza uracils; other aza and deaza thymidines; other aza and deaza cytosines, other aza and deaza adenines; other aza and deaza guanines; 5-trifluoromethyl uracil; and 5-trifluoro cytosine (Kornberg, A., *DNA Replication*, pp. 75–77, W. H. Freeman & Co., San Francisco, 1980; Gebeyehu, G., et al., *Nucleic Acids Res.* 15:4513, 1987). Such modified nucleotides may be introduced during chemical synthesis of the oligonucleotides of the invention; however, to the extent that nucleoside-5'-O-(1-thiotriphosphate) analogs are substrates for suitable polymerases, the oligonucleotides of the invention also include modified bases or modified sugars enzymatically incorporated within the oligonucleotides of the invention.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage.

Natural sugars include β-D-ribofuranosyl and β-D-2'-deoxy-erythro-pentofuranosyl. The oligonucleotides of the invention may additionally or alternatively comprise substitutions of the sugar portion of the individual nucleotides. For example, oligonucleotides may also have sugar mimetics such as cyclobutyls in place of the pentofuranosyl group. Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties.

A preferred modification includes 2'-methoxyethoxy [2'-O—CH$_2$CH$_2$OCH$_3$, also known as 2'-O-(2-methoxyethyl)] (Martin et al., *Helv. Chim. Acta* 78:486, 1995). Other preferred modifications include 2'-methoxy (2'-O—CH$_3$), 2'-propoxy (2'-OCH$_2$CH$_2$CH$_3$) and 2'-fluoro (2'-F)

Similar modifications may also be made at other positions on the oligonucleotide, particularly the 3' position of the sugar on the 3' terminal nucleotide and the 5' position of 5' terminal nucleotide. The 5' and 3' termini of an oligonucleotide may also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology*, Volume 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu, G., et al., *Nucleic Acids Res.* 15:4513, 1987). Such lipophilic moieties include but are not limited to a cholesteryl moiety (Letsinger et al., *Proc. Natl. Acad. Sci. USA*, 86:6553, 1989), cholic acid (Manoharan et al., *Bioorg. Med. Chem. Let.* 4:1053, 1994), a thioether, e.g., hexyl-S-tritylthiol (Manoharan et al., *Ann. N.Y. Acad. Sci.*, 660:306, 1992; Manoharan et al., *Bioorg. Med. Chem. Lett.* 3:2765, 1993), a thiocholesterol (Oberhauser et al., *Nucl. Acids Res.* 20:533, 1992), an aliphatic chain, e.g., dodecandiol or undecyl residues (Saison-Behmoaras et al., *EMBO J.* 10:111, 1991; Kabanov et al., *FEBS Lett.* 259:327, 1990; Svinarchuk et al., *Biochimie* 75:49, 1993), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 36:3651, 1995; Shea et al., *Nucl. Acids Res.* 18:3777, 1990), a polyamine or a polyethylene glycol chain (Manoharan et al., *Nucleosides & Nucleotides* 14:969, 1995), or adamantane acetic acid (Manoharan et al., *Tetrahedron Lett.* 36:3651, 1995), a palmityl moiety (Mishra et al., *Biochim. Biophys. Acta* 1264:229, 1995), or an octadecylamine or hexylamino-carbonyl-oxycholesterol moiety (Crooke et al., *J. Pharmacol. Exp. Ther.* 277:923, 1996). Oligonucleotides comprising lipophilic moieties, and methods for preparing such oligonucleotides, are disclosed in U.S. Pat. Nos. 5,138,045, 5,218,105 and 5,459,255.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonuc-Leotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy substituted), or vice-versa.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives. Teachings regarding the synthesis of particular modified oligonucleotides are hereby incorporated by reference from the following U.S. patents or pending patent applications, each of which is commonly assigned with this application:

U.S. Pat. Nos. 5,138,045 and 5,218,105, drawn to polyamine conjugated oligonucleotides;

U.S. Pat. No. 5,212,295, drawn to monomers for the preparation of oligonucleotides having chiral phosphorus linkages;

U.S. Pat. Nos. 5,378,825 and 5,541,307, drawn to oligonucleotides having modified backbones;

U.S. Pat. No. 5,386,023, drawn to backbone modified oligonucleotides and the preparation thereof through reductive coupling;

U.S. Pat. No. 5,457,191, drawn to modified nucleobases based on the 3-deazapurine ring system and methods of synthesis thereof;

U.S. Pat. No. 5,459,255, drawn to modified nucleobases based on N-2 substituted purines;

U.S. Pat. No. 5,521,302, drawn to processes for preparing oligonucleotides having chiral phosphorus linkages;

U.S. Pat. No. 5,539,082, drawn to peptide nucleic acids;

U.S. Pat. No. 5,554,746, drawn to oligonucleotides having β-lactam backbones;

U.S. Pat. No. 5,571,902, drawn to methods and materials for the synthesis of oligonucleotides;

U.S. Pat. No. 5,578,718, drawn to nucleosides having alkylthio groups, wherein such groups may be used as linkers to other moieties, attached at any of a variety of positions of the nucleoside; and U.S. Pat. No. 5,587,361, drawn to oligonucleotides having phosphorot-hioate linkages of high chiral purity.

The oligonucleotides of the present invention can be utilized as therapeutic compounds, diagnostic tools and as research reagents and kits. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention. For therapeutic uses, an animal suspected of having a disease or disorder which can be treated or prevented by modulating the expression or activity of a PKC protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of PKC isoform-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual*, Vol. 2, p. 10.59, Cold Spring Harbor Laboratory Press, 1989). Radiolabeled oligonucleotides are then contacted with cell or tissue samples suspected of containing PKC message RNAs (and thus PKC proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of PKC proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a PKC gene. Quantitation of the silver grains permits detection of the expression of mRNA molecules encoding these proteins and permits targeting of oligonucleotides to these areas.

Analogous assays for fluorescent detection of expression of PKC nucleic acids can be developed using oligonucleotides of the present invention which are conjugated with fluorescein or other fluorescent tags instead of radiolabeling. Such conjugations are routinely accomplished during solid phase synthesis using fluorescently labeled amidites or controlled pore glass (CPG) columns. Fluorescein-labeled amidites and CPG are available from, e.g., Glen Research (Sterling, Va.).

The present invention employs oligonucleotides targeted to nucleic acids encoding PKC proteins and oligonucleotides targeted to nucleic acids encoding such proteins. Kits for detecting the presence or absence of expression of a PKC protein may also be prepared. Such kits include an oligonucleotide targeted to an appropriate gene, i.e., a gene encoding a PKC protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a PKC protein can be detected by means known in the art. Such means may include conjugation of an enzyme to the oligonucleotide, radiolabelling of the oligonucleotide or any other suitable detection systems. Since the oligonucleotides of this invention hybridize to the PKC gene and its mRNA, sandwich and other assays can easily be constructed to exploit this fact. Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish PKC-associated tumors, particularly tumors associated with a particular PKC isozyme, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of PKC expression, particularly the specific expression of individual isozymes of PKC. For example, radiolabeled oligonucleotides can be prepared by $^{32}$P labeling at the 5' end with polynucleotide kinase (Sambrook et al., *Molecular Cloning. A Laboratory Manual*, Vol. 2, Cold Spring Harbor Laboratory Press, Cold Spring Harbor, N.Y., p. 10.59, 1989). Radiolabeled oligonucleotides are then contacted with tissue or cell samples suspected of PKC expression and the sample is washed to remove unbound oligonucleotide. Radioactivity remaining in the sample indicates bound oligonucleotide (which in turn indicates the presence of PKC) and can be quantitated using a scintillation counter or other routine means. Radiolabeled oligonucleotides can also be used to perform autoradiography of tissues to determine the localization, distribution and quantitation of PKC expression for research, diagnostic or therapeutic purposes. in such studies, tissue sections are treated with radiolabeled oligonucleotide and washed as described above, then exposed to photographic emulsion according to routine autoradiography procedures. The emulsion, when developed, yields an image of silver grains over the regions expressing the PKC isozyme of choice. Quantitation of the silver grains permits PKC expression to be detected.

Analogous assays for fluorescent detection of PKC expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling, Va.; 1993 Catalog of Products for DNA Research, p. 21, Glen Research, Sterling, Va., 1993).

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Affinity of an oligonucleotide for its target (in this case a nucleic acid encoding PKC) is routinely determined by measuring the $T_m$ of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase PKC mRNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PKC gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides.

A variety of oligonuc-Leotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. All such oligonucleotides are best described as being functionally interchangeable with natural oligonucleotides (or synthesized oligonucleotides along natural lines), but having one or more differences from natural structure. All such oligonucleotides are comprehended by this invention so long as they function effectively to hybridize with the targeted PKC nucleic acid.

The phosphorous atom in a phosphodiester linkage of an oligonucleotide can be described as being "prochiral." Once a non-bonding oxygen atom of the phosphodiester linkage is replaced or modified, a chiral sugar-phosphate linkage is generated. The resulting intersugar linkage is either an Sp intersugar linkage or an Rp intersugar linkage. Replacement of a non-bonding oxygen atom of the natural phosphodiester linkage with sulfur to obtain a phosphorothioate linkage results in the generation of a chiral center and affords Sp and Rp diastereomers. Molecules wherein substantially all of the phosphorous atoms in the sugar backbone are either Sp or Rp are referred to herein as chirally pure.

Ribonucleoside-(NTPαS) and 2'-deoxyribonucleoside-5'-O-(1-thiotriphosphates) (dNTPαS) have been synthesized as Sp and Rp racemic mixtures using the methodology of Ludwig and Eckstein (J. Org. Chem. 54:631, 1989). In this exemplary synthetic scheme, unprotected nucleosides can be reacted with 2-chloro-4H-1,3,2-benzodioxaphosphorin-4-one, which phosphitylates the 5'-hydroxyl group. Subsequent reaction with pyrophosphate yields cyclic triphosphate derivatives which are reactive to sulfur, yielding mixtures of Rp and Sp nucleoside 5'-O-(1-thiotriphosphates), i.e., α-thiotriphosphates. The products can be purified by DEAE-Sephadex chromatography and identified by NMR spectroscopy (by characteristic Rp or Sp chemical shifts).

As is shown in the examples below, pure Rp and Sp nucleoside-5'-O-(1-thiotriphosphates) diastereomers can be readily isolated on a preparative scale using, for example, reverse phase HPLC chromatography. Such HPLC-isolated nucleotide diastereomers can be further characterized by analytical HPLC comparisons with commercial samples of such Rp and Sp nucleoside 5'-O-(1-thiotriphosphates) diastereomers.

Enzymatic synthesis of sequence-specific natural oligonucleotides, i.e., natural phosphodiester oligonucleotides, can be effected by the use of an appropriate nuclease in the presence of a template and primer. In a like manner, racemic mixtures of phosphorothioate oligonucleotides having chirally mixed intersugar linkages can be synthesized. According to the present invention, such enzymatic synthesis can also be expanded to include the synthesis of sequence specific phosphorothioate oligonucleotides having substantially chirally pure intersugar linkages by utilizing enantiomerically pure all-Sp or all-Rp nucleoside 5'-O-(1-thiotriphosphates) as substrates for appropriate nucleases in the presence of a sequence-specific template and a primer. For example, commercially available DNA polymerase Sequenase™ (U.S. Biochemical, Inc., Cleveland, Ohio) may be used to synthesize phosphorothioate oligonucleotides using a phosphodiester oligonucleotide template and a racemic phosphorothioate oligonucleotide primer. Using this polymerase both phosphodiester and phosphorothioate primers may be extended.

Yields of enzymatically synthesized phosphorothioate oligonucleotides can be optimized by repetitive additions of template and primer, by repetitive additions of polymerase, by repetitive additions of nucleoside triphosphates or by combinations of some or all of these. For instance, repetitive additions of template and primer results in maximizing yields via an enzymatic cascade. Further optimization can be achieved by pre-hybridization of template and primer together in system buffer, followed by cooling and addition of nucleoside triphosphates and polymerase.

A suitable polymerase may be selected to yield either DNA or RNA phosphorothioate oligonucleotides. Such polymerases include but are not necessarily limited to T7 DNA polymerase, modified T7 DNA polymerases such as the above referenced Sequenase™, *E. coli* DNA polymerase, DNA poly Klenow fragment polymerase, *M. luteus* polymerase, T4 bacteriophage polymerase, modified T4 DNA polymerase, T7 RNA polymerase and *E. coli* RNA polymerase.

The enzymatic synthesis proceeds with inversion of configuration about the chiral center of the phosphorous atom. Thus, use of all Sp α-thiotriphosphates yields substantially all Rp phosphorothioate oligonucleotides while use of all Rp α-thiotriphosphates yields substantially all Sp phosphorothioate oligonucleotides. In an alternate embodiment of the invention, phosphorothioate oligonucleotides may be synthesized from racemic mixtures of nucleoside-5'-O-(1-thiotriphosphates) utilizing metal ions in reaction solutions to promote preferential incorporation of one or the other of the chiral α-thiotriphosphates. As noted above, polymerase synthesis of phosphorothioate oligonucleotides is accomplished with inversion of configuration about the chiral center of the precursor nucleoside-α-thiotriphosphate. While not wishing to be bound by theory, it is believed that optimization of an all Rp configuration may be accomplished by addition of a high concentration of magnesium ion in the reaction buffer utilizing, for instance, an *E. coli* polymerase. In a like manner, again while not wishing to be bound by theory, an all Sp configuration might be obtained by utilizing a high manganese ion concentration in the reaction buffer.

In accordance with the present invention, "substantially all" is meant to include all oligonucleotides in which at least 75% of the intersugar linkages are chirally pure. More preferably, oligonucleotides having from about 85% to about 100% chirally pure intersugar linkages are substantially chirally pure. Most preferably, oligonucleotides having from about 95% to about 100% chirally pure intersugar linkages are substantially chirally pure.

Phosphorothioate oligonucleotides of the present invention can be contrasted with both natural phosphodiester oligonucleotides and racemic phosphorothioate nucleotides as to their effects on hybridization, nuclease resistance and RNAse H activity. In like manner, pure phosphorothioate oligonucleotides having substantially chirally pure intersugar linkages may also be assessed for their ability to increase effectiveness of therapy in in vivo test systems. Such increase in effectiveness of therapy might include attributes such as pharmacokinetics or metabolism, toxicology, disposition (i.e., absorption and distribution), and species comparisons.

Homopolymers having all Rp or all Sp intersugar linkages have been useful for initial studies of stability and other characteristics. However, these oligonucleotides have little use therapeutically as they are not specific for target molecules. Phosphorothioate oligonucleotides having specific sequences are necessary in order to specifically hybridize to target nucleic acids.

Sequence-specific phosphorothioate oligonucleotides having substantially chirally pure intersugar linkages are useful to increase the thermodynamic stability of heteroduplexes with target RNA and DNA and to elicit RNase H activity.

Radiolabeling can be used to assist in the identification of phosphorothioate oligonucleotides having substantially chirally pure intersugar linkages. For racemic phosphorothioate oligonucleotides synthesized on an automated synthesizer, [$^{35}$S] (radiolabeled elemental sulfur) can be used for oxidation of the hydrogen-phosphonate oligomers obtained from the synthesizer. Labeling of enzymatically synthesized phosphorothioate oligonucleotides can be accomplished with [α-$^{32}$P]ATP and ligase or [α-$^{35}$S]ATPs in the polymerase reaction. Also, radiolabeled nucleoside triphosphates can be used in probe and sequencing analysis. Autoradiograms are prepared in standard manners.

Templates of the present invention are most preferably areas of nucleic acid sequence which direct synthesis of disease-potentiating proteins. Short oligonucleotides that base pair to a region of said template oligonucleotide act as primers which form the starting point for oligonucleotide synthesis by polymerases.

Phosphorothioate oligonucleotides having substantially chirally pure intersugar linkages may be synthesized using a primer which may be selected to have a site thereon that is susceptible to nuclease cleavage, for example, restriction endonuclease cleavage. Said cleavage site may be located at the 3' end of said primer. Cleavage at said site by an appropriate restriction endonuclease results in oligonucleotides deriving a first 5' end nucleoside from said primer. Additional nucleosides of said phosphorothioate oligonucleotides of the present invention are those nucleoside chiral thiotriphosphates added via enzymatic means.

By selecting appropriate restriction nucleases in conjunction with selected primers, various 5'-terminal nucleosides of desired phosphorot-hioate oligonucleotides are appropriately positioned at the 5' end of a phosphorothioate nucleotide. Thus, any endonuclease recognition site can be designed as long as the staggered cut results in one nucleoside from the primer being the first 5' nucleoside of the newly synthesized sequence specific phosphorothioate oligonucleotide of the invention. This results in the generation of different nucleosides on 5' ends of enzymatically synthesized phosphorothioate oligonucleotides of the invention.

Upon completion of enzymatic extension of said primer on an appropriate template of a desired sequence, phosphorothioate oligonucleotides of the invention may be released from said primer by use of appropriate nuclease. For example, for incorporation of a guanosine nucleoside at the 5' end of desired phosphorothioate oligonucleotides, a primer having an CTGCAG sequence at its 3' terminal end may be used. Use of a Pst 1 restriction nuclease then may cleave the A-G linkage. The guanosine nucleoside component of this A-G linkage may thus incorporated as a 5' terminal nucleoside of desired phosphorothioate oligonucleotides. Other restriction endonuclease include but are not limited to BamH1, Smal and HinD III restriction endonucleases.

Oligonucleotides still associated with said template may be dissociated from said template and then purified by gel electrophoresis and/or chromatography. For example, suitable purification can be accomplished utilizing standard polyacrylamide/urea gel electrophoresis coupled with Sep-Pac (Millipore, Miford, Mass.) chromatography. Another useful chromatographic technique that may be employed is HPLC chromatography.

Chiral phosphorothioate oligonucleotides of the present invention may also be chemically synthesized via 1,3,2-oxathiaphospholane intermediates as described by Stec et al. (*Nucleic Acids Res.* 19:5883, 1991) and Stec and Lesnikowski (In: *Protcols for Oligonucleotides and Analogs* (*Methods in Molecular Biology*, Volume 20), S. Agrawal, Ed., p. 285, Humana Press, Totawa, N.J., 1993).

Phosphorothioate oligonucleotides having substantially chirally pure intersugar linkages which are synthesized according to methods of the present invention may be analyzed by a number of methods. For example, configuration analysis of resulting sequence-specific phosphorothioate oligonucleotides having substantially chirally pure all Sp or all Rp intersugar linkages may be determined by the use of [$^{31}$P] NMR chemical shifts. Such chemical shifts have been used to identify the Rp epimer of a phosphorothioate dinucleotide (Ludwig and Eckstein, *J. Org. Chem.* 54:631, 1989).

The fidelity of sequences of phosphorothioate oligonucleotides of the invention can be determined using the sensitivities of heteroduplexes to Si nuclease.

The sequence of the phosphorothioate oligonucleotides can be further substantiated by labeling the 3'hydroxyl groups of phosphorothioate oligonucleotides with [alpha-$^{32}$P]cordycepin triphosphate, i.e., 3' -deoxyadenosine-5'-triphosphate. The resultant oligonucleotides may be subjected to enzymatic degradation.

The relative ability of phosphorothioate oligonucleotides having substantially chirally pure intersugar linkages to bind to complementary strands is compared by determining the melting temperature of a hybridization complex of a phosphorothioate oligonucleotide having substantially chirally pure intersugar linkages and its complementary strand. The melting temperature ($T_m$), a characteristic physical property of double helixes, denotes the temperature in degrees centigrade at which 50% helical versus coiled (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non Watson-Crick base pairing has a strong destabilizing effect on the $T_m$. Consequently, as close to optimal fidelity of base pairing as possible is desired to have optimal binding of an oligonucleotide to its targeted RNA.

Phosphorothioate oligonucleotides of the invention can also be evaluated for their resistance to the degradative ability of a variety of exonucleases and endonucleases. Phosphorothioate oligonucleotides may be treated with nucleases and then analyzed, as for instance, by polyacrylamide gel electrophoresis (PAGE) followed by staining with a suitable stain such as Stains All™ (Sigma Chem. Co., St. Louis, Mo.). Degradation products may be quantitated using laser densitometry.

Fetal calf and human serum may be used to evaluate nucleolytic activity on phosphorothioate oligonucleotides having substantially chirally pure intersugar linkages. For instance, a phosphorothioate oligonucleotide having substantially all Rp intersugar linkages may be evaluated in this manner. Testing on combinations of 3' or 5' end capped (having one or several phosphorothioate linkages per cap) molecules may be used to establish a combination that yields greatest nuclease stability. Capping can be effected by chemically synthesizing the cap portion of a sequence using purified Rp monomers followed by incorporation of said cap into oligonucleotides on the DNA synthesizer. Analysis involving capping can determine the importance of chirality on nucleolytic stability and the number of linkages required to obtain maximum stability.

The sensitivity of phosphorothioate oligonucleotide-RNA heteroduplexes to the catalytic activity of RNase H can also be assessed. A phosphorothioate oligo- nucleotide can be incubated with a radiolabeled target mRNA (synthesized as for instance via T7 RNA polymerase) at various temperatures for hybridization. Heteroduplexes can then be incubated at 37° C. with RNase H from *E. coli* according to the procedure of Minshull and Hunt (*Nucl. Acid Res.* 14:6433, 1986). Products may then be assessed for RNase H activity by Northern Blot analysis wherein products are electrophoresed on a 1.2% agarose/formaldehyde gel and transferred to nitrocellulose. Filters may then be probed using a random primer [$^{32}$P]-labeled cDNA complementary to target mRNA and quantitated by autoradiography. Comparisons between different phosphorothioate analogs can be made to determine the impact of chirality on the ability to act as a substrate for RNase H when complexed to RNA.

Comparisons of the susceptibility of heteroduplexes to the catalytic action of *E. coli* RNase H and mammalian RNAse H can be performed. Heteroduplexes can be incubated in rabbit reticulocyte lysates under conditions of translation and assayed via Northern blot analysis for catalytic cleavage of mRNA by endogenous RNase H. This allows for determination of the effects of chirality on mammalian RNAse H activity.

Phosphorothioate oligonucleotides having substantially chirally pure intersugar linkages can also be evaluated for inhibition of gene expression in cell culture model systems. To determine if a phosphorothioate oligonucleotide having substantially pure chirally pure intersugar linkages is more potent or a more specific inhibitor of gene expression, a phosphorothioate oligonucleotide having substantially chirally pure intersugar linkages designed to target reporter genes may be synthesized and tested in cell culture models of gene expression. The use of the vector pSV2CAT has previously been described to measure antisense effects on gene expression (Henthorn et al., *Proc. Natl. Acad. Sci.* (*USA*) 85:6342, 1988). This vector contains the bacterial chloramphenicol acetyl transferase gene under regulatory controls of the SV40 promoter. Utilizing a 15-mer phosphorothioate oligonucleotide having all Rp intersugar linkages of a sequence complementary to the initiation of translation of the CAT mRNA, pSV2CAT may be transfected into HeLa cells and, following treatment of the cells for 48 hr with a phosphorothioate oligonucleotide having all Rp intersugar linkages, CAT activity may then be assayed in the cells. The activity of a phosphorothioate having substantially chirally pure intersugar linkages in inhibition of gene expression may then be compared directly with a chemically synthesized random phosphorothioate having diastereomeric intersugar linkages and natural phosphodiester oligonucleotides of the same sequence.

The vector pSV2APAP (Marcus-Sekura et al., *Nucl. Acids Research* 15:5749, 1987) contains the mammalian placental alkaline phosphatase gene (PAP). This can also be used as a reporter for measuring antisense effects on gene expression. PAP has advantages over CAT as a reporter gene in that it is a mammalian gene, rather than a bacterial gene that contains introns and other RNA processing signals. It is presently believed that PAP expression mimics more closely the events in natural mammalian gene expression. A 15-mer phosphorothioate oligonucleotide having substantially chirally pure intersugar linkages as described above for the CAT mRNA can be examined in parallel with chemically synthesized racemic phosphorothioate and natural phosphodiester oligonucleotides having similar sequences. The PAP and CAT reporter constructs are used as controls in reciprocal experiments to test for non-specific effects on gene expression.

Additionally, phosphorothioate oligonucleotides having substantially chirally pure intersugar linkages can be evaluated as to their ability to act as inhibitors of RNA translation in vivo. Various therapeutic areas can be targeted for such manipulation by oligonucleotides of the present invention. One therapeutic area is hepatitis caused by Hepatitis C virus (HCV). The following phosphorothioate oligonucleotides have application in the treatment of HCV hepatitis: Oligo #259, CCTTTCGCGACCCAACACTA (SEQ ID NO:122), Oligo #260, GCCTTTCGCGACCCAACACT (SEQ ID NO:123), Oligo #270, GTACCACAAGGCCTTTCGCG (SEQ ID NO:124), Oligo #330, GTGCTCATGGTGCACGGTCT (SEQ ID NO:125) and Oligo #340, TTTAGGATTCGTGCTCATGG (SEQ ID NO:126). Another therapeutic area inflammatory diseases mediated by intercellular cell adhesion molecule (ICAM-1). Oligonucleotides having application in the treatment of inflammatory diseases include: ISIS-2302, GCCCAAGCTGGCATCCGTCA (SEQ ID NO:127). Another therapeutic area includes infections caused by cytomegalovirus (CMV). ISIS-2922 is a phosphorothioate oligonucleotide having application in the treatment of CMV retinitis, and has the sequence GCGTTTGCTCTTCTTCTTGCG (SEQ ID NO:128). Another therapeutic area includes cancers mediated by protein kinase C-α (PKC-α). ISIS-3521 is a phosphorothioate oligonucleotide having application in the treatment of such cancers, and has the sequence GTTCTCGCTGGTGAGTTTCA (SEQ ID NO:2). A further therapeutic area includes C-raf kinase-mediated cancers. ISIS-5132 is a phosphorothioate oligonucleotide having application in the treatment of such cancers, and has the sequence TCCCGC-CTGTGACATGCATT (SEQ ID NO:130). A still further therapeutic area includes cancers mediated by Ha-ras or Ki-ras. The following phosphorothioate oligonucleotides have application in the treatment of such cancers: ISIS-2503, TCCGTCATCGCTCCTCAGGG (SEQ ID NO:131), ISIS-2570, CCACACCGACGGCGCCC (SEQ ID NO:132), and ISIS-6957, CAGTGCCTGCGCCGCGCTCG (SEQ ID NO:133). In the above sequences, individual nucleotide units of the oligonucleotides are listed in a 5' to 3' direction from left to right.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for cancer treatment. Examples of such chemotherapeutic agents include but are not limited to daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., pp. 1206–1228, Berkow et al., eds., 1987, Rahay, N.J., 1987). When used with the compounds of the invention, such chemotherapeutic agents may be used individually, sequentially (e.g., 5-FU for a period of time followed by MTX), or in combination with one or more other such chemotherapeutic agents (e.g., 5-FU and MTX, or 5-FU and radiotherapy). In another preferred embodiment of the invention, a first antisense oligonucleotide targeted to one PKC isozyme is used in combination with a second antisense oligonucleotide targeted to a second PKC isozyme in order to inhibit the activities of two functionally interchangeable PKC isozymes molecules at the same time.

Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1
Synthesis of Oligonucleotides with Racemic Intersugar Linkages

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For racemic phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl phosphorothioate oligonucleotides may be prepared by slight modifications of this procedure. 2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems, Foster City, Calif.) and deblocking in concentrated ammonium hydroxide at 55° C. for 18 hours, the oligonucleotides were purified by precipitation twice out of 0.5 M NaCl with 2.5 volumes ethanol. In some instances, the ethanol precipitation step was preceded by chromatography on an oligonucleotide purification column (OPC; ABI, Foster City, Calif.) or high pressure liquid chromatography (HPLC) using a Beckman System Gold HPLC column. Purified oligonucleotides are assessed for final purity by analytical HPLC or analytical gel electrophoresis (20% acrylamide, 8 M urea, 45 mM Tris-borate buffer, pH 7.0). The authenticity of the oligonucleotide sequence was assessed by oxidation with iodine in pyridine/water and standard sequencing methods. These phosphorothioate oligonucleotides contain a mixture of all possible combinations of Rp and Sp isomers at each phosphorus linkage.

The PKC-α oligonucleotides tested are presented in Table 1. Sequence data are from the cDNA sequence published by Finkenzeller et al. (*Nucl. Acids Res.* 18:2183, 1990; Genbank accession number X52479). The sequence numbers given under the oligonucleotides are relative to the first residue to be sequenced on the cDNA, which is 28 residues upstream of the ATG start codon. Sequences of non-α PKC oligonucleotides are presented in Examples 13–17.

TABLE 1

| SEQ ID | Sequence | | Target | ISIS # |
|---|---|---|---|---|
| 1 | CCC CAA CCA CCT CTT GCT CC<br>19                    1 | | 5'<br>Untranslated | 3520 |
| 2 | GTT CTC GCT GGT GAG TTT CA<br>2063               2044 | | 3'<br>Untranslated | 3521 |
| 3 | AAA ACG TCA GCC ATG GTC CC<br>41                  22 | | Translation<br>init. codon | 3522 |

TABLE 1-continued

OLIGONUCLEOTIDES TARGETED TO HUMAN PKC-α

| SEQ ID | Sequence | Target | ISIS # |
|---|---|---|---|
| 4 | GGA TTC ACT TCC ACT GCG GG<br>2109                        2090 | 3' Untranslated | 3526 |
| 5 | GAG ACC CTG AAC AGT TGA TC<br>2211                        2192 | 3' Untranslated | 3527 |
| 6 | CCC GGG AAA ACG TCA GCC AT<br>47                        28 | Translation init. codon | 3674 |
| 7 | CTG CCT CAG CGC CCC TTT GC<br>110                       91 | Internal (C1) domain | 3682 |
| 8 | AGT CGG TGC AGT GGC TGG AG<br>193                      174 | Internal (C1) domain | 3686 |
| 9 | GCA GAG GCT GGG GAC ATT GA<br>480                      461 | Internal (C1) domain | 3687 |
| 10 | GGG CTG GGG AGG TGT TTG TT<br>2080                      2061 | 3' Untranslated | 3695 |
| 11 | CAC TGC GGG GAG GGC TGG GG<br>2098                      2079 | 3' Untranslated | 3875 |
| 12 | AGC CGT GGC CTT AAA ATT TT<br>2137                      2118 | 3' Untranslated | 3878 |
| 13 | ATT TTC AGG CCT CCA TAT GG<br>2168                      2149 | 3' Untranslated | 3879 |
| 14 | AAG AGA GAG ACC CTG AAC AG<br>2217                      2198 | 3' Untranslated | 3884 |
| 15 | GAT AAT GTT CTT GGT TGT AA<br>2235                      2216 | 3' Untranslated | 3885 |
| 16 | ATG GGG TGC ACA AAC TGG GG<br>2027                      2008 | Internal (C3) domain | 3886 |
| 17 | GTC AGC CAT GGT CCC CCC CC<br>36                        17 | Translation init. codon | 3890 |
| 18 | CGC CGT GGA GTC GTT GCC CG<br>63                        44 | Internal (V1) domain | 3891 |
| 19 | TCA AAT GGA GGC TGC CCG GC<br>1643                      1624 | Internal (C3) domain | 3892 |
| 20 | TGG AAT CAG ACA CAA GCC GT<br>2151                      2132 | 3' Untranslated | 3947 |

Example 2

Isolation of Rp or Sp 5'-O-(1-thiotriphosphate) Nucleosides

In order to isolate Sp or Rp 5'-O-(1-thiotriphosphate) nucleosides, 5'-O-(1-thiotriphosphate) deoxynucleosides and ribonucleosides are isolated using C-18 reverse phase high performance liquid chromatography (HPLC) using columns packed with ODS Hypersil (Shandon Southern, Runcon, UK) and eluted with an isocratic mixture of solvent A (30 mM potassium phosphate containing 5 mM tetrabutylammonium ion, pH 7.0) and solvent B (5 mM tetrabutylammonium hydroxide in methanol). Alternatively, effective separation is achieved using 100 mM triethylammonium bicarbonate, pH 7.5, containing a linear gradient of acetonitrile from 0 to 15% over 20 minutes. To establish the purity of such HPLC separated enantiomers the HPLC separated Sp and Rp deoxynucleotide enantiomers are compared to commercially available deoxynucleoside 5'-O-(1-thiotriphosphates) available from E.I. Dupont, Wilmington, Del.

Example 3

Enzymatic Synthesis of Substantially Chirally Pure Oligonucleotides

Enzymatic synthesis of a substantially all or all Rp phosphorothioate extension of a racemic phosphorothioate oligonucleotide primer is effected using the modified T7 DNA polymerase I, Sequenase™ (U.S. Biochemicals Corp, Cleveland, Ohio). This T7 DNA polymerase is used to extend an 18 mer phosphorothioate oligonucleotide primer hybridized to a 21-mer natural phosphodiester oligonucleotide. 30 picomoles (pmol) of primer and template in a 1× Sequenase™ reaction buffer (U.S. Biochemicals Corp., Cleveland, Ohio) (final vol 10 μL) are heated for 5 minutes at 95° C. and slowly cooled to room temperature. 180 pmol of deoxy 5'-[α-$^{35}$S]cytidine triphosphate and Sequenase enzyme (U.S. Biochemicals Corp., Cleveland, Ohio) are added and incubated at 37° C. for 20 minutes. The product is analyzed via polyacrylamide gel electrophoresis (PAGE) using a 20% polyacrylamide/7 M urea denaturing gel. The autoradiograph of the product is compared to a control reaction absent primer/template. The final product is subjected to further characterization by, for example, enzymatic degradation. One such degradation is snake venom phosphatase degradation. A snake venom phosphatase degradation of dinucleoside monophosphorothioate synthesized using E. coli DNA polymerase I shows the dinucleoside to be of the Rp configuration.

In order to effect a large scale enzymatic synthesis of a sequence specific (SEQ ID NO:134) all Rp phosphorothioate oligonucleotide, a 55-mer natural phosphodiester template and a 41-mer natural phosphodiester primer. The template sequence was 5'-GTACTTGCATAGTCGATCGGAAAATAGGGTTCT CATCTCCCGGGATTTGGTTGAG (SEQ ID NO:135), and the primer sequence was 5'-CTCAACCAAATCCCGGGATGAGAACCCTATT TTCCGATC (SEQ ID NO:136). The template:primer duplex was designed to have an unpaired sequence complementary to the desired specific sequence, 5'-CGACTATGCAAGTAC (SEQ ID NO:134). A Sequenase™ buffer (U.S. Biochemicals Corp., Cleveland, Ohio) diluted from 5× to 1× was used. The template and primer, both at concentrations of 20 nM are added to 40 μL of this buffer. The template and primer were hybridized at 95° C. for 5 minutes and cooled to room temperature. After cooling the buffer was adjusted to 7 mM DTT. 20 μL of 1:8 diluted Sequenase™ enzyme and 320 μM each of Sp GTPαS, CTPαS, ATPαS and TTPαS were then added. The reaction solution was adjusted to 140 μL with H$_2$O. It was incubated at 37° C. for 18 hours. The reaction solution was extracted 2× with a like volume of phenol in a standard manner and precipitated in a standard manner by treatment with 2.5 volumes of 100% ethanol at −20° C., peltized, washed with 500 μL of 70% ethanol, peltized again and dried. The precipitate was suspended in 20 μL H$_2$O for 30 minutes then adjusted to 1 mM CaCl$_2$, 25 mM Tris HCl pH 8.0 in 40 μL H$_2$O. The solution was maintained at 95° C. for 5 minutes and snap cooled, i.e., very quickly cooled with ice. The template and primer were removed from the synthesized oligonucleotide by the addition of 4.6 μM DNase I and incubation at 37° C. for 10 minutes. The reaction mixture was phenol extracted 2× and precipitated with ethanol as above. The precipitate was resuspended in H$_2$O and purified using 20% polyacrylamide/7 M urea gel electrophoresis coupled with SepPak™ chromatography (Millipore, Milford, Mass.).

In an alternate large scale enzymatic synthesis of a sequence specific all Rp phosphorothioate oligonucleotide, Pvu 1 restriction nuclease (Life Technologies, Inc., Gaithersburg, Md.) was used to cleave the primer-bound phosphorothioate oligonucleotide at the restriction site. The desired CGACTATGCAAGTAC (SEQ ID NO:134) phosphorothioate oligonucleotide was purified using polyacrylamide/7 M urea gel electrophoresis coupled with SepPak™ chromatography (Millipore, Milford, Mass.). Yields were optimized using enzymatic cascade effected by repetitive template-primer addition throughout the reaction. The cascade augmented synthesis yielded 75 A$_{260}$ units of the CGACTATGCAAGTAC (SEQ ID NO:134) all Rp configuration phosphorothioate oligonucleotide from a 20 mL reaction.

Example 4
Chemical Synthesis of Diastereomerically Pure Nucleoside Oxaphospholanes and Oligonucleotides Compounds 1, 2 and 3 are synthesized according to the procedure of Stec et al. (Nucleic Acids Res., 19:5883, 1991) and Stec and Lesnikowski (Methods in Molecular Biology, S. Agrawal, Ed., Volume 20, p. 285, 1993).

In order to synthesize 2-chloro-1,3,2-oxathiaphospholane (compound 1), a mixture of pyridine (1 mol), benzene (400 mL), 2-mercaptoethanol (0.5 mol) and phosphorus trichloride (0.5 mol) are stirred at room temperature for 30 minutes. Pyridinium chloride is filtered off, solvent is evaporated under reduced pressure and crude product is purified by distillation under reduced pressure. The fraction boiling at 70–72° C./20 mm Hg is collected and characterized by $^{31}$P NMR.

In order to synthesize N,N-diisopropylamino-1,3,2-oxathiaphospholane (compound 2), compound 1 (0.2 mol) is dissolved in n-pentane (300 mL) and diisopropylamine (0.4 mol) is added dropwise. The reaction mixture is stirred at room temperature for 30 minutes, after which diisopropylamine hydrochloride is filtered off, solvent is evaporated under reduced pressure and crude product is purified by vacuum distillation. Product 2 is obtained as the fraction boiling at 70° C./0.1 mm Hg and is characterized by 31P NMR and mass spectroscopy.

Compound 3, 5'-O-dimethoxytritylthymidine-3'-O[2-thiono-1,3,2-oxathiaphospholane, is prepared in the following manner. 5'-O-Dimthoxytritylthymidine (10 mmol) and 1H-tetrazole (11 mmol) are vacuum dried and dissolved in dichloromethane (25 mL). Compound 2 (11 mmol) is added to the solution and the reaction mixture is stirred at room temperature for 2 hours. Dried elemental sulfur (15 mmol) is added and the reaction mixture is stirred and left at room temperature for 16 hours. Unreacted sulfur is then filtered off and the filtrate is concentrated under reduced pressure. The residue is dissolved in chloroform (3 mL) and purified by silica gel (230–400 mesh) column chromatography, eluting first with chloroform, and next with chloroform:methanol (97:3). Individual diastereomeric species of compound 3 are obtained by column chromatography on silica gel. Compound 3 is dissolved in ethyl acetate and applied on a silica gel 60H column. Ethyl acetate is used as the eluting solvent, and elution is monitored by HPTLC (silica gel 60, ethyl acetate as the developing solvent). Fractions containing separated diastereomers of compound 3 are concentrated under reduced pressure and the residue is characterized by $^{31}$P NMR and HPLC (Lichrospher Si100, 5 μM, ethyl acetate as eluant, flow rate 3 mL/minute). The fast eluting fraction corresponds to the Sp diastereomer, and the slow eluting fraction is the Rp diastereomer.

In order to effect the stereospecific control of reactions between 5'-OH nucleosides and diastereomerically pure compound 3 in solid phase automated synthesis, the following procedure, modified from that of Stec et al., was carried out using an Applied Biosystems (Foster City, Calif.) model 380B automated DNA synthesizer. The reaction between a 5'-OH nucleoside and diastereomerically pure nucleoside oxathiaphospholane, such as compound 3, requires the use of 1,8-diazabicyclo(5.4.0)undec-7-ene (DBU) as the catalyst. Because the commercially available linker used for the attachment of oligonucleotide to support matrix in automated DNA synthesis is unstable to DBU, a modification is required in the linker. A suitable linker for oligonucleotide synthesis via the oxathiaphospholane method is a "succinic-sarcosinyl" linker that is resistant to DBU, and can be hydrolyzed by concentrated ammonium hydroxide at room temperature in less than 1 hour.

(A) Synthesis of 5'-O-dimethoxytritylnucleosides bound to solid matrix via "succinic-sarcosinyl" linker:

(1) N-Fmoc-sarcosine (Bachem Bioscience, Inc., Philadelphia, Pa.) (1.6 mmol) is added to long chain alkyl amine-CPG (LCA-CPG, Sigma, St. Louis, Mo.) (2 g) and dried under vacuum. Anhydrous DMF (5 mL), pyridine (0.5 mL) and DCC (2.4 mmol) are added and the reaction mixture is shaken at room temperature for 12 hours. The solvent is then filtered off and the support is washed with methanol:acetonitrile:pyridine (1:1:1, 3×20 mL). The N-Fmoc protecting group is removed by treating the support with 10 mL of a 10% solution of piperidine in pyridine. N-sarcosinylated LCA-CPG is washed with methanol:acetonitrile:pyridine (1:1:1, 3×20 mL) and dried under vacuum.

(2) 5'-O-Dimethoxytritylnucleoside is added to the sarcosinylated LCA-CPG obtained as described in (1) in the presence of DMF (2 mL), pyridine (0.2 mL) and DCC (50 mg). The reaction mixture is shaken at room temperature for 12 hours and then washed with methanol:acetonitrile:pyridine (1:1:1, 3×20 mL). After drying, the support is treated with N-methylimidazole:THF (1 mL) and acetic anhydride/lutidine (1 mL) for 15 minutes. The support is then washed with methanol:acetonitrile:pyridine (1:1:1, 3×10 mL), followed by acetonitrile (3×10 mL), and then dried under vacuum.

(B) Diastereomerically pure activated nucleosides are subsequently added onto the oligonucleotide attached to the sarcosinyl LCA-CPG support in the presence of a 300-fold molar excess of DBU. The diastereomers of activated nucleosides are separated by column chromatography [silica gel 60H, ethyl acetate is used as the eluting solvent, elution is monitored by HPTLC (silica gel 60, ethyl acetate as the developing solvent)] prior to use in the coupling reaction.

The synthetic protocol is described in Table 2. The diastereomeric purity of the phosphorothioate oligonucleotide can be determined by 31P NMR, by HPLC (Lichrospher Si100, 5 µM, ethyl acetate as eluant, flow rate 3 mL/minute), enzymatically or by electrophoretic methods.

TABLE 2

Chemical steps for one synthesis cycle

| Reagent or solvent | Purpose | Time (minutes) |
| --- | --- | --- |
| Trichloroacetic acid in dichloromethane (2:98) | Detritylation | 1.5 |
| Acetonitrile | Wash | 2 |
| Activated nucleoside (with DBU) in acetonitrile | Coupling | 10 |
| Acetonitrile | Wash | 2 |
| Acetic anhydride/lutidine in THF (1:1:8) and N-methylimidazole in THF (4:21) | Capping | 1 |
| Acetonitrile | Wash | 1 |

Example 5
Hybridization Analysis of Oligonucleotides with Chirally Pure Intersugar Linkages Short DNA or RNA molecules having nucleotide sequences complementary to the sequences of oligonucleotides with chirally pure intersugar linkages were prepared as follows. The synthesis of short complementary DNA oligonucleotides of natural phosphodiester linkages was performed utilizing standard automated synthesis on an ABI model 380B DNA Synthesizer. The oligonucleotides of correct length were purified by HPLC and sequenced by standard techniques.

T7 RNA polymerase was use for the synthesis of short, complementary RNA oligonucleotides for hybridization analysis. A large amount of T7 RNA polymerase at high concentrations was needed for the many cycles of initiation required to synthesize short RNAs. Due to this requirement, the T7 RNA polymerase was derived from a strain of E. coli that contained a T7 RNA polymerase expression vector, BL21/pAR1219, obtained from Brookhaven National Laboratory (Upton, N.Y.). The isolation yielded approximately 300,000 to 500,000 units of T7 RNA polymerase from 2 L of cells, absorbance value=1.2 $A_{600}$. This was sufficiently concentrated for synthesis of short (10–30 nucleotides) RNA species. For synthesis, a T7 promoter and a template containing the complementary target sequence and T7 promoter hybridization sequence were synthesized using the ABI synthesizer (ABI, Foster City, Calif.). Template and promoter were purified by HPLC to ensure that the correct species was present for enzymatic synthesis. Synthesized products were purified on a 20% polyacrylamide/8 M urea gel and sequenced by standard procedures.

In thermal denaturation experiments, oligonucleotides (either phosphorothioate oligonucleotides of the invention or otherwise) were incubated with either the complementary DNA or RNA oligonucleotides at a standard concentration of 4 µM for each oligonucleotide in 100 mM ionic strength buffer (89.8 mM NaCl, 10 mM Na-phosphate, pH 7.0, 0.2 mM EDTA). Samples were heated to 90° C. and the initial absorbance taken using a Guilford Response II spectrophotometer (Corning Inc., Corning, N.Y.). Samples were then slowly cooled to 15° C. and the change in absorbance at 260 nm monitored during the heat denaturation procedure. The temperature was elevated 1 degree/absorbance reading and the denaturation profile analyzed by taking the first derivative of the melting curve. Data was also analyzed using a two-state linear regression analysis to determine the $T_m$ and delta G. The results of these tests are shown in Table 3.

TABLE 3

THERMAL DENATURATION RESULTS

| Sequence | SEQ ID NO: | Complement | Tm |
| --- | --- | --- | --- |
| Natural phosphodiester | | | |
| CGA CTA TGC AAG TAC | 134 | DNA | 53.2 |
| CGA CTA TGC AAG TAC | 134 | RNA | 46.2 |
| Phosphorothioate with racemic intersugar linkages | | | |
| CGA CTA TGC AAG TAC | 134 | DNA | 46.0 |
| CGA CTA TGC AAG TAC | 134 | RNA | 36.5 |
| Phosphorothioate with chirally pure intersugar linkages | | | |
| CGA CTA TGC AAG TAC | 134 | DNA | 45.5 |
| CGA CTA TGC AAG TAC | 134 | RNA | 41.5 |
| GA CTA TGC AAG TAC | 129 | DNA | 44.5 |
| GA CTA TGC AAG TAC | 129 | RNA | 40.0 |

Filter binding assays are utilized to quantitate the binding stringencies of various phosphorothioate oligonucleotides, i.e., their tendencies to hybridize and form heteroduplexes with DNA or RNA which has been pre-bound to a filter. These assays require radiolabeled chirally pure oligonucleotides, which are synthesized as follows. Phosphorothioate oligonucleotides having all Rp intersugar linkages are synthesized by enzymatic methods from [$^{35}$S]-monomers that have been purified from Sp monomers. For automated synthesis of phosphorothioate oligonucleotides containing mixed chirality intersugar linkages, oligonucleotides are synthesized containing hydrogen phosphonates and then sulfurized in the presence of elemental [$^{35}$S] in a pyridine/carbon disulfide mixture. The resulting radiolabeled phosphorothioate oligonucleotide can be purified by OPC chromatography and HPLC. Target mRNAs are applied to nitrocellulose filters and baked at 80° C. for 2 hours, blocked and then hybridized with the radiolabeled phosphorothioate oligonucleotide. Binding stringency is assessed by quantitating radiolabeled oligonucleotide eluted from the filters after increases in temperature or increases in the ionic strength of an eluting buffer, as for instance, Tris NaCl buffer. Eluted oligonucleotides are also assessed for their mobility in an anion exchange HPLC protocol isocratically utilizing phosphate buffer. Results are compared to the mobility of standard oligonucleotides prepared having racemic mixtures of intersugar linkages.

Example 6
Nuclease Digestion of Oligonucleotides with Chirally Pure Intersugar Linkages Determination of the rate of nuclease degradation of the phosphorothioate oligonucleotides in media containing 10% fetal calf serum (FCS) was carried out in Dulbecco's Modified Essential Medium (DMEM) containing 10% heat inactivated FCS. Heat inactivation of the FCS was carried out at 55° C. for 1 hour prior to addition to media. Oligonucleotides having racemic and chirally pure intersugar linkages were separately tested for resistance to nuclease digestion. 66 μg/mL of each oligonucleotide were separately added to medium and incubated at 37° C., at the time intervals indicated in Table 2. 15 μL Aliquots were removed and added to 15 μL of 9 M urea in 0.1 M Tris-HCl (pH 8.3), 0.1 M boric acid and 2 mM EDTA. Aliquots were mixed by vortex and stored at −20° C. Polyacrylamide gel electrophoresis (PAGE) analysis was on 20% polyacrylamide/7 M urea slab gels. Following electrophoresis, gels were stained using "Stains All" (Sigma Chem. Co., St. Louis, Mo.). Following destaining, gels were analyzed via laser densitometry using an UltraScan XL device (Pharmacia LKB Biotechnology, Uppsala, Sweden). Integrations were performed and the data presented as the percentage decrease from full length (n) prior to incubation to n−1. These results are shown in Table 4 for the oligonucleotide sequence CGACTATGCAAGTAC (SEQ ID NO:134) having Rp chirally pure intersugar linkages.

TABLE 4

NUCLEASE DIGESTION RESULTS
Incubation in 10% fetal calf serum
Digestion of oligonucleotide of length n to length n − 1

| Time (hours) | Phosphorothioate with racemic intersugar linkages | Phosphorothioate with chirally pure intersugar linkages |
|---|---|---|
| 0 | 0 | 0 |
| 1 | 44 | 10 |
| 2 | 45 | 10 |
| 4 | 54 | 12 |
| 24 | 70 | 44 |
| 48 | 70 | 62 |

As is evident from Table 4, the phosphorothioate oligonucleotide having substantially chirally pure intersugar linkages showed greater resistance to nuclease degradation than did the phosphorothioate oligonucleotide having racemic intersugar linkages.

Example 7
RNase H Analysis of Oligonucleotides with Chirally Pure Intersugar Linkages Phosphorothioate oligonucleotides having racemic and substantially chirally pure intersugar linkages were analyzed for susceptibility to RNase H. Oligonucleotides (2-fold molar excess to RNA) and 5 μg (3.1 kb) in vitro synthesized mRNA (using T7 RNA polymerase promoter) were incubated in 5 μL RNase H hybridization buffer for 30 minutes at 60° C. Samples were slowly cooled to room temperature and then adjusted to 3.7 mg/mL BSA, 20 units E. coli RNase H (Promega), 142 mM DTT, 150 mM KCl, and 3 mM MgCl$_2$. Samples were incubated for 30 minutes at 37° C. Samples were then extracted with phenol, precipitated with ethanol, and analyzed by electrophoresis on 1.2% agarose gels following ethidium bromide staining. Markers were run on gels concurrently with the samples to determine approximate length of RNA samples.

Example 8
In Vitro Screening and Evaluation of Oligonucleotides Targeted to PKC-α

(A) PKC protein half-lives have been reported to vary from 6.7 hours to over 24 hours (Young et al., *Biochem. J.* 244:775, 1987; Ballester et al., *J. Biol. Chem.* 260:15194, 1985). These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., (*J. Biol. Chem.* 262:11852, 1987) lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Rockville, Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 μl DOTMA (Lipofectin reagent, BRL, Bethesda, Md.) was added. Oligonucleotides were added to a concentration of 1 μM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 μM) were added and the cells were incubated at 37° C. for 24 hours.

Cells were washed three times in phosphate-buffered saline (PBS) and cellular proteins were extracted in 120 μl sample buffer (60 mM Tris pH 6.8, 2% SDS, 10% glycerol, 10 mM dithiothreitol) and boiled for 5 minutes. Intracellular levels of PKC-α protein were determined by immunoblotting.

Cell extracts were electrophoresed on 10% SDS-PAGE mini-gels. The resolved proteins were transferred to Immobilon-P membrane (Millipore, Bedford, Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid, N.Y.) diluted to 0.2 μg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine, Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Figure 1A:
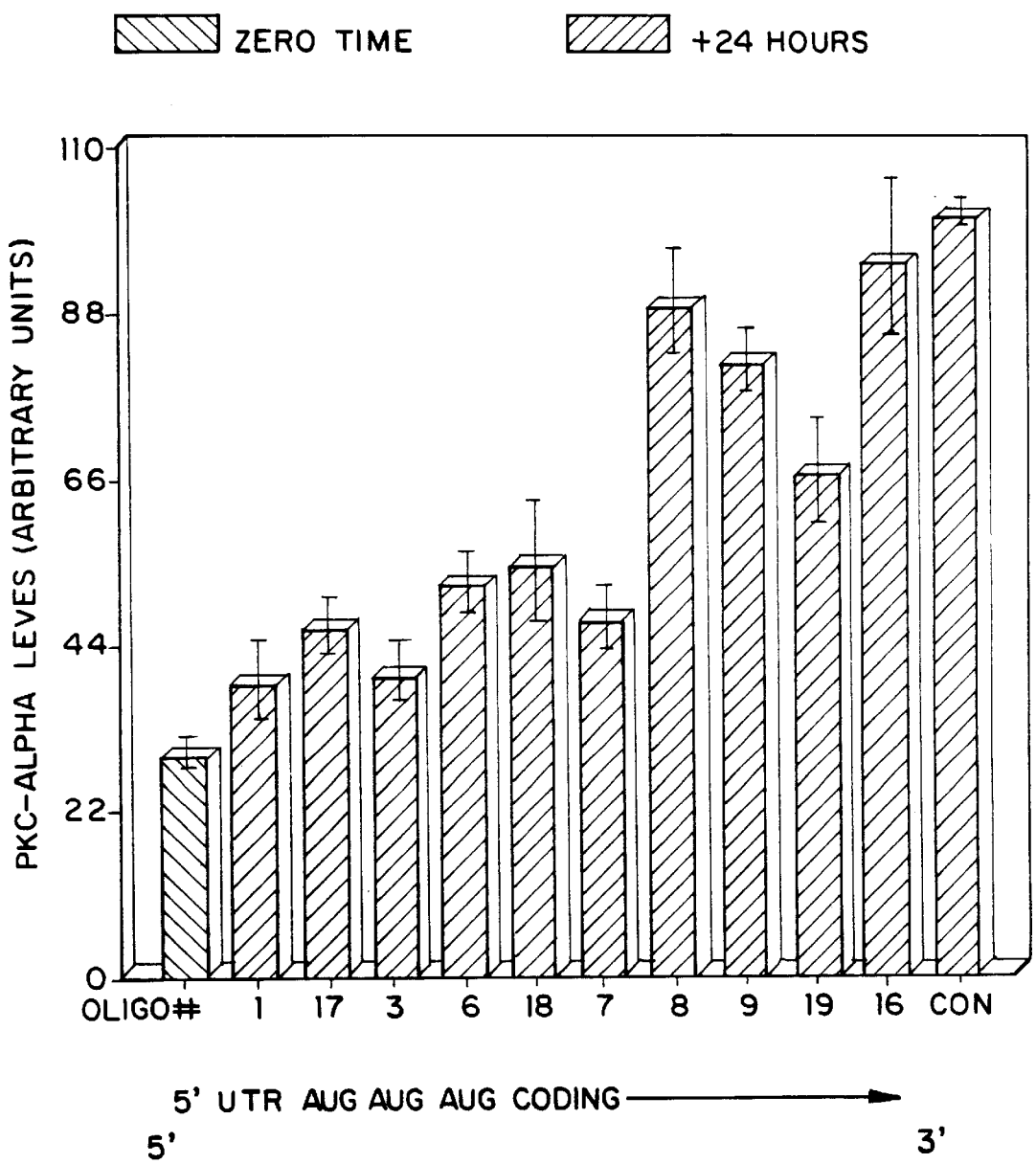
FIG. 1(*a*) and 1(*b*) are graphical depictions of the effects on PKC expression of antisense oligonucleotides hybridizable with PKC-α. Oligonucleotides are arranged by PKC target region, 5' to 3'.
Figure 1B:
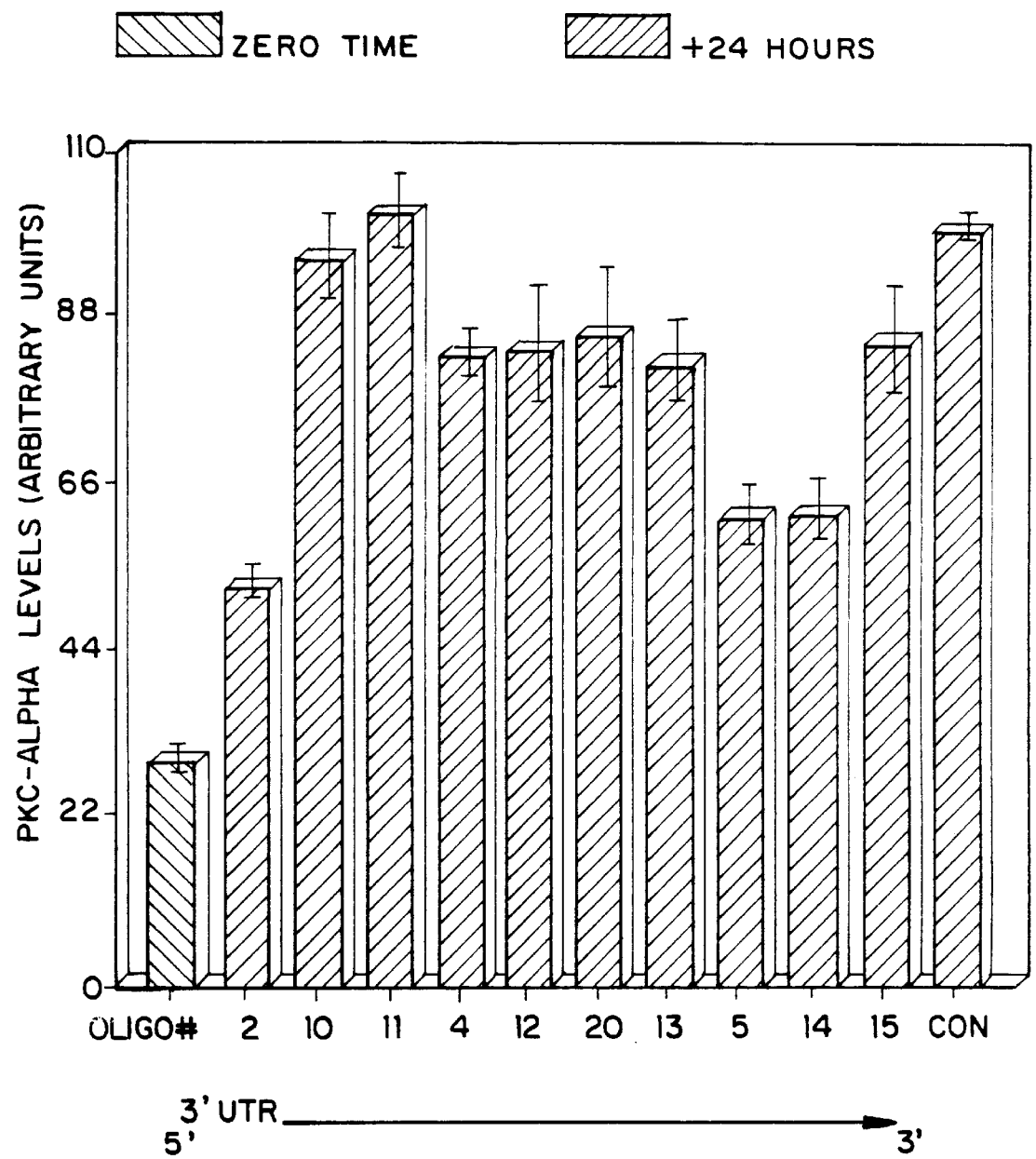

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (SEQ ID NOS:1, 3, 17, 7 and 6). The next most effective oligonucleotides are targeted toward the 3' untranslated region of the RNA (SEQ ID NOS:2, 5 and 14).

Figure 2:
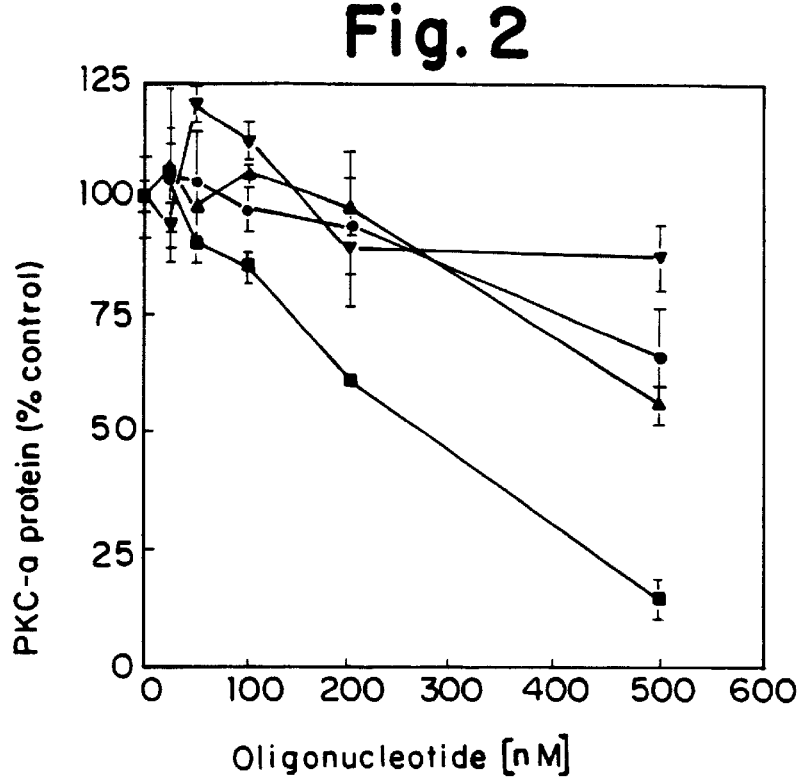
FIG. 2 is a line graph showing dose-dependent reduction of PKC-α protein levels after treatment of A549 cells with phosphorothioate, fully 2'-O-methyl oligonucleotides. Symbols: ▼=ISIS 4632 (SEQ ID NO:1); ■=ISIS 4649 (SEQ ID NO:3); ●=ISIS 4636 (SEQ ID NO:2); ▲=ISIS 4648 (SEQ ID NO:5).

(B) The results of a dose response evaluation of a series of phosphorothioate, fully 2'-O-methyl oligonucleotides having SEQ ID NO: 1, 2, 3 and 5 are shown in FIG. 2. A549 cells were treated with 500 nM PDBu for 18 hours to down regulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described above. Results were quantified with a phosphorimager (Molecular Dynamics, Sunnyvale Calif.) and are shown in FIG. 2 expressed as percent of control (saline treatment). ISIS 4649 (SEQ ID NO:3; squares) reduced PKC-α protein levels by 85–90% at 500 nM and had an $IC_{50}$ of approximately 260 nM.

Figure 3:
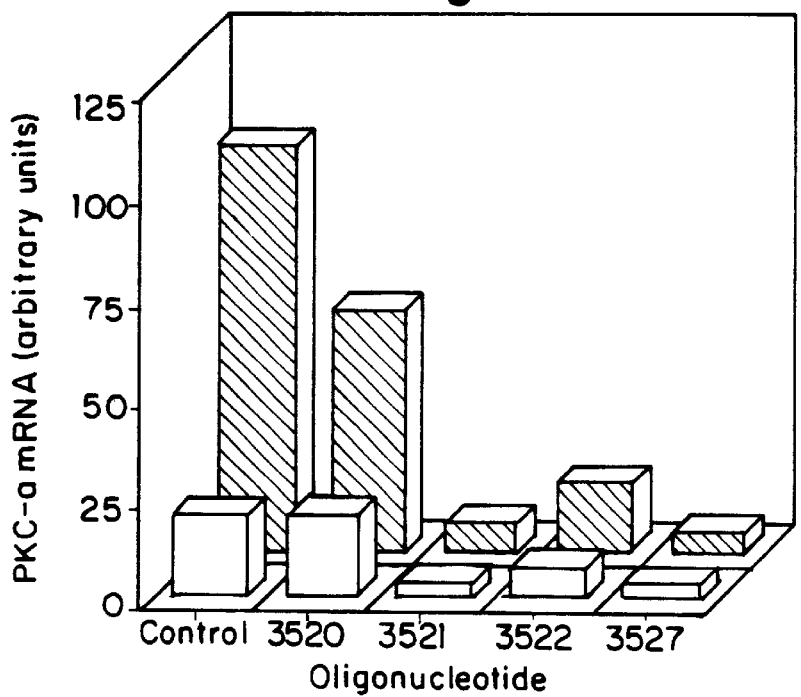
FIG. 3 is a bar graph showing reduction of PKC-α mRNA after treatment of A549 cells with oligonucleotides. Hatched bars represent the 8.5 kb transcript, plain bars represent the 4.0 kb transcript.

(C) In order to evaluate the effect of Oligonucleotides on PKC-α mRNA levels, the following procedure was used. A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$p radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). Results are shown in FIG. 3. Oligonucleotides 3521 (SEQ ID NO:2), 3522 (SEQ ID NO: 3) and 3527 (SEQ ID NO:5) gave better than 50% reduction of PKC-α mRNA levels. Oligonucleotides 3521 and 3527 gave approximately 80% reduction of the smaller transcript and over 90% reduction of the larger transcript.

Example 9
Chimeric (deoxy Gapped) 2'-O-methyl Oligonucleotides Targeted to PKC-α

Figure 4:
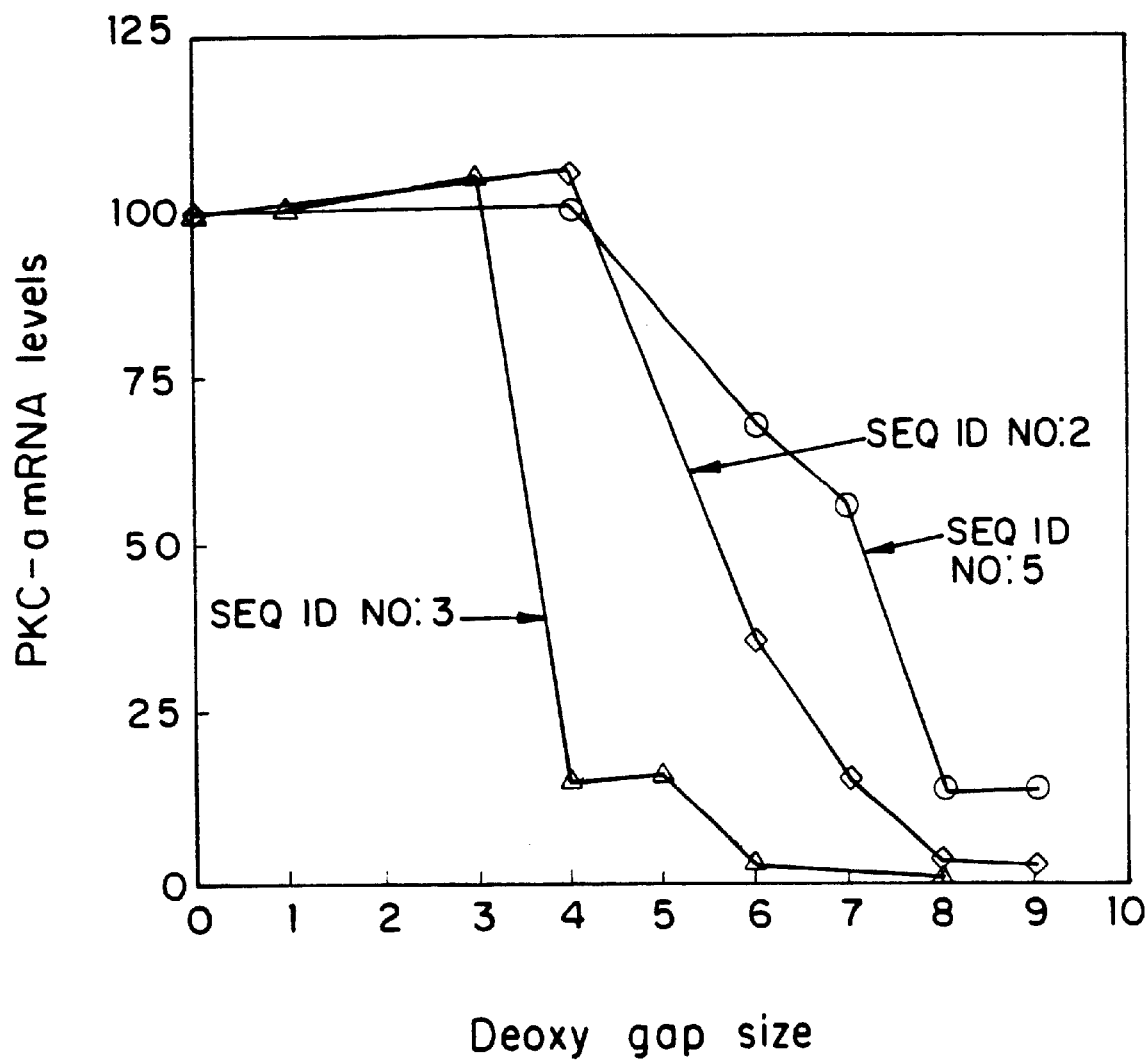
FIG. 4 is a line graph showing the relationship between deoxy gap length and activity of chimeric oligonucleotides against PKC.

Oligonucleotides 3521 (SEQ ID NO:2), 3522 (SEQ ID NO: 3) and 3527 (SEQ ID NO:5) were chosen for further study and modification. Oligonucleotides having these sequences were synthesized as uniformly phosphorothioate chimeric oligonucleotides having a centered deoxy gap of various lengths flanked by 2'-O-methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligonucleotide having SEQ ID NO:3 reduced PKC-α mRNA by approximately 83% with a deoxy gap length of four nucleotides, and gave nearly complete reduction of PKC-α mRNA with a deoxy gap length of six or more.

Figure 5:
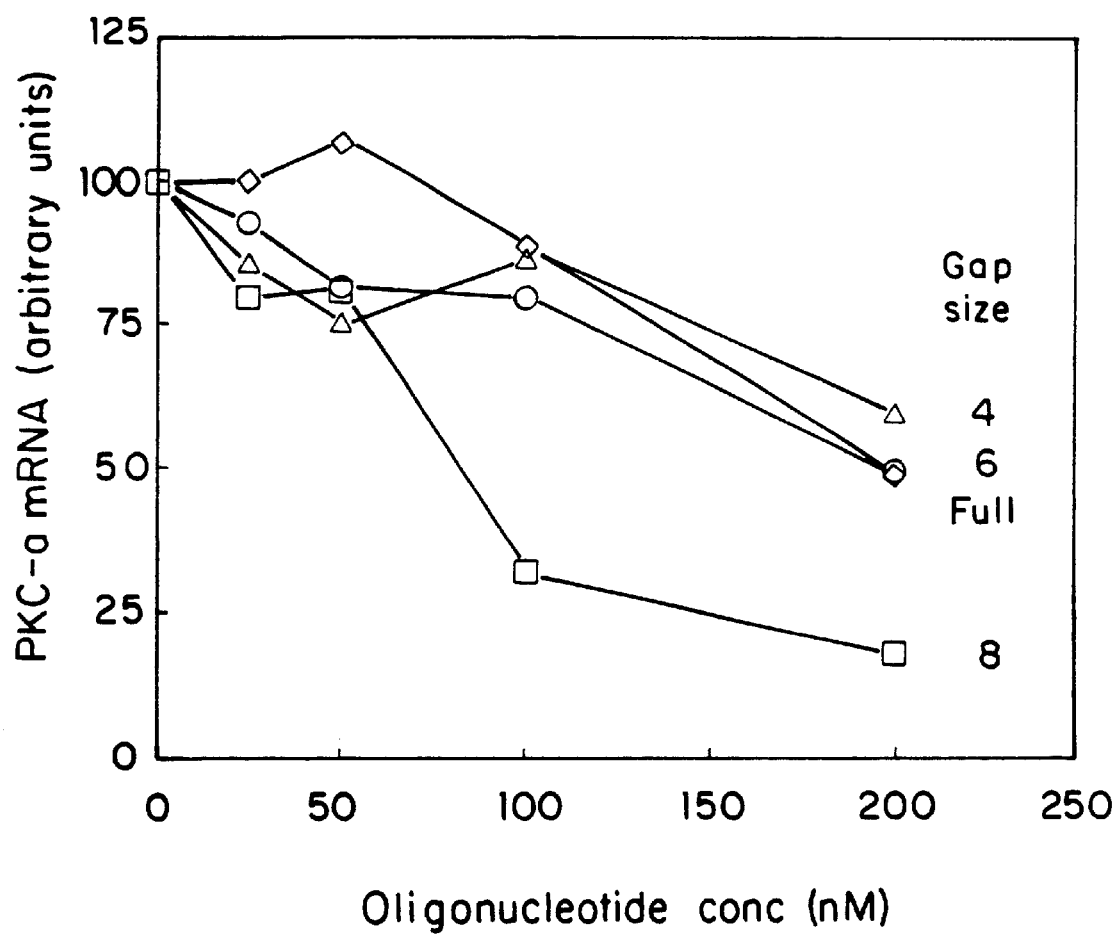
FIG. 5 is a line graph showing dose response curves for chimeric oligonucleotides (all SEQ ID NO:3) with different deoxy gap lengths.

Dose-response curves for these oligonucleotides are shown in FIG. 5. The 2'-O-methyl chimeric oligonucleotides with four- or six-nucleotide deoxy gaps have an $IC_{50}$ for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an $IC_{50}$ of approximately 85 nM.

Several variations of this chimeric oligonucleotide (SEQ. ID NO:3) were compared for ability to lower PKC-α mRNA levels. These oligonucleotides are shown in Table 5.

TABLE 5

CHIMERIC 2'-O-METHYL/DEOXY P=S OLIGONUCLEOTIDES

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5352 | AsAsAsAsCsGsTsCsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCsAsTsGoGoToCoCsC | 3 |
| 7024 | AsAoAoAoCoGsToCsAoGsCoCsAsTsGoGoToCoCsC | 3 | bold = 2'-O-methyl; s = P=S linkage, o = P=O linkage

Figure 6:
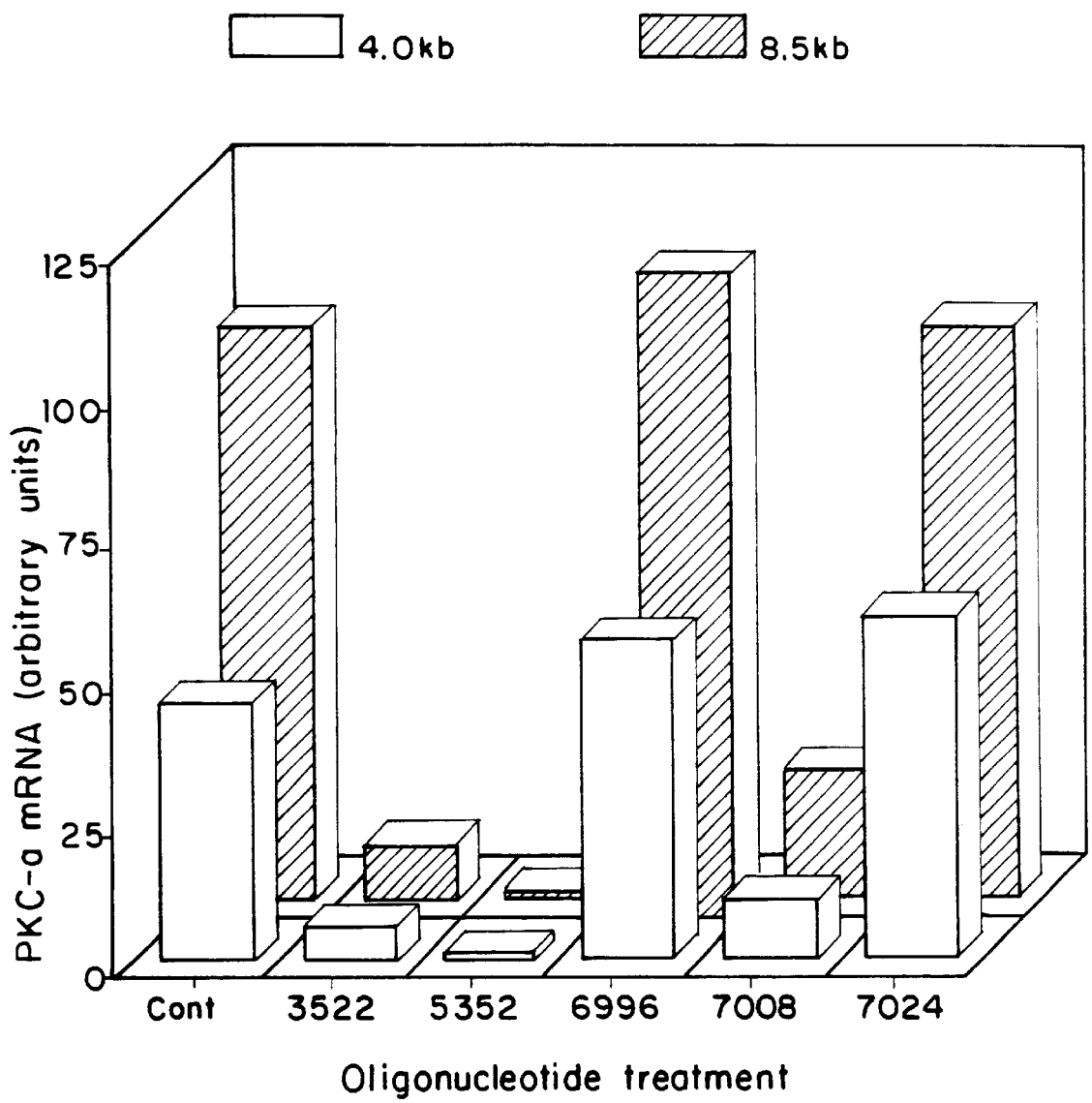
FIG. 6 is a bar graph showing the effects of several 2'-O-methyl chimeric oligonucleotides of SEQ ID NO:3 on PKC-α mRNA levels. Hatched bars represent the 8.5 kb transcript, plain bars represent the 4.0 kb transcript.

The effect of these oligonucleotides on PKC-α mRNA levels is shown in FIG. 6. Oligonucleotides 7008, 3522 and 5352 show reduction of PKC-α mRNA, with 5352 being most active.

A series of 2'-O-propyl chimeric oligonucleotides was synthesized having SEQ ID NO:3. These oligonucleotides are shown in Table 6.

TABLE 6

CHIMERIC 2'-O-PROPYL/DEOXY P=S OLIGONUCLEOTIDES

| OLIGO # | SEQUENCE | SEQ ID NO: |
|---------|----------|------------|
| 7199 | AsAsAsAsCsGsTsCsAsGsCsCsAsTsGsGsTsCsCsC | 3 |
| 7273 | AoAoAoAoCoGsTsCsAsGsCsCsAsTsGoGoToCoCoC | 3 |
| 7294 | AsAoAoAoCoGsTsCsAsGsCsCsAsTsGoGoToCoCsC | 3 |
| 7295 | AsAoAoAoCoGsToCsAoGsCoCsAsTsGoGoToCoCsC | 3 | bold = 2'-O-propyl; s = P=S linkage, o = P=O linkage

Figure 7:
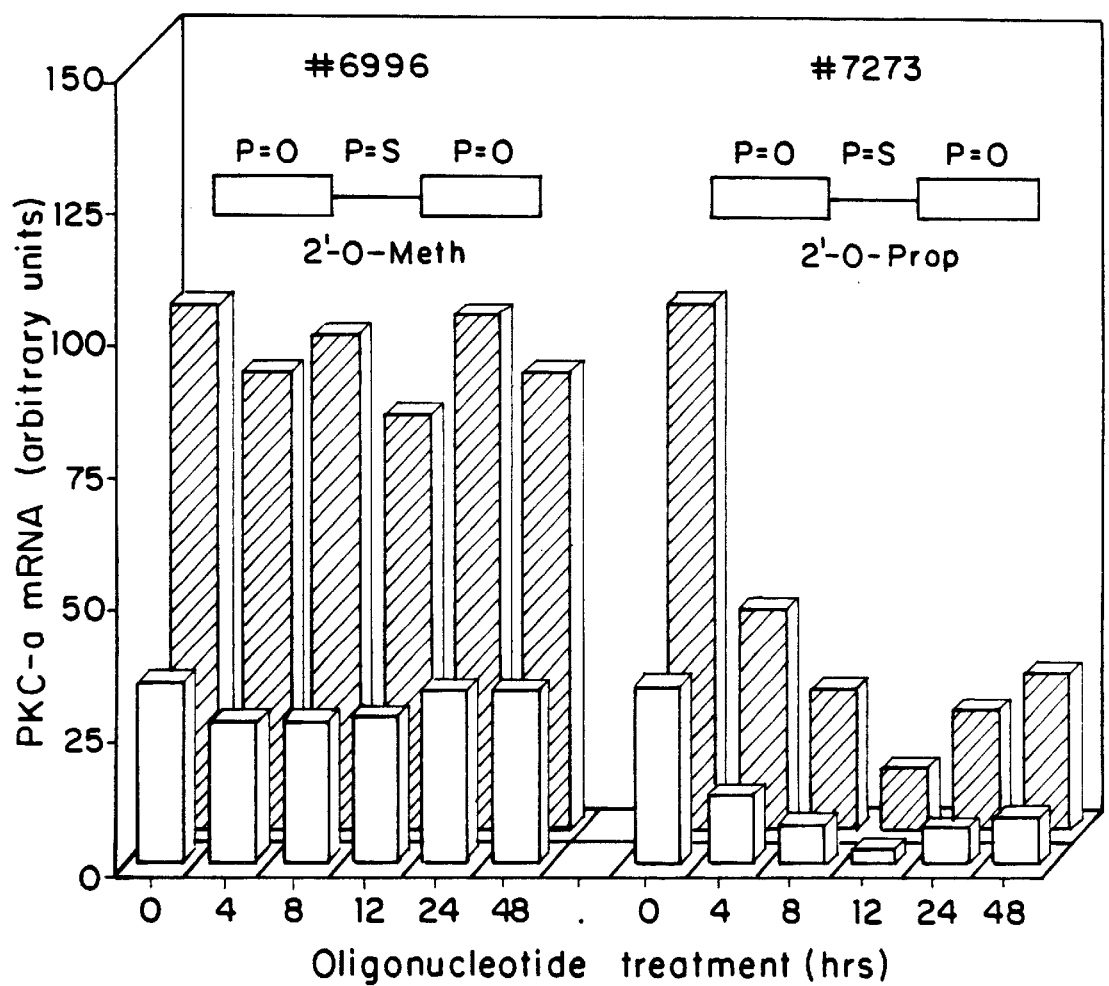
FIG. 7 is a bar graph and diagram showing the effects of several 2'-O-methyl and 2'-O-propyl chimeric oligonucleotides (6996, 7273) of SEQ ID NO:3 on PKC-α mRNA levels. Hatched bars represent the 8.5 kb transcript, plain bars represent the 4.0 kb transcript.
Figure 8:
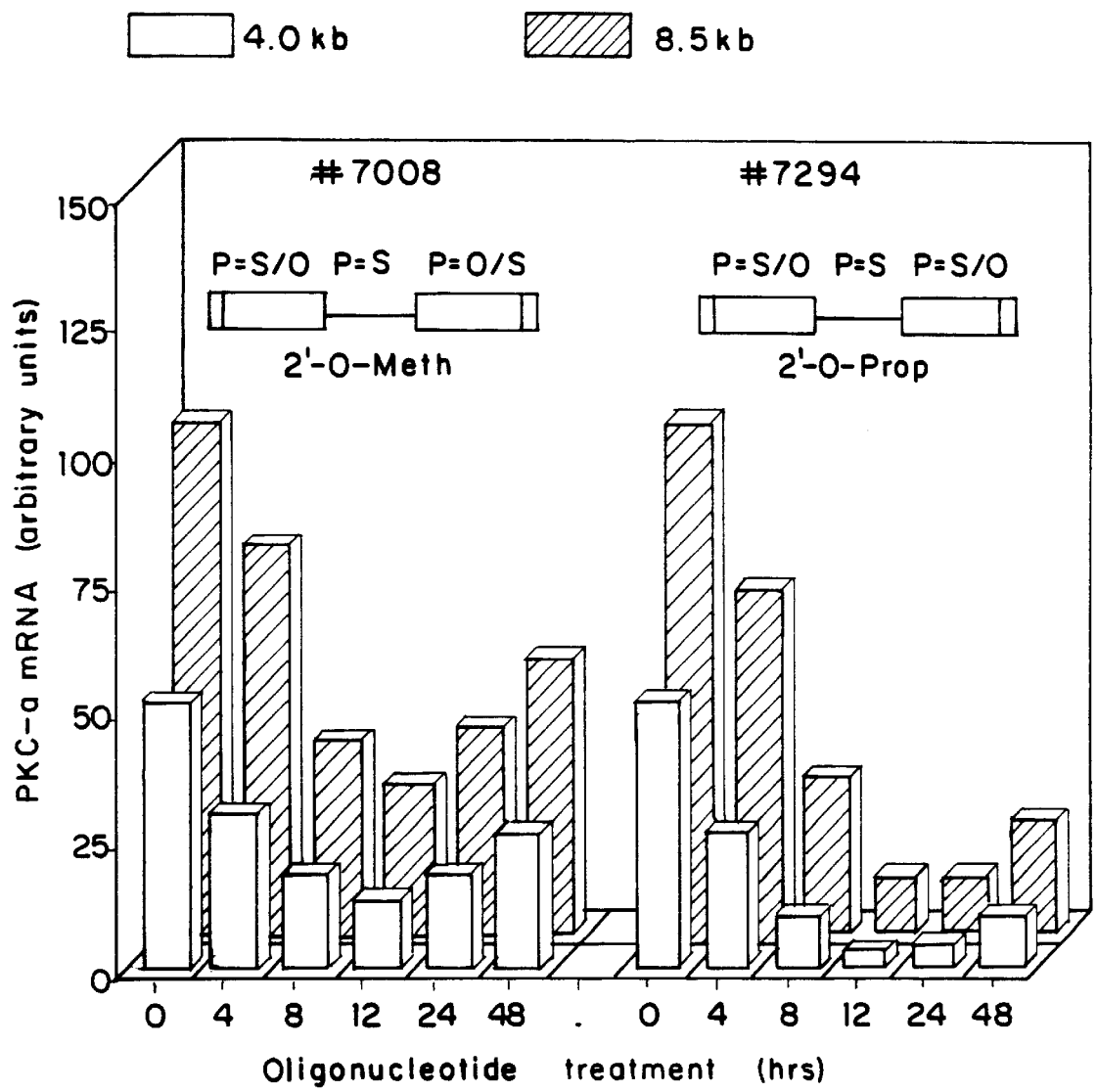
FIG. 8 is a bar graph and diagram showing the effects of additional 2'-O-methyl and 2'-O-propyl chimeric oligonucleotides (7008, 7294) of SEQ ID NO:3 on PKC-α mRNA levels. Hatched bars represent the 8.5 kb transcript, plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α mRNA levels (FIGS. 7 and Example 10
Additional Oligonucleotides which Decrease PKC-α mRNA Additional phosphorothioate oligonucleotides targeted to the human PKC-α 3' untranslated region were designed and synthesized. These sequences are shown in Table 7.

subcutaneously in the inner thigh of nude mice. ISIS 3521, a phosphorothioate oligonucleotide with SEQ ID NO:2 was administered twice weekly for four weeks, beginning one week following tumor cell inoculation. Oligonucleotides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

As shown in FIG. 10, tumor growth was almost completely inhibited in two of the three mice, and reduced compared to control in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

TABLE 7

CHIMERIC 2'-O-PROPYL/DEOXY P=S OLIGONUCLEOTIDES
TARGETED TO PKC-α 3'-UTR

| OLIGO # | SEQUENCE | SEQ ID NO: |
|---------|----------|------------|
| 6632 | TsTsCs TsCsGs CsTsGs GsTsGs AsGsTs TsTsC | 52 |
| 6653 | TsTsCs TsCsGs CsTsGs GsTsGs AsGsTs TsTsC | 52 |
| 6665 | ToToCo TsCsGs CsTsGs GsTsGs AsGsTo ToToC | 52 |
| 7082 | TsCsTs CsGsCs TsGsGs TsGsAs GsTsTs TsC | 53 |
| 7083 | TsCsTs CsGsCs TsGsGs TsGsAs GsTsTs TsC | 53 |
| 7084 | ToCoTo CsGsCs TsGsGs TsGsAs GsToTo ToC | 53 | bold = 2'-O-propyl; s = P=S linkage, o = P=O linkage

Figure 9A:
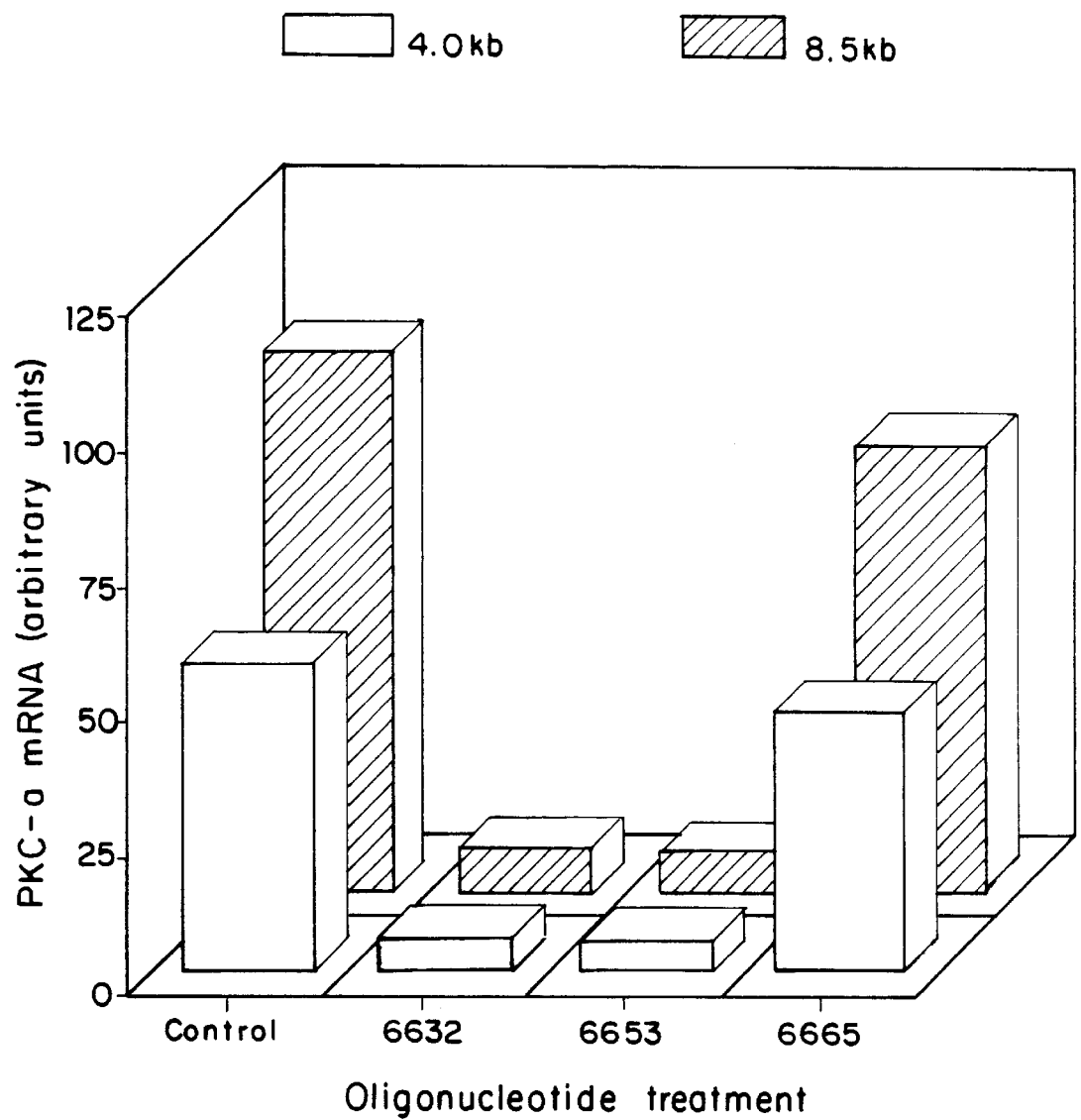
FIG. 9A shows oligonucleotides 6632, 6653 and 6665.
Figure 9B:
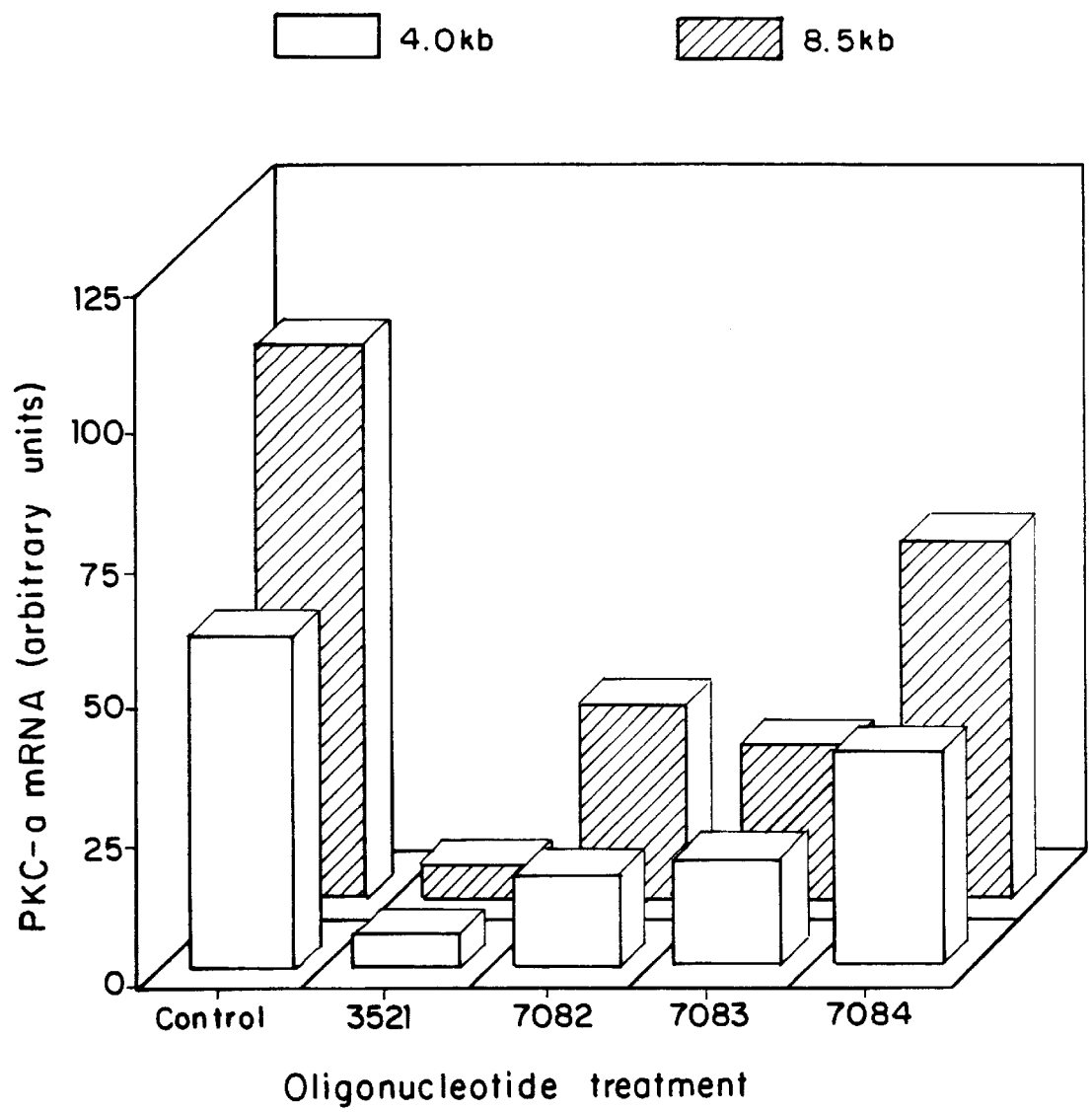
FIG. 9B shows oligonucleotides 3521 (for comparison), 7082, 7083 and 7084. Hatched bars represent the 8.5 kb transcript, plain bars represent the 4.0 kb transcript.

As shown in FIG. 9, oligonucleotides 6632, 6653, 7082 and are most active in reducing PKC-α mRNA levels.

Example 11
Effect of Oligonucleotides on Tumor Cells in Nude Mice (A) Effect of ISIS 3521 on the growth of human A549 lung tumor cells in nude mice: The human lung carcinoma cell line 549 was obtained from the American Type Culture Collection (Rockville, Md.). Cells were grown in Dulbecco's Modified Eagle's Medium (Irvine Scientific, Irvine, Calif.) containing 1 gm glucose/liter and 10% fetal calf serum (Irvine Scientific). Cells were trypsinized and washed and resuspended in the same medium for introduction into mice. 200 µl of A549 cells (5×10⁶ cells) were implanted (B) Effect of antisense oligonucleotides on growth of human MDA-MB231 tumors in nude mice: MDA-MB231 human breast carcinoma cells were obtained from the American Type Culture Collection (Rockville, Md.). Serially transplanted MDA-MB231 tumors were established subcutaneously in nude mice. Beginning two weeks later, oligonucleotides 3521 and 3527, a phosphorothioate oligonucleotide having Sequence ID NO. 5, in saline, were administered intravenously daily for 14 days at dosages of 60 mg/kg and 6 mg/kg. Control oligonucleotide ISIS 1082 was also administered at these doses, and a saline control was also given. Tumor growth rates were monitored for the two-week period of oligonucleotide administration. As shown in FIG. 11, both PKC-α oligonucleotides (3521 and 3527) significantly inhibit tumor growth at dosages of 60 mg/kg and 6 mg/kg. The control oligonucleotide (ISIS 1082) also showed some reduction in tumor growth, but this effect was less than with antisense oligonucleotides even at high doses, and considerably less at the lower dose. A lower-dose study was conducted using the same oligonucleotides at 6 mg/kg and 0.6 mg/kg. At 0.6 mg/kg ISIS 3521 significantly reduced tumor growth. At this concentration, ISIS 3527 also reduced tumor growth, but this result was not statistically significant.

(C) Effect of oligonucleotides on the growth of murine Lewis lung carcinoma in mice: Serially transplanted murine Lewis lung carcinomas were established in mice. Oligonucleotides 3521 and 3527 were administered intravenously every day for 14 days at doses of 6 mg/kg and 0.6 mg/kg. Tumor growth rates were monitored for the two-week period of oligonucleotide administration. As expected, these oligonucleotides, which are targeted to human PKC sequences, had insignificant effects on the mouse-derived tumors.

(D) Effect of ISIS 3521 on the growth of human T24 bladder tumors in nude mice: Subcutaneous human T24 bladder carcinoma xenografts in nude mice were established by injection of $5 \times 10^6$ T24 cells under the skin. Mice were treated with ISIS 3521 or ISIS 4559, a phosphorothioate scrambled version of the ISIS 3521 sequence, or ISIS 1082, an unrelated control phosphorothioate oligonucleotide targeted to Herpes simplex virus (oligonucleotide doses 0.006 mg/kg, 0.06 mg/kg, 0.6 mg/kg or 6.0 mg/kg) or saline administered intraperitoneally three times weekly. By day 21, ISIS 1082 or ISIS 4559 had no effect on tumor growth at any dose. By day 21, ISIS 3521 showed a dose-dependent inhibition of tumor growth at all dose levels, with a maximal inhibition of 90% at the 6 mg/kg dose.

(E) Effect of ISIS 3521 on the growth of human Colo-205 colon tumors in nude mice: Subcutaneous human Colo-205 colon carcinoma xenografts in nude mice were established by injection of $5 \times 10^6$ Colo-205 cells under the skin. Mice were treated with ISIS 3521 and an unrelated control phosphorothioate oligonucleotide (ISIS 1082) administered intravenously once per day at a dosage of 6.0 mg/kg. In this study, ISIS 3521 inhibited tumor growth after 25 days by 84- compared to saline controls. The control oligonucleotide, ISIS 1082, inhibited tumor growth by 20%.

(F) Effect of ISIS 8469, a 2'-fluoro gapped version of ISIS 3521, on the growth of A549 human lung tumors in nude mice: Subcutaneous human A549 lung adenocarcinoma xenografts were established by injection of $5 \times 10^6$ A549 cells under the skin of Balb/c nude mice. Mice were treated with ISIS 8469, a chimeric version of ISIS 3521 having an 8-nucleotide deoxy gap flanked by six 2'-fluoro nucleotides on each side, as in Example 9. Oligonucleotide doses were from 0.006 mg/kg to 6.0 mg/kg. ISIS 8469 decreased tumor size at all doses in a dose-dependent manner, as shown in FIG. 12. This compound is therefore preferred.

(G) U-87 human glioblastoma cell culture and subcutaneous xenografts into nude mice: The U-87 human glioblastoma cell line was obtained from the ATCC (Rockville, Md.) and maintained in Iscove's DMEM medium supplemented with heat-inactivated 10% fetal calf serum. Nude mice were injected subcutaneously with $2 \times 10^7$ cells. Mice were injected intraperitoneally with ISIS 3521 at dosages of either 2 mg/kg or 20 mg/kg for 21 consecutive days beginning 7 days after xenografts were implanted. Tumor volumes were measured on days 14, 21, 24, 31 and 35. On day 35 (7 days after end of treatment), ISIS 3521 at 2 mg/kg had reduced tumor volume by 84% compared to saline or sense oligonucleotide control. The 20 mg/kg dose reduced tumor size by 91% on day 35.

(H) Effect of ISIS 3521 on PKC-α protein levels in U-87 glioblastoma xenografts in nude mice: PKC-α protein levels in subcutaneous U-87 tumor xenografts were measured by western blot analysis on day 24 (day 17 of treatment with ISIS 3521) and day 35 (7 days after end of treatment with ISIS 3521). An affinity-purified PKC-α-specific polyclonal antibody (Life Technologies, Inc., Gaithersburg, Md.) was used as the primary antibody. By day 24, ISIS 3521 was found to virtually totally abolish PKC-α in the tumors. By seven days after cessation of oligonucleotide treatment (day 35), PKC-α had returned to control levels.

(I) "Crossover experiment" to evaluate effect of switching treatment on tumor size: The two groups of mice with subcutaneous U-87 xenografts previously treated with ISIS 3521 (2 mg/kg or 20 mg/kg) were switched to different treatments on day 35 (7 days after the initial 21 day treatment had ended). The group which had previously received 20 mg/kg ISIS 3521 now received saline ("high dose-to-control"). The group which had received 2 mg/kg ISIS 3521 now received 20 mg/kg ISIS 3521 ("low dose-to-high dose"). This crossover treatment was continued for 21 days as for the original treatment. As shown in FIG. 13, the growth of the tumors in the "low dose-to-high dose" group (open triangles) leveled off after treatment was switched (arrow). The growth of the tumors in the "high dose-to-control" group (closed triangles) rapidly accelerated after switching to saline treatment (arrow). (Other symbols in FIG. 13: S=sense oligonucleotide (control); AS=antisense oligonucleotide (ISIS 3521) targeted to PKC-α.)

(J) Effect of ISIS 3521 on intracerebral U-87 glioblastoma xenografts into nude mice: U-87 cells how were implanted in the brains of nude mice. Mice were treated via continuous intraperitoneal administration of antisense oligonucleotide ISIS 3521 (20 mg/kg), control sense oligonucleotide (20 mg/kg) or saline beginning on day 7 after xenograft implantation. All mice survived until day 25, at which point the saline-treated mice began to die. All saline-treated mice and sense oligonucleotide-treated mice were dead by day 41. In contrast, all ISIS 3521-treated mice were alive until approximately day 37, and half of the mice were still alive at day 61. At the termination of the experiment at day 80, 40% of the ISIS 3521-treated mice were still alive.

Example 12

Effects of Antisense Oligonucleotide ISIS 4189 on Endogenous PKC-α Expression in Hairless Mice In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an $IC_{50}$ of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 13

Sequences of Oligonucleotides Targeted to the $\beta_I$, $\beta_{II}$, γ and η Isozymes of PKC Results with oligonucleotides targeting human PKC-α demonstrated that the most effective target sequences were those surrounding the translation initiation codon and the 3' untranslated region. It is believed that these sequences will also be effective targets for oligo-nucleotides directed against other isozymes of PKC. The other isozymes of human PKC for which sequence data are available are PKC-β (types I and II), PKC-γ (partial sequence), PKC-δ, PKC-ε, PKC-ζ and PKC-η. Antisense oligonucleotides which are likely to be effective inhibitors of PKC are identified below. Racemic versions of these oligonucleotides are synthesized as in Example 1, and can be screened and evaluated as in Examples 5–12, using appropriate antibodies (i.e., anti-PKC-γ, anti-PKC-η, etc.) and probes. Alternatively, a reporter gene assay system can be established, transiently co-expressing the desired isozyme of PKC with luciferase under the influence of the TPA-responsive enhancer or other suitable promoter. PKC expression is then assayed by measuring luciferase activity using standard procedures. Luciferase is extracted from cells by lysis with the detergent Triton X-100, as described by Greenberg, M. E. (In: *Current Protocols in Molecular Biology*, F. M. Ausubel, R. Brent, R. E. Kingston, D. D. Moore, J. A. Smith, J. G. Seidman and K. Strahl, eds., John Wiley and Sons, N.Y., 1987). A Dynatech ML1000 luminometer is used to measure peak luminescence upon addition of luciferin (Sigma Chem. Co., St. Louis, Mo.) to 625 μM. Substantially chirally pure versions of active oligonucleotides are prepared according to the methods of Examples 2–4 and evaluated according to the methods of Examples 5–12.

PKC-β, types I and II

Sequence data are from Kubo et al. (*FEBS Lett.* 223:138, 1987; Genbank accession numbers X06318, M27545, X07109). Sequences are numbered from the first 5' base sequenced on the cDNA. PKC-β types I and II are the result of alternative mRNA splicing of a single gene product. This results in proteins with identical amino termini (5' end of the mRNA); however, there is sequence divergence in the carboxy termini (3' end of the mRNA). The following oligonucleotides, targeted to the translation initiation codon, are expected to modulate expression of both PKC-β types I and II:

TABLE 8

OLIGONUCLEOTIDES TARGETED TO PKC-β TYPES I AND II

| SEQ ID | Sequence | Target |
|---|---|---|
| 21 | CAT CTT GCG CGC GGG GAG CC<br>139                          120 | Translation init. |
| 22 | TGC GCG CGG GGA GCC GGA GC<br>134                          115 | " |
| 23 | CGA GAG GTG CCG GCC CCG GG<br>113                           94 | " |
| 24 | CTC TCC TCG CCC TCG CTC GG<br>183                          164 | " |

The following antisense oligonucleotides are targeted to the 3'-untranslated region of PKC-β type I:

TABLE 9

OLIGONUCLEOTIDES TARGETED TO PKC-β TYPE I

| SEQ.ID | Sequence | Target |
|---|---|---|
| 25 | TGG AGT TTG CAT TCA CCT AC<br>2168                         2149 | 3' Untranslated |
| 26 | AAA GGC CTC TAA GAC AAG CT<br>2285                         2266 | " |
| 27 | GCC AGC ATG TGC ACC GTG AA<br>2250                         2231 | " |
| 28 | ACA CCC CAG GCT CAA CGA TG<br>2186                         2167 | " |
| 29 | CCG AAG CTT ACT CAC AAT TT<br>2569                         2550 | " |

The following antisense oligonucleotides are targeted to the 3'-untranslated region of PKC-β Type II:

TABLE 10

OLIGONUCLEOTIDES TARGETED TO PKC-β TYPE II

| SEQ.ID | Sequence | Target |
|---|---|---|
| 30 | ACT TAG CTC TTG ACT TCG GG<br>2160                         2141 | 3' Untranslated |
| 31 | ATG CTG CGG AAA ATA AAT TG<br>2420                         2401 | " |
| 32 | ATT TTA TTT TGA GCA TGT TC<br>2663                         2644 | " |
| 33 | TTT GGG GAT GAG GGT GAG CA<br>2843                         2824 | " |
| 34 | CCC ATT CCC ACA GGC CTG AG<br>3137                         3118 | " |

PKC-γ:

Sequence data are from Coussens et al. (*Science* 233:859, 1986; Genbank accession number M13977). Sequences are numbered from the first 5' base sequenced in the cDNA. The full sequence is not available: the extreme 3' end of the open reading frame and the 3' untranslated region are missing. Consequently these regions are not presently available as antisense targets.

TABLE 11

OLIGONUCLEOTIDES TARGETED TO PKC-γ

| SEQ.ID | Sequence | Target |
|---|---|---|
| 35 | CGG AGC GCG CCA GGC AGG GA<br>51                             32 | 5' Untranslated |
| 36 | CCT TTT CCC AGA CCA GCC AT<br>215                           196 | Translation init. |
| 37 | GGC CCC AGA AAC GTA GCA GG<br>195                           176 | 5' of start codon |
| 38 | GGA TCC TGC CTT TCT TGG GG<br>170                           151 | 5' Untranslated |

TABLE 11-continued

OLIGONUCLEOTIDES TARGETED TO PKC-γ

| SEQ.ID | Sequence | Target |
|---|---|---|
| 39 | CAG CCA TGG CCC CAG AAA CG 202 | Translation init. 183 |

PKC-η:

Sequence data for PKC-η are from Bacher and colleagues (Bacher et al., *Mol. Cell. Biol.* 11:126, 1991; Genbank accession number M55284). They assign their isozyme the name PKC-L; however the sequence is almost identical to that of mouse PKC-η, so the latter nomenclature is used here for consistency. Sequences are numbered from the first 5' base sequenced in the cDNA.

TABLE 12

OLIGONUCLEOTIDES TARGETED TO PKC-η

| SEQ.ID | Sequence | Target |
|---|---|---|
| 40 | CGA CAT GCC GGC GCC GCT GC 172 | Translation init. 153 |
| 41 | CAG ACG ACA TGC CGG CGC CG 176 | " 157 |
| 42 | GCC TGC TTC GCA GCG GGA GA 138 | " 119 |
| 43 | ACA GGT GCA GGA GTC GAG GC 86 | " 67 |
| 44 | GTC CCG TCT CAG GCC AGC CC 111 | " 92 |
| 45 | CCT CAC CGA TGC GGA CCC TC 221 | " 202 |
| 46 | ATT GAA CTT CAT GGT GCC AG 193 | " 174 |
| 47 | TCT CAC TCC CCA TAA GGC TA 2046 | 3' Untranslated 2027 |
| 48 | TTC CTT TGG GTT CTC GTG CC 2067 | " 2048 |
| 49 | TTC CAT CCT TCG ACA GAG TT 2353 | " 2336 |
| 50 | AGG CTG ATG CTG GGA AGG TC 2300 | " 2281 |
| 51 | GTT CTA AGG CTG ATG CTG GG 2306 | " 2287 |

Example 14

Screening of Antisense Oligonucleotides Targeted to Human PKC-η

A series of 20-mer phosphorothioate oligonucleotides complementary to human PKC-η were synthesized. These oligonucleotides were screened at a concentration of 500 nM for ability to decrease PKC-η mRNA levels in human A549 cells, using a Northern blot assay. The oligonucleotide sequences are shown in Table 13 and the results are shown in FIG. 12.

TABLE 13

OLIGONUCLEOTIDES TARGETED TO HUMAN PKC-η mRNA

| ISIS No. | Sequence | Target | SEQ ID NO: |
|---|---|---|---|
| 6431 | CGA CAT GCC GGC GCC GCT GC | AUG | 40 |
| 6442 | CAG ACG ACA TGC CGG CGC CG | AUG | 41 |
| 6443 | GCC TGC TTC GCA GCG GGA GA | 5' UTR | 42 |
| 6432 | ACA GGT GCA GGA GTC GAG GC | 5' UTR | 43 |
| 6433 | GTC CCG TCT CAG GCC AGC CC | 5' UTR | 44 |
| 6435 | CCT CAC CGA TGC GGA CCC TC | Coding | 45 |
| 6441 | ATT GAA CTT CAT GGT GCC AG | Coding | 46 |
| 6581 | TCT CAC TCC CCA TAA GGC TA | 3' UTR | 47 |
| 6580 | TTC CTT TGG GTT CTC GTG CC | 3' UTR | 48 |
| 6436 | AAC TCG AGG TGG CCG CCG TC | Coding | 54 |
| 6434 | CGC CTT CGC ATA GCC CTT TG | Coding | 55 |
| 6444 | GGA AGG GGT GAT TGC GGG CC | Coding | 56 |
| 6445 | AAC ACG CCC ATT GCC CAC CA | Coding | 57 |
| 6446 | GTC TCA AGA TGG CGT GCT CG | Coding | 58 |
| 6553 | GCG ATG GTT CAG CTG GGC CC | Coding | 59 |
| 6605 | GCC CTC TCT CTC ACT CCC CA | 3' UTR | 60 |
| 6579 | CTG GGA AGG TCC GAT AGA GG | 3' UTR | 61 |
| 6603 | AAG GCT GAT GCT GGG AAG GT | 3' UTR | 62 |

Oligonucleotides 6432, 6443, 6431, 6442, 6435, 6434, 6553, 6581 and 6603 reduced PKC-η mRNA levels by greater than 50%. The most potent oligonucleotides were ISIS6581 (targeting 3' untranslated region) and ISIS 6445 (targeting coding region) which gave nearly complete loss of PKC mRNA in this assay.

Example 15

Screening of Antisense Oligonucleotides Targeted to PKC-δ

A series of 20-mer phosphorothioate oligonucleotides complementary to human PKC-δ were synthesized. These oligonucleotides were screened by Northern blot assay at a concentration of 500 nM for their ability to decrease PKC-δ mRNA levels in human A549 cells. The oligonucleotide sequences and the results, expressed as percent inhibition of PKC-δ mRNA expression, are shown in Table 14.

TABLE 14

ANTISENSE OLIGONUCLEOTIDES TARGETED TO PKC-δ

| Isis # | Site | Sequence | % Inhib | SEQ ID: |
|---|---|---|---|---|
| 10299 | AUG | GCA GGA ACG GCG CCA TGG TG | 0% | 63 |
| 10300 | Coding | CTG GTT CGC CTC GTC CTC GG | 25% | 64 |
| 10301 | Coding | ATC TGG ATG ACG CGC CCC TC | 26% | 65 |
| 10302 | Coding | TTC TTG CAG CGC TCG GCC AG | 8% | 66 |
| 10303 | Coding | TGC AAT CCA CGT CCT CCA GG | 50% | 67 |
| 10304 | Coding | GGC TCC GCG GCG GTT CAT CG | 12% | 68 |
| 10305 | Coding | AAG CGG TGC GGC ATG TCG AT | 43% | 69 |
| 10306 | Coding | GCA GGC TGC CGC AGT GGT CA | 12% | 70 |
| 10307 | Coding | CCT CCC CAG CAA CTC CGG TC | 36% | 71 |
| 10308 | Coding | AGC GGC CTT TGT CCT GGA TG | 11% | 72 |
| 10309 | Coding | GGC CAT CCC GGT CCA ACA GC | 43% | 73 |
| 10310 | Coding | GGT GCT GGC CCG GCT CTC CC | 66% | 74 |
| 10311 | Coding | GGA CCC CGA AAG ACC ACC AG | 77% | 75 |
| 10312 | Coding | GTG GCT CCA ACC TCC GCT TT | 18% | 76 |
| 10313 | Coding | AGG AGG TGC TCG AAT TTG GG | 0% | 77 |

Oligonucleotides ISIS 10303, ISIS 10310 and ISIS 10311 gave at least 50% inhibition of PKC-δ mRNA expression in this assay and are preferred.

Example 16
Screening of Antisense Oligonucleotides Targeted to PKC-ε

A series of 20-mer phosphorothioate oligonucleotides complementary to human PKC-ε were synthesized. These oligonucleotides were screened by Northern blot assay at a concentration of 500 nM for their ability to decrease PKC-ε mRNA levels in human A549 cells. The oligonucleotide sequences and the results, expressed as percent inhibition of PKC-ε mRNA expression, are shown in Table 15.

TABLE 15

ANTISENSE OLIGONUCLEOTIDES TARGETED TO PKC-ε

| Isis # | Site | Sequence | % Inhib | SEQ ID: |
|---|---|---|---|---|
| 7933 | AUG | ACT ACC ATG GTC GGG GCG GG | 0% | 78 |
| 7934 | Coding | GTC CCA CCG CAT GGC GCA GC | 0% | 79 |
| 7935 | Coding | GTT TGG CCG ATG CGC GAG TC | 0% | 80 |
| 7936 | Coding | TGC AGT TGG CCA CGA AGT CG | 0% | 81 |
| 8032 | Coding | GTG GGG CAT GTT GAC GCT GA | 0% | 82 |
| 8031 | Coding | CCA GAG CAG GGA CCC ACA GT | 0% | 83 |
| 7939 | Coding | TCT CCT CGG TTG TCA AAT GA | 0% | 84 |
| 7940 | Coding | CGG TGC TCC TCT CCT CGG TT | 0% | 85 |
| 7941 | Coding | AGC CAA AAT CCT CTT CTC TG | 0% | 86 |
| 7942 | Coding | CAT GAG GGC CGA TGT GAC CT | 67% | 87 |
| 7943 | Coding | ATC CCT TCC TTG CAC ATC CC | 3% | 88 |
| 7944 | Coding | CCC CAG GGC CCA CCA GTC CA | 38% | 89 |
| 7945 | Coding | AGC ACC CCC AGG GCC CAC GA | 42% | 90 |

TABLE 15-continued

ANTISENSE OLIGONUCLEOTIDES TARGETED TO PKC-ε

| Isis # | Site | Sequence | % Inhib | SEQ ID: |
|---|---|---|---|---|
| 7946 | Coding | CGT ACA TCA GCA CCC CCA GG | 42% | 91 |
| 7947 | Coding | CCA GCC ATC ATC TCG TAC AT | 9% | 92 |
| 7948 | Coding | TGC CAC ACA GCC CAG GCG CA | 55% | 93 |
| 7949 | Stop | TCA GGG CAT CAG GTC TTC AC | 0% | 94 |
| 7950 | Stop | CTC TCA GGG CAT CAG GTC TT | 0% | 95 |

Oligonucleotides ISIS 7942 and ISIS 7948 gave at least 50% inhibition of PKC-ε mRNA expression in this assay and are preferred.

Additional oligonucleotides targeted to PKC-ε were synthesized. These are shown in Table 16.

TABLE 16

ANTISENSE OLIGONUCLEOTIDES TARGETED TO PKC-ε

| Isis # | Site | Sequence | SEQ ID: |
|---|---|---|---|
| A | Coding | AAG GAA AGT CTG CGG CCG GG | 96 |
| B | Coding | TGG CGG CTC CCG TTC TGC AG | 97 |
| C | Coding | GCT TCC TCG GCC GCA TGC GT | 98 |
| D | Coding | TTG ACG CTG AAC CGC TGG GA | 99 |
| E | Coding | GCC CGG TGC TCC TCT CCT CG | 100 |
| F | Coding | GGG CCG ATG TGA CCT CTG CA | 101 |
| G | Coding | TGG AGG AAC ATG AGG GCC GA | 102 |

TABLE 16-continued

ANTISENSE OLIGONUCLEOTIDES TARGETED TO PKC-ε

| Isis # | Site | Sequence | SEQ ID: |
|---|---|---|---|
| H | Coding | CCC CCA GGG CCC ACC AGT CC | 103 |
| I | Coding | TGC GAT GCC ACA CAG CCC AG | 104 |
| J | Stop | TGG GCT CTC AGG GCA TCA GG | 105 |

Example 17

Screening of Antisense Oligonucleotides Targeted to PKC-ζ

A series of 20-mer phosphorothioate oligonucleotides complementary to human PKC-ζ were synthesized. These oligonucleotides were screened by Northern blot assay at a concentration of 500 nM for their ability to decrease PKC-ζ mRNA levels in human A549 cells. The oligonucleotide sequences and the results, expressed as percent inhibition of PKC-ζ mRNA expression, are shown in Table 17.

TABLE 17

ANTISENSE OLIGONUCLEOTIDES TARGETED TO PKC-ζ

| Isis # | Site | Sequence | % Inhib | SEQ ID: |
|---|---|---|---|---|
| 9007 | AUG | CGC CGC TCC CTT CCA TCT TG | 67% | 106 |
| 9008 | Coding | CCC CGT AAT GCG CCT TGA GG | 64% | 107 |
| 9009 | Coding | CTG TCC ACC CAC TTG AGG GT | 14% | 108 |
| 9012 | Coding | TTG GAA GAG GTG GCC GTT GG | 78% | 109 |
| 9013 | Coding | CCT GTT AAA GCG CTT GGC TT | 67% | 110 |
| 9014 | Coding | TGC AGG TCA GCG GGA CGA GG | 40% | 111 |
| 9016 | Coding | AGC CCC TGA GAG ATT TTG AT | 0% | 112 |
| 9017 | Coding | TTC TTC AAC CGC ACC AGG AG | 67% | 113 |
| 9019 | Coding | TCC TTG CAC ATG CCG TAG TC | 24% | 114 |
| 9021 | Coding | GGA GCG CCC GGC CAT CAT CT | 78% | 115 |
| 9022 | Coding | GGG CTC GCT GGT GAA CTG TG | 85% | 116 |
| 9023 | 3' UTR | GAC GCA CGC GGC CTC ACA CC | 88% | 117 |
| 9025 | 3' UTR | TCG AGC CGT GCC CCA GCC TG | 88% | 118 |

TABLE 17-continued

ANTISENSE OLIGONUCLEOTIDES TARGETED TO PKC-ζ

| Isis # | Site | Sequence | % Inhib | SEQ ID: |
|---|---|---|---|---|
| 9026 | 3' UTR | CGG GCC AGG TGT GAG GGA CT | 40% | 119 |
| 9027 | 3' UTR | CCG CGA CGC AGG CAC AGC AG | 40% | 120 |
| 9029 | 3' UTR | GGT CAG TGC ATC GAG TTC TG | 77% | 121 |

Oligonucleotides ISIS 9007, 9008, 9012, 9013, 9017, 9021, 9022, 9023, 9025 and 9029 gave greater than 50% inhibition of PKC-ζ mRNA expression in this assay and are preferred. Of these, ISIS 9022, ISIS 9023 and ISIS 9025 gave at least 85% inhibition and are more preferred.

Example 18
Administration of Antisense Oligonucleotides to Human and Animal Patients (A) Treatment of a disease state in a patient: The oligonucleotides of the invention may be used for treatment of various disease states. Treatment of a patient diagnosed with a particular disease state comprises administration of an effective dose of the oligonucleotide, in a pharmaceutically accepted formulation, to the patient via an appropriate route. The effective oligonucleotide dose depends on the disease state being treated, the severity of the disease state and the age of the patient being treated. The effective dose of an oligonucleotide may be determined based on its $IC_{50}$ and is a routine procedure for one of skill in the art. Alternatively, the effective dose of the oligomer may be determined by using the pharmacokinetics software program TopFit. For example, dosage of oligonucleotides may vary from 0.01 µg (for children) to 100 g (for adults) per kg of body weight depending on progression of the disease state. Similarly, the frequency of dosing depends on the progression of the disease state and may vary from once or more daily to once every 20 years.

The route of oligonucleotide administration depends on the disease state being treated. For example, administration of an oligonucleotide to a patient being treated for an inflammatory disorder may be accomplished either via oral or rectal routes. For treatment of a patient afflicted with AIDS, the most effective method of oligonucleotide administration may be an oral route or by subcutaneous injection. Cancers such as breast cancer may be treated via subcutaneous injection, while colon cancer may be treated via oral or rectal administration of the oligonucleotide. Diseases or disorders of the central nervous system may best be treated by intrathecal or intraventricular administration for delivery of the oligonucleotide to the spinal column or the brain of the patient.

Following oligonucleotide administration, the patient may be monitored for alleviation of symptoms associated with the disease state. Subsequently, the dosage may be adjusted (increased or decreased) depending upon the severity and amenability of the disease state to treatment.

It may be preferable to administer oligonucleotides of the invention in combination with other traditional therapeutics. The oligonucleotides may be administered in combination with drugs including, but not limited to, AZT for the treatment of patients afflicted with AIDS, sulfasalazine for the treatment of an inflammatory disorder such as ulcerative colitis, and 5-fluorouracil for the treatment of colon cancer.

Also, it may be desirable to administer maintenance therapy to a patient who has been successfully treated for a disease state. The dosage and frequency of oligonucleotide administration as part of a maintenance regimen may vary from 0.01 µg to 100 g per kg of body weight, ranging from once or more daily to once every several years.

(B) Intraventricular administration of oligonucleotides: Intraventricular drug administration, for the direct delivery of drug to the brain of a patient, may be desired for the treatment of patients with diseases afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., Cancer Research, 44:1698, 1984). The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 µg to 100 g per kg of body weight, the pump reservoir may be refilled at 3–10 week intervals. Refilling of the pump is accomplished by percutaneous puncture of the self-sealing septum of the pump.

(C) Intrathecal Administration of Oligonucleotides: Intrathecal drug administration for the introduction of drug into the spinal column of a patient may be desired for the treatment of patients with diseases of the central nervous system. To effect this route of oligonucleotide administration, a silicon catheter is surgically implanted into the L3-4 lumbar spinal interspace of a human patient, and is connected to a subcutaneous infusion pump which has been surgically implanted in the upper abdominal region (Luer and Hatton, The Annals of Pharmacotherapy, 27:912, 1993; Ettinger et al., Cancer, 41:1270, 1978). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 µg to 100 g per kg of body weight, the pump reservoir may be refilled at 3–10 week intervals. Refilling of the pump is accomplished by a single percutaneous puncture to the self-sealing septum of the pump.

Example 19
Treatment of Patients with Antisense Oligonucleotides (A) A patient suffering from hepatitis caused by HCV is treated with Oligo #259 (SEQ ID NO:122), Oligo #260

(SEQ ID NO:123), Oligo #270 (SEQ ID NO:124), Oligo #330 (SEQ ID NO:125) or Oligo #340 (SEQ ID NO:126), each of which is synthesized according to the procedures of Examples 1–4. 1–1000 μg/kg body weight of oligonucleotide is incorporated into a pharmaceutically acceptable carrier and administered intravenously or intramuscularly. Treatment may be repeated as necessary until the disease has been ablated.

(B) A patient suffering from an inflammatory disease mediated by ICAM-1 is treated with ISIS-2302, an oligonucleotide synthesized according to Examples 1–4, and having the sequence GCCCAAGCTGGCATCCGTCA (SEQ ID NO:127). 1–1000 μg/kg body weight of oligonucleotide is incorporated into a pharmaceutically acceptable carrier and administered intravenously or intramuscularly. Treatment may be repeated as necessary until the disease has been ablated.

(C) A patient suffering from retinitis caused by cytomegalovirus is treated with ISIS-2922, an oligonucleotide synthesized according to Examples 1–4, and having the sequence GCGTTTGCTCTTCTTCTTGCG (SEQ ID NO:128). 1–1000 μg/kg body weight of oligonucleotide is incorporated into a pharmaceutically acceptable carrier and administered intravitreally. Treatment may be repeated as necessary until the infection is ablated.

(D) A patient suffering from C-raf kinase-mediated cancer is treated with ISIS-5132, an oligonucleotide synthesized according to Examples 1–4, and having the sequence TCCCGCCTGTGACATGCATT (SEQ ID NO:130). 1–1000 μg/kg body weight of oligonucleotide is incorporated into a pharmaceutically acceptable carrier and administered intravenously or intramuscularly. Treatment may be repeated as necessary until the disease has been ablated.

(E) A patient suffering from C-raf kinase-mediated cancer is treated with ISIS-2503 (SEQ ID NO:131), ISIS-2570 (SEQ ID NO:132) or ISIS-6957 (SEQ ID NO:133), each of which is synthesized according to the procedures of Examples 1–4. 1–1000 μg/kg body weight of oligonucleotide is incorporated into a pharmaceutically acceptable carrier and administered intravenously or intramuscularly. Treatment may be repeated as necessary until the disease has been ablated.

(F) A patient suffering from a PKC-α-mediated cancer is treated with ISIS-3521, an oligonucleotide synthesized according to Examples 1–4, and having the sequence GTTCTCGCTGGTGAGTTTCA (SEQ ID NO:2). 1–1000 μg/kg body weight of oligonucleotide is incorporated into a pharmaceutically acceptable carrier and administered intravenously or intramuscularly. Treatment may be repeated as necessary until the disease has been ablated.

(G) A patient suffering from psoriasis is treated with ISIS-3521, an oligonucleotide synthesized according to Examples 1–4, and having the sequence GTTCTCGCTGGTGAGTTTCA (SEQ ID NO:2). 1–1000 μg/kg body weight of oligonucleotide is incorporated into a pharmaceutically acceptable carrier and administered intravenously, intramuscularly or topically. Treatment may be repeated as necessary until the disease has been ablated.

(H) A patient suffering from a cancer mediated by the $\beta_I$, $\beta_{II}$, $\gamma$, $\delta$, $\epsilon$, $\zeta$ and/or $\eta$ isoform of PKC is treated with one or more oligonucleotides synthesized according to Examples 1–4 having a sequence complementary to a portion of the $\beta_I$, $\beta_{II}$, $\gamma$, $\delta$, $\epsilon$, $\zeta$ and/or $\eta$ isoform(s) which mediate(s) the cancer. 1–1000 μg/kg body weight of oligonucleotide is incorporated into a pharmaceutically acceptable carrier and administered intravenously, intramuscularly, intraventricularly or intrathecally. Treatment may be repeated as necessary until the disease has been ablated.

What is claimed is:

1. An antisense oligonucleotide having up to 50 nucleoside units which specifically binds mRNA encoding an isoform of human Protein Kinase C, wherein said isoform of human Protein Kinase C is selected from the group consisting of PKC-$\beta_I$, PKC-$\beta_{II}$, PKC-$\gamma$, PKC-$\delta$, PKC-$\epsilon$, PKC-$\zeta$ and PKC-$\eta$, and said antisense oligonucleotide inhibits the expression of said isoform of human Protein Kinase C, at least about 75% of the nucleoside units of said antisense oligonucleotide being joined together by Sp phosphorothioate 3' to 5' linkages.

2. The antisense oligonucleotide of claim 1, wherein all of the nucleoside units are joined together by Sp phosphorothioate 3' to 5' linkages.

3. The antisense oligonucleotide of claim 1 wherein said isoform of Protein Kinase C is PKC-$\beta_I$.

4. The antisense oligonucleotide of claim 3 comprising SEQ ID NOS: 21, 22, 23, 24, 25, 26, 27, 28 or 29.

5. The antisense oligonucleotide of claim 1 wherein said isoform of human Protein Kinase C isoform is PKC-$\beta_{II}$.

6. The antisense oligonucleotide of claim 5 comprising SEQ ID NOS: 21, 22, 23, 24, 30, 31, 32, 33 or 34.

7. The antisense oligonucleotide of claim 1 wherein said isoform of human Protein Kinase C is PKC-$\gamma$.

8. The antisense oligonucleotide of claim 7 comprising SEQ ID NOS: 35, 36, 37, 38 or 39.

9. The antisense oligonucleotide of claim 1 wherein said isoform of human Protein Kinase C is PKC-$\eta$.

10. The antisense oligonucleotide of claim 9 comprising SEQ ID NOS: 40, 41, 42, 43, 44, 45, 46, 47, 48, 49, 50, 51, 54, 55, 56, 57, 58, 59, 60, 61 or 62.

11. The antisense oligonucleotide of claim 1 wherein said isoform of human Protein Kinase C is PKC-$\delta$.

12. The antisense oligonucleotide of claim 11 comprising SEQ ID NOS 67, 69, 74 or 75.

13. The antisense oligonucleotide of claim 1 wherein said isoform of human Protein Kinase C is PKC-$\epsilon$.

14. The antisense oligonucleotide of claim 13 comprising SEQ ID NOS: 87, 93, 96, 97, 98, 99, 100, 101, 102, 103, 104 or 105.

15. The antisense oligonucleotide of claim 1 wherein said isoform of human Protein Kinase C is PKC-$\zeta$.

16. The antisense oligonucleotide of claim 15 comprising SEQ ID NOS: 106, 107, 109, 110, 113, 115, 116, 117, 118 or 121.

17. A pharmaceutical composition comprising the antisense oligonucleotide of claim 1 and a pharmaceutically acceptable carrier or diluent.

18. A pharmaceutical composition comprising the antisense oligonucleotide of claim 2 and a pharmaceutically acceptable carrier or diluent.

19. The pharmaceutical composition of claim 17, wherein said antisense oligonucleotide comprises at least one of the following SEQ ID NOS: 21, 22, 23, 24, 25, 26, 27, 29, 29, 30, 31, 32, 33, 34, 35, 36, 37, 38, 39, 40, 41, 42, 43, 44, 45, 46, 47, 48, 49, 50, 51, 54, 55, 56, 57, 58, 59, 60, 61, 62, 67, 69, 74, 75, 87, 93, 96, 97, 98, 99, 100, 101, 102, 103, 104, 105, 106, 107, 109, 110, 113, 115, 116, 117, 118 or 121.

20. A pharmaceutical composition comprising two or more of the antisense oligonucleotide of claim 1 and a pharmaceutically acceptable carrier or diluent.

21. An antisense oligonucleotide having up to 50 nucleotide units which specifically binds mRNA encoding an isoform of human Protein Kinase C, said isoform of human Protein Kinase C being selected from the group consisting of PKC-$\beta_I$, PKC-$\beta_{II}$, PKC-$\gamma$, PKC-$\delta$, PKC-$\epsilon$, PKC-$\zeta$ and PKC-$\eta$; and said antisense oligonucleotide inhibits the expression of said isoform of human Protein Kinase C; at least about 75% of the nucleoside units of said antisense oligonucleotide being joined together by Rp phosphorothioate 3' to 5' linkages.

22. The antisense oligonucleotide of claim 21, wherein all of the nucleoside units are joined together by Rp phosphorothioate 3' to 5' linkages.

23. The antisense oligonucleotide of claim 21 wherein said isoform of human Protein Kinase C is PKC-$\beta_I$.

24. The antisense oligonucleotide of claim 23 comprising SEQ ID NOS: 21, 22, 23, 24, 25, 26, 27, 28or 29.

25. The antisense oligonucleotide of claim 21 wherein said isoform of human Protein Kinase C isoform is PKC-$\beta_{II}$.

26. The antisense oligonucleotide of claim 25 comprising SEQ ID NOS: 21, 22, 23, 24, 30, 31, 32, 33 or 34.

27. The antisense oligonucleotide of claim 21 wherein said isoform of human Protein Kinase C is PKC-$\gamma$.

28. The antisense oligonucleotide of claim 27 comprising SEQ ID NOS. 35, 36, 37, 38 or 39.

29. The antisense oligonucleotide of claim 21 wherein said isoform of human Protein Kinase C is PKC-$\eta$.

30. The antisense oligonucleotide of claim 29 comprise SEQ ID NOS: 40, 41, 42, 43, 44, 45, 46, 47, 48, 49, 50, 51, 54, 55, 56, 57, 58, 59, 60, 61 or 62.

31. The antisense oligonucleotide of claim 21 wherein said isoform of human Protein Kinase C is PKC-$\delta$.

32. The antisense oligonucleotide of claim 31 comprising SEQ ID NOS 67, 69, 74 or 75.

33. The antisense oligonucleotide of claim 21 wherein said isoform of human Protein Kinase C is PKC-$\epsilon$.

34. The antisense oligonucleotide of claim 33 comprising SEQ ID NOS. 87, 93, 96, 97, 98, 99, 100, 101, 102, 103, 104 or 105.

35. The antisense oligonucleotide of claim 21 wherein said isoform of human Protein Kinase C is PKC-$\zeta$.

36. The antisense oligonucleotide of claim 35 comprising SEQ ID NOS. 106, 107, 109, 110, 113, 115, 116, 117, 118 or 121.

37. A pharmaceutical composition comprising the antisense oligonucleotide of claim 21 and a pharmaceutically acceptable carrier or diluent.

38. A pharmaceutical composition comprising the antisense oligonucleotide of claim 22 and a pharmaceutically acceptable carrier or diluent.

39. The pharmaceutical composition of claim 37, wherein said antisense oligonucleotide comprises at least one of the following SEQ ID NOS: 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 54, 55, 56, 57, 58, 59, 60, 61, 62, 67, 69, 74, 75, 87, 93, 96, 97, 98, 99, 100, 101, 102, 103, 104, 105, 106, 107, 109, 110, 113, 115, 116, 117, 118 or 121.

40. A pharmaceutical composition comprising two or more different antisense oligonucleotides in accordance with claim 21 together with a pharmaceutically acceptable carrier or diluent.

41. A pharmaceutical composition comprising the antisense oligonucleotide of claim 1 and a pharmaceutically acceptable carrier or diluent.

42. A pharmaceutical composition comprising the antisense oligonucleotide of claim 21 and a pharmaceutically acceptable carrier or diluent.

* * * * *

UNITED STATES PATENT AND TRADEMARK OFFICE
CERTIFICATE OF CORRECTION

PATENT NO. : 6,339,066 B1
DATED : January 15, 2002
INVENTOR(S) : Bennett et al.

Page 1 of 1

It is certified that error appears in the above-identified patent and that said Letters Patent is hereby corrected as shown below:

Title page,
References Cited: 4,689,320, please delete "Kajo" and insert therefor -- Kaji --;

Column 19,
Line 62, please delete "$T_m$" and insert therefor -- Tm --;

Column 23,
Line 50, please delete "Si" and insert therefor -- S1 --;

Column 33,
Line 35, please delete "31P" and insert therefor -- $^{31}$P --;

Column 39,
Line 61, please delete "549" and insert therefor -- A549 --;

Signed and Sealed this

Twenty-first Day of May, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,339,066 B1 |
| APPLICATION NO. | : 08/829637 |
| DATED | : January 15, 2002 |
| INVENTOR(S) | : C. Frank Bennett et al. |

It is certified that error appears in the above-identified patent and that said Letters Patent is hereby corrected as shown below:

1) Title Page:
Item [63], Related U.S. Application Data, please delete

"Continuation-in-part of application No. 08/481,066, filed on Jun. 7, 1995, now Pat. No. 5,959,096, which is a continuation-in-part of application No. 08/089,996, filed Jul. 9, 1993, now Pat. No. 5,703,054, which is a continuation-in-part of application No. 07/852,852, filed Mar. 16, 1992, now abandoned, said application No. 08/829,637, is a continuation-in-part of application No. 08/468,569, filed Jun. 6, 1995, now Pat. No. 5,620,963, which is a continuation-in-part of application No. 08/297,703, filed Aug. 29, 1994, now Pat. No. 5,506,212, which is a continuation of application No. 07/777,007, filed Oct. 16, 1991, now Pat. No. 5,246,432, and a continuation-in-part of application No. 08/058,023, filed May 5, 1993, now Pat. No. 5,521,302, which is a division of application No. 07/777,760, filed Oct 15, 1991, now Pat. No. 5,212,295, and a continuation-in-part of application No. 07/777,007, which is a continuation-in-part of application No. 07/463,358, filed Jan. 11, 1990, now abandoned, said application No. 08/829,637, is a continuation-in-part of application No. 08/469,851, filed on Jun. 6, 1995, now Pat. No. 5,587,361, which is a continuation-in-part of application No. 08/297,703, which is a continuation of application No. 07/777,007, and a continuation-in-part of application No. 08/058,023, which is a division of application No. 07/777,760, and a continuation-in-part of application No. 07/777,007, which is a continuation-in-part of application No. 07/463,358, said application No. 08/829,637, is a continuation-in-part of application No. 08/470,129, filed Jun. 6, 1995, now Pat. No. 5,635,488, which is a continuation-in-part of application No. 08/297,703, which is a continuation of application No. 07/777,007, and a continuation-in-part of application No. 08/058,023, which is a division of application No. 07/777,760, and a continuation-in-part of application No. 07/777,007, which is a continuation-in-part of application No. 07/463,358, said application No. 08/829,637, is a continuation-in-part of application No. 07/770,760, which is a continuation-in-part of application No. PCT/US91/00243, filed Jan. 11, 1991, which is a continuation-in-part of application No. 07/463,358, and a continuation-in-part of application No. 07/566,977. filed Aug. 13, 1990, now abandoned, said application No. 08/829,637, is a continuation-in-part of application No. 08/297,703, which is a continuation of application No. 07/777,007, which is a continuation-in-part of application No. 07/463,368."

UNITED STATES PATENT AND TRADEMARK OFFICE
CERTIFICATE OF CORRECTION

| | | |
|---|---|---|
| PATENT NO. | : 6,339,066 B1 | Page 2 of 3 |
| APPLICATION NO. | : 08/829637 | |
| DATED | : January 15, 2002 | |
| INVENTOR(S) | : C. Frank Bennett et al. | |

It is certified that error appears in the above-identified patent and that said Letters Patent is hereby corrected as shown below:

and insert therefor

--Continuation-in-part of application No. 08/481,066, filed on Jun. 7, 1995, now Pat. No. 5,959,096, which is a continuation-in-part of application No. 08/089,996, filed Jul. 9, 1993, now Pat. No. 5,703,054, which is a continuation-in-part of application No. 07/852,852, filed Mar. 16, 1992, now abandoned, said application No. 08/829,637, is a continuation-in-part of application No. 08/468,569, filed Jun. 6, 1995, now Pat. No. 5,620,963, which is a continuation-in-part of application No. 08/297,703, tiled Aug. 29, 1994, now Pat. No. 5,506,212, which is a continuation of application No. 07/777,007, filed Oct. 16, 1991, now abandoned, and a continuation-in-part of application No. 08/058,023, filed May 5, 1993, now Pat. No. 5,521,302, which is a division of application No. 07/777,670, filed Oct. 15, 1991, now Pat. No. 5,212,295, and a continuation-in-part of application No. 07/777,007, which is a continuation-in-part of application No. 07/463,358, filed Jan. 11, 1990, now abandoned, said application No. 08/829,637, is a continuation-in-part of application No. 08/469,851, filed on Jun. 6, 1995, now Pat. No. 5,587,361, which is a continuation-in-part of application No. 08/297,703, which is a continuation of application No. 07/777,007, and a continuation-in-part of application No. 08/058,023, which is a division of application No. 07/777,670, and a continuation-in-part of application No. 07/777,007, which is a continuation-in-part of application No. 07/463,358, said application No. 08/829,637, is a continuation-in-part of application No. 08/470,129, filed Jun. 6, 1995, now Pat. No. 5,635,488, which is a continuation-in-part of application No. 08/297,703, which is a continuation of application No. 07/777,007, and a continuation-in-part of application No. 08/058,023, which is a division of application No. 07/777,670, and a continuation-in-part of application No. 07/777,007, which is a continuation-in-part of application No. 07/463,358, said application No. 08/829,637, is a continuation-in-part of application No. 07/770,670, which is a continuation-in-part of application No. PCT/US91/00243, filed Jan. 11, 1991, which is a continuation-in-part of application No. 07/463,358, and a continuation-in-part of application No. 07/566,977, filed Aug. 13, 1990, now abandoned,

UNITED STATES PATENT AND TRADEMARK OFFICE
CERTIFICATE OF CORRECTION

PATENT NO.       : 6,339,066 B1
APPLICATION NO.  : 08/829637
DATED            : January 15, 2002
INVENTOR(S)      : C. Frank Bennett et al.

It is certified that error appears in the above-identified patent and that said Letters Patent is hereby corrected as shown below:

Item [63], Related U.S. Application Data, and insert therefor (cont'd)

said application No. 08/829,637, is a continuation-in-part of application No. 08/297,703, which is a continuation of application No. 07/777,007, which is a continuation-in-part of application No. 07/463,358.--

Signed and Sealed this

Fourth Day of September, 2007

JON W. DUDAS
*Director of the United States Patent and Trademark Office*

SEQUENCE LISTING (1) GENERAL INFORMATION:

(iii) NUMBER OF SEQUENCES: 136

(2) INFORMATION FOR SEQ ID NO: 1:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 1:

CCCCAACCAC CTCTTGCTCC                                      20

(2) INFORMATION FOR SEQ ID NO: 2:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 2:

GTTCTCGCTG GTGAGTTTCA                                                   20

(2) INFORMATION FOR SEQ ID NO: 3:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 3:

AAAACGTCAG CCATGGTCCC                                                   20

(2) INFORMATION FOR SEQ ID NO: 4:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 4:

GGATTCACTT CCACTGCGGG                                                   20

(2) INFORMATION FOR SEQ ID NO: 5:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 5:

GAGACCCTGA ACAGTTGATC                                                   20

(2) INFORMATION FOR SEQ ID NO: 6:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 6:

CCCGGGAAAA CGTCAGCCAT                                                   20

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 7:

CTGCCTCAGC GCCCCTTTGC                                                   20

```
(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 8:

AGTCGGTGCA GTGGCTGGAG                                               20

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 9:

GCAGAGGCTG GGGACATTGA                                               20

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 10:

GGGCTGGGGA GGTGTTTGTT                                               20

(2) INFORMATION FOR SEQ ID NO: 11:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 11:

CACTGCGGGG AGGGCTGGGG                                               20

(2) INFORMATION FOR SEQ ID NO: 12:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 12:

AGCCGTGGCC TTAAAATTTT                                               20

(2) INFORMATION FOR SEQ ID NO: 13:

(i) SEQUENCE CHARACTERISTICS:
        (A) LENGTH: 20
```

(B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 13:

ATTTTCAGGC CTCCATATGG                                           20

(2) INFORMATION FOR SEQ ID NO: 14:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 14:

AAGAGAGAGA CCCTGAACAG                                           20

(2) INFORMATION FOR SEQ ID NO: 15:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 15:

GATAATGTTC TTGGTTGTAA                                           20

(2) INFORMATION FOR SEQ ID NO: 16:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 16:

ATGGGGTGCA CAAACTGGGG                                           20

(2) INFORMATION FOR SEQ ID NO: 17:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 17:

GTCAGCCATG GTCCCCCCCC                                           20

(2) INFORMATION FOR SEQ ID NO: 18:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 18:

CGCCGTGGAG TCGTTGCCCG                                               20

(2) INFORMATION FOR SEQ ID NO: 19:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 19:

TCAAATGGAG GCTGCCCGGC                                               20

(2) INFORMATION FOR SEQ ID NO: 20:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 20:

TGGAATCAGA CACAAGCCGT                                               20

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 21:

CATCTTGCGC GCGGGGAGCC                                               20

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 22:

TGCGCGCGGG GAGCCGGAGC                                               20

(2) INFORMATION FOR SEQ ID NO: 23:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 23:

```
CGAGAGGTGC CGGCCCCGGG                                                    20

(2) INFORMATION FOR SEQ ID NO: 24:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 24:

CTCTCCTCGC CCTCCGTCGG                                                    20

(2) INFORMATION FOR SEQ ID NO: 25:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 25:

TGGAGTTTGC ATTCACCTAC                                                    20

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 26:

AAAGGCCTCT AAGACAAGCT                                                    20

(2) INFORMATION FOR SEQ ID NO: 27:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 27:

GCCAGCATGT GCACCGTGAA                                                    20

(2) INFORMATION FOR SEQ ID NO: 28:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 28:

ACACCCCAGG CTCAACGATG                                                    20

(2) INFORMATION FOR SEQ ID NO: 29:
```

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 29:

CCGAAGCTTA CTCACAATTT                    20

(2) INFORMATION FOR SEQ ID NO: 30:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 30:

ACTTAGCTCT TGACTTCGGG                    20

(2) INFORMATION FOR SEQ ID NO: 31:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 31:

ATGCTGCGGA AAATAAATTG                    20

(2) INFORMATION FOR SEQ ID NO: 32:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 32:

ATTTTATTTT GAGCATGTTC                    20

(2) INFORMATION FOR SEQ ID NO: 33:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 33:

TTTGGGGATG AGGGTGAGCA                    20

(2) INFORMATION FOR SEQ ID NO: 34:

(i) SEQUENCE CHARACTERISTICS:
        (A) LENGTH: 20
        (B) TYPE: nucleic acid (C) STRANDEDNESS: single
            (D) TOPOLOGY: linear (iv) ANTI-SENSE: yes (xi) SEQUENCE DESCRIPTION: SEQ ID NO: 34:

CCCATTCCCA CAGGCCTGAG                                                   20

(2) INFORMATION FOR SEQ ID NO: 35:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 35:

CGGAGCGCGC CAGGCAGGGA                                                   20

(2) INFORMATION FOR SEQ ID NO: 36:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 36:

CCTTTTCCCA GACCAGCCAT                                                   20

(2) INFORMATION FOR SEQ ID NO: 37:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 37:

GGCCCCAGAA ACGTAGCAGG                                                   20

(2) INFORMATION FOR SEQ ID NO: 38:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 38:

GGATCCTGCC TTTCTTGGGG                                                   20

(2) INFORMATION FOR SEQ ID NO: 39:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 39:

CAGCCATGGC CCCAGAAACG                                               20

(2) INFORMATION FOR SEQ ID NO: 40:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 40:

CGACATGCCG GCGCCGCTGC                                               20

(2) INFORMATION FOR SEQ ID NO: 41:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 41:

CAGACGACAT GCCGGCGCCG                                               20

(2) INFORMATION FOR SEQ ID NO: 42:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 42:

GCCTGCTTCG CAGCGGGAGA                                               20

(2) INFORMATION FOR SEQ ID NO: 43:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 43:

ACAGGTGCAG GAGTCGAGGC                                               20

(2) INFORMATION FOR SEQ ID NO: 44:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 44:

GTCCCGTCTC AGGCCAGCCC                                               20

(2) INFORMATION FOR SEQ ID NO: 45:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 45:

CCTCACCGAT GCGGACCCTC                                                   20

(2) INFORMATION FOR SEQ ID NO: 46:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 46:

ATTGAACTTC ATGGTGCCAG                                                   20

(2) INFORMATION FOR SEQ ID NO: 47:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 47:

TCTCACTCCC CATAAGGCTA                                                   20

(2) INFORMATION FOR SEQ ID NO: 48:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 48:

TTCCTTTGGG TTCTCGTGCC                                                   20

(2) INFORMATION FOR SEQ ID NO: 49:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 49:

TTCCATCCTT CGACAGAGTT                                                   20

(2) INFORMATION FOR SEQ ID NO: 50:

```
    (i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 50:

AGGCTGATGC TGGGAAGGTC                                               20

(2) INFORMATION FOR SEQ ID NO: 51:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 51:

GTTCTAAGGC TGATGCTGGG                                               20

(2) INFORMATION FOR SEQ ID NO: 52:

(i) SEQUENCE CHARACTERISTICS:
        (A) LENGTH: 18
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:52:

TTCTCGCTGG TGAGTTTC                                                 18

(2) INFORMATION FOR SEQ ID NO: 53:

(i) SEQUENCE CHARACTERISTICS:
        (A) LENGTH: 17
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 53:

TCTCGCTGGT GAGTTTC                                                  17

(2) INFORMATION FOR SEQ ID NO: 54:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 54:

AACTCGAGGT GGCCGCCGTC                                               20

(2) INFORMATION FOR SEQ ID NO: 55:

(i) SEQUENCE CHARACTERISTICS:
        (A) LENGTH: 20
        (B) TYPE: nucleic acid
        (C) STRANDEDNESS: single
```

(D) TOPOLOGY: linear (iv) ANTI-SENSE: yes (xi) SEQUENCE DESCRIPTION: SEQ ID NO: 55:

CGCCTTCGCA TAGCCCTTTG                                                         20

(2) INFORMATION FOR SEQ ID NO: 56:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 56:

GGAAGGGGTG ATTGCGGGCC                                                         20

(2) INFORMATION FOR SEQ ID NO: 57:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 57:

AACACGCCCA TTGCCCACCA                                                         20

(2) INFORMATION FOR SEQ ID NO: 58:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 58:

GTCTCAAGAT GGCGTGCTCG                                                         20

(2) INFORMATION FOR SEQ ID NO: 59:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 59:

GCGATGGTTC AGCTGGGCCC                                                         20

(2) INFORMATION FOR SEQ ID NO: 60:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 60:

GCCCTCTCTC TCACTCCCCA                                          20

(2) INFORMATION FOR SEQ ID NO: 61:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 61:

CTGGGAAGGT CCGATAGAGG                                          20

(2) INFORMATION FOR SEQ ID NO: 62:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 62:

AAGGCTGATG CTGGGAAGGT                                          20

(2) INFORMATION FOR SEQ ID NO: 63:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 63:

GCAGGAACGG CGCCATGGTG                                          20

(2) INFORMATION FOR SEQ ID NO: 64:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 64:

CTGGTTCGCC TCGTCCTCGG                                          20

(2) INFORMATION FOR SEQ ID NO: 65:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 65:

ATCTGGATGA CGCGCCCCTC                                          20

(2) INFORMATION FOR SEQ ID NO: 66:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 66:

TTCTTGCAGC GCTCGGCCAG                                    20

(2) INFORMATION FOR SEQ ID NO: 67:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 67:

TGCAATCCAC GTCCTCCAGG                                    20

(2) INFORMATION FOR SEQ ID NO: 68:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 68:

GGCTCCGCGG CGGTTCATCG                                    20

(2) INFORMATION FOR SEQ ID NO: 69:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 69:

AAGCGGTGCG GCATGTCGAT                                    20

(2) INFORMATION FOR SEQ ID NO: 70:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 70:

GCAGGCTGCC GCAGTGGTCA                                    20

(2) INFORMATION FOR SEQ ID NO: 71:

(i) SEQUENCE CHARACTERISTICS:

(A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 71:

CCTCCCCAGC AACTCCGGTC                                               20

(2) INFORMATION FOR SEQ ID NO: 72:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 72:

AGCGGCCTTT GTCCTGGATG                                               20

(2) INFORMATION FOR SEQ ID NO: 73:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 73:

GGCCATCCCG GTCCAACAGC                                               20

(2) INFORMATION FOR SEQ ID NO: 74:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 74:

GGTGCTGGCC CGGCTCTCCC                                               20

(2) INFORMATION FOR SEQ ID NO: 75:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 75:

GGACCCCGAA AGACCACCAG                                               20

(2) INFORMATION FOR SEQ ID NO: 76:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 76:

GTGGCTCCAA CCTCCGCTTT                                                    20

(2) INFORMATION FOR SEQ ID NO: 77:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 77:

AGGAGGTGCT CGAATTTGGG                                                    20

(2) INFORMATION FOR SEQ ID NO: 78:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 78:

ACTACCATGG TCGGGGCGGG                                                    20

(2) INFORMATION FOR SEQ ID NO: 79:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 79:

GTCCCACCGC ATGGCGCAGC                                                    20

(2) INFORMATION FOR SEQ ID NO: 80:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 80:

GTTTGGCCGA TGCGCGAGTC                                                    20

(2) INFORMATION FOR SEQ ID NO: 81:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 81:

TGCAGTTGGC CACGAAGTCG                                                  20

(2) INFORMATION FOR SEQ ID NO: 82:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 82:

GTGGGGCATG TTGACGCTGA                                                  20

(2) INFORMATION FOR SEQ ID NO: 83:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 83:

CCAGAGCAGG GACCCACAGT                                                  20

(2) INFORMATION FOR SEQ ID NO: 84:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 84:

TCTCCTCGGT TGTCAAATGA                                                  20

(2) INFORMATION FOR SEQ ID NO: 85:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 85:

CGGTGCTCCT CTCCTCGGTT                                                  20

(2) INFORMATION FOR SEQ ID NO: 86:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 86:

AGCCAAAATC CTCTTCTCTG                                                  20

(2) INFORMATION FOR SEQ ID NO: 87:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 87:

CATGAGGGCC GATGTGACCT                                          20

(2) INFORMATION FOR SEQ ID NO: 88:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 88:

ATCCCTTCCT TGCACATCCC                                          20

(2) INFORMATION FOR SEQ ID NO: 89:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 89:

CCCCAGGGCC CACCAGTCCA                                          20

(2) INFORMATION FOR SEQ ID NO: 90:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 90:

AGCACCCCCA GGGCCCACCA                                          20

(2) INFORMATION FOR SEQ ID NO: 91:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 91:

CGTACATCAG CACCCCCAGG                                          20

(2) INFORMATION FOR SEQ ID NO: 92:

(i) SEQUENCE CHARACTERISTICS:
        (A) LENGTH: 20

(B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 92:

CCAGCCATCA TCTCGTACAT                                               20

(2) INFORMATION FOR SEQ ID NO: 93:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 93:

TGCCACACAG CCCAGGCGCA                                               20

(2) INFORMATION FOR SEQ ID NO: 94:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 94:

TCAGGGCATC AGGTCTTCAC                                               20

(2) INFORMATION FOR SEQ ID NO: 95:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 95:

CTCTCAGGGC ATCAGGTCTT                                               20

(2) INFORMATION FOR SEQ ID NO: 96:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 96:

AAGGAAAGTC TGCGGCCGGG                                               20

(2) INFORMATION FOR SEQ ID NO: 97:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 97:

TGGCGGCTCC CGTTCTGCAG                                                    20

(2) INFORMATION FOR SEQ ID NO: 98:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 98:

GCTTCCTCGG CCGCATGCGT                                                    20

(2) INFORMATION FOR SEQ ID NO: 99:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 99:

TTGACGCTGA ACCGCTGGGA                                                    20

(2) INFORMATION FOR SEQ ID NO: 100:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 100:

GCCCGGTGCT CCTCTCCTCG                                                    20

(2) INFORMATION FOR SEQ ID NO: 101:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 101:

GGGCCGATGT GACCTCTGCA                                                    20

(2) INFORMATION FOR SEQ ID NO: 102:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 102:

TGGAGGAACA TGAGGGCCGA                                              20

(2) INFORMATION FOR SEQ ID NO: 103:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 103:

CCCCCAGGGC CCACCAGTCC                                              20

(2) INFORMATION FOR SEQ ID NO: 104:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 104:

TGCGATGCCA CACAGCCCAG                                              20

(2) INFORMATION FOR SEQ ID NO: 105:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 105:

TGGGCTCTCA GGGCATCAGG                                              20

(2) INFORMATION FOR SEQ ID NO: 106:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 106:

CGCCGCTCCC TTCCATCTTG                                              20

(2) INFORMATION FOR SEQ ID NO: 107:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 107:

CCCCGTAATG CGCCTTGAGG                                              20

(2) INFORMATION FOR SEQ ID NO: 108:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 108:

CTGTCCACCC ACTTGAGGGT                                          20

(2) INFORMATION FOR SEQ ID NO: 109:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 109:

TTGGAAGAGG TGGCCGTTGG                                          20

(2) INFORMATION FOR SEQ ID NO: 110:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 110:

CCTGTTAAAG CGCTTGGCTT                                          20

(2) INFORMATION FOR SEQ ID NO: 111:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 111:

TGCAGGTCAG CGGGACGAGG                                          20

(2) INFORMATION FOR SEQ ID NO: 112:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 112:

AGCCCCTGAG AGATTTTGAT                                          20

(2) INFORMATION FOR SEQ ID NO: 113:

(i) SEQUENCE CHARACTERISTICS:
        (A) LENGTH: 20
        (B) TYPE: nucleic acid

```
            (C) STRANDEDNESS: single
            (D) TOPOLOGY: linear (iv) ANTI-SENSE: yes (xi) SEQUENCE DESCRIPTION: SEQ ID NO: 113:

TTCTTCAACC GCACCAGGAG                                           20

(2) INFORMATION FOR SEQ ID NO: 114:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 114:

TCCTTGCACA TGCCGTAGTC                                           20

(2) INFORMATION FOR SEQ ID NO: 115:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 115:

GGAGCGCCCG GCCATCATCT                                           20

(2) INFORMATION FOR SEQ ID NO: 116:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 116:

GGGCTCGCTG GTGAACTGTG                                           20

(2) INFORMATION FOR SEQ ID NO: 117:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 117:

GACGCACGCG GCCTCACACC                                           20

(2) INFORMATION FOR SEQ ID NO: 118:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes
```

(xi) SEQUENCE DESCRIPTION: SEQ ID NO: 118:

TCGGAGCCGT GCCCAGCCTG                                                  20

(2) INFORMATION FOR SEQ ID NO: 119:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 119:

CGGGCCAGGT GTGAGGGACT                                                  20

(2) INFORMATION FOR SEQ ID NO: 120:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 120:

CCGCGACGCA GGCACAGCAG                                                  20

(2) INFORMATION FOR SEQ ID NO: 121:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 121:

GGTCAGTGCA TCGAGTTCTG                                                  20

(2) INFORMATION FOR SEQ ID NO: 122:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO: 122:

CCTTTCGCGA CCCAACACTA                                                  20

(2) INFORMATION FOR SEQ ID NO: 123:

(i) SEQUENCE CHARACTERISTICS:
            (A) LENGTH: 20
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:123:

GCCTTTCGCG ACCCAACACT                                                  20

(2) INFORMATION FOR SEQ ID NO: 124:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:124:

GTACCACAAG GCCTTTCGCG                                            20

(2) INFORMATION FOR SEQ ID NO: 125:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:125:

GTGCTCATGG TGCACGGTCT                                            20

(2) INFORMATION FOR SEQ ID NO: 126:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:126:

TTTAGGATTC GTGCTCATGG                                            20

(2) INFORMATION FOR SEQ ID NO: 127:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:127:

GCCCAAGCTG GCATCCGTCA                                            20

(2) INFORMATION FOR SEQ ID NO: 128:

(i) SEQUENCE CHARACTERISTICS:
        (A) LENGTH: 21
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:128:

GCGTTTGCTC TTCTTCTTGC G                                          21

(2) INFORMATION FOR SEQ ID NO: 129:

(i) SEQUENCE CHARACTERISTICS:
           (A) LENGTH: 14
           (B) TYPE: nucleic acid
           (C) STRANDEDNESS: single
           (D) TOPOLOGY: linear (iv) ANTI-SENSE: yes (xi) SEQUENCE DESCRIPTION: SEQ ID NO:129:

GACTATGCAA GTAC                                                      14

(2) INFORMATION FOR SEQ ID NO: 130:

(i) SEQUENCE CHARACTERISTICS:
           (A) LENGTH: 20
           (B) TYPE: nucleic acid
           (C) STRANDEDNESS: single
           (D) TOPOLOGY: linear (iv) ANTI-SENSE: yes (xi) SEQUENCE DESCRIPTION: SEQ ID NO:130:

TCCCGCCTGT GACATGCATT                                                20

(2) INFORMATION FOR SEQ ID NO: 131:

(i) SEQUENCE CHARACTERISTICS:
           (A) LENGTH: 20
           (B) TYPE: nucleic acid
           (C) STRANDEDNESS: single
           (D) TOPOLOGY: linear (iv) ANTI-SENSE: yes (xi) SEQUENCE DESCRIPTION: SEQ ID NO:131:

TCCGTCATCG CTCCTCAGGG                                                20

(2) INFORMATION FOR SEQ ID NO: 132:

(i) SEQUENCE CHARACTERISTICS:
           (A) LENGTH: 17
           (B) TYPE: nucleic acid
           (C) STRANDEDNESS: single
           (D) TOPOLOGY: linear (iv) ANTI-SENSE: yes (xi) SEQUENCE DESCRIPTION: SEQ ID NO:132:

CCACACCGAC GGCGCCC                                                   17

(2) INFORMATION FOR SEQ ID NO: 133:

(i) SEQUENCE CHARACTERISTICS:
           (A) LENGTH: 20
           (B) TYPE: nucleic acid
           (C) STRANDEDNESS: single
           (D) TOPOLOGY: linear (iv) ANTI-SENSE: yes (xi) SEQUENCE DESCRIPTION: SEQ ID NO:133:

CAGTGCCTGC GCCGCGCTCG                                                20

(2) INFORMATION FOR SEQ ID NO: 134:

(i) SEQUENCE CHARACTERISTICS:
           (A) LENGTH: 15
           (B) TYPE: nucleic acid
           (C) STRANDEDNESS: single

```
          (D) TOPOLOGY: linear (iv) ANTI-SENSE: yes (xi) SEQUENCE DESCRIPTION: SEQ ID NO:134:

CGACTATGCA AGTAC                                                    15

(2) INFORMATION FOR SEQ ID NO: 135:

(i) SEQUENCE CHARACTERISTICS:
          (A) LENGTH: 55
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO:135:

GTACTTGCAT AGTCGATCGG AAAATAGGGT TCTCATCTCC                          40

CGGGATTTGG TTGAG                                                    55

(2) INFORMATION FOR SEQ ID NO: 136:

(i) SEQUENCE CHARACTERISTICS:
          (A) LENGTH: 41
          (B) TYPE: nucleic acid
          (C) STRANDEDNESS: single
          (D) TOPOLOGY: linear (iv) ANTI-SENSE: yes (xi) SEQUENCE DESCRIPTION: SEQ ID NO:136:

CTCAACCAAA TCCCGGGAGA TGAGAACCCT ATTTTCCGAT C                        41
```